US012012394B2

(12) United States Patent
Tu et al.

(10) Patent No.: US 12,012,394 B2
(45) Date of Patent: Jun. 18, 2024

(54) ALPHA-SYNUCLEIN LIGANDS

(71) Applicant: Washington University, St. Louis, MO (US)

(72) Inventors: Zhude Tu, Frontenac, MO (US); Paul T. Kotzbauer, Clayton, MO (US); Xuyi Yue, St. Louis, MO (US); Dhruva D. Dhavale, St. Louis, MO (US)

(73) Assignee: Washington University, St. Louis, MO (US)

( * ) Notice: Subject to any disclaimer, the term of this patent is extended or adjusted under 35 U.S.C. 154(b) by 423 days.

(21) Appl. No.: 16/277,643

(22) Filed: Feb. 15, 2019

(65) Prior Publication Data

US 2019/0256492 A1 Aug. 22, 2019

Related U.S. Application Data

(60) Provisional application No. 62/632,352, filed on Feb. 19, 2018.

(51) Int. Cl.
| | | |
|---|---|---|
| *C07D 401/12* | (2006.01) | |
| *C07B 59/00* | (2006.01) | |
| *C07D 405/12* | (2006.01) | |
| *A61K 51/04* | (2006.01) | |

(52) U.S. Cl.
CPC .......... *C07D 401/12* (2013.01); *C07B 59/002* (2013.01); *C07D 405/12* (2013.01); *A61K 51/0455* (2013.01); *A61K 2123/00* (2013.01); *C07B 2200/05* (2013.01)

(58) Field of Classification Search
CPC .. C07D 405/12; C07B 59/002; A61K 51/0455
See application file for complete search history.

(56) References Cited

U.S. PATENT DOCUMENTS

| | | | |
|---|---|---|---|
| 6,180,631 B1 * | 1/2001 | McMahon ................ | A61P 1/16 514/249 |
| 7,084,156 B2 | 8/2006 | DeVita et al. | |
| 7,087,758 B2 | 8/2006 | Bryan et al. | |
| 7,485,647 B2 | 2/2009 | Moriya et al. | |
| 8,399,674 B2 | 3/2013 | Kolczewski et al. | |
| 9,290,463 B2 | 3/2016 | Mann et al. | |
| 9,303,015 B2 | 4/2016 | Leonard et al. | |
| 9,796,718 B2 | 10/2017 | Mitchell et al. | |
| 2003/0105073 A1 * | 6/2003 | Haughan ............... | C07D 413/14 546/156 |
| 2005/0026915 A1 | 2/2005 | DeVita et al. | |
| 2011/0182812 A1 | 7/2011 | Szardenings et al. | |
| 2013/0315825 A1 | 5/2013 | Tu et al. | |
| 2014/0107096 A1 | 4/2014 | Leonard et al. | |
| 2017/0189566 A1 | 7/2017 | Tu et al. | |

FOREIGN PATENT DOCUMENTS

| | | |
|---|---|---|
| EP | 0446604 A2 | 9/1991 |
| WO | 2009/109477 A1 | 9/2009 |
| WO | 2013/048832 A1 | 4/2013 |
| WO | 2015/091558 A1 | 6/2015 |
| WO | WO-2016120808 A1 * | 8/2016 |

OTHER PUBLICATIONS

Solekhova et al. Russ. J. Org. Chem. 38 (2002) 8, 1192-1194 (Year: 2002).*
Rombouts et al. "Discovery of N-(Pyridin-4-yl)-1,5-naphthyridin-2-amines as Potential Tau Pathology PET Tracers for Alzheimer's Disease", J. Med. Chem. 2017, 60, 1272-1291 (Year: 2017).*
Braak, H., et al., "Stages in the development of Parkinson's disease-related pathology," 2004, Cell Tissue Res., 318:121-134, 14 Pages.
Folstein, M.F., et al., ""Mini-mental state". A practical method for grading the cognitive state of patients for the clinician," 1975, J Psychiatr Res, 12:189-198, 10 Pages.
Frost, B., et al, "Propagation of tau misfolding from the outside to the inside of a cell," 2009, J. Biol. Chem. 284:12845-12852, 9 Pages.
Galvin, J.E., et al., "The AD8: a brief informant interview to detect dementia," 2005, Neurology 65:559-564, 6 Pages.
Giasson, B.I., et al., "Mutant and wild type human alpha-synucleins assemble into elongated filaments with distinct morphologies in vitro," 1999, J. Biol. Chem., 274:7619-7622, 5 Pages.
Huang, C., et al., "A new method for purification of recombinant human alpha-synuclein in *Escherichia coli*," 2005, Protein Expr Purif, 42:173-177, 1 Page, Abstract Only.
Hughes, A.J., et al, "Accuracy of clinical diagnosis of idiopathic Parkinson's disease: a clinico-pathological study of 100 cases," 1992, J. Neurol. Neurosurg. Psychiatry, 55:181-184, 4 Pages.
Kotzbauer, P.T., et al., "Current Status of the Development of PET Radiotracers for Imaging α-synuclein aggregates in Lewy Bodies and Lewy Neurites," 2017, Clinical and Translational Imaging, 5/1:3-14.
Li, W., et al., "Characterization of two VQIXXK motifs for tau fibrillization in vitro," 2006, Biochemistry, 45:15692-15701.
Yu, L., et al, "Synthesis and in vitro evaluation of alpha-synuclein ligands," 2012, Bioorg. Med. Chem., 20:4625-4634, 21 Pages.
Yue, X., et al., "Design, Synthesis and in vitro evaluation of quinolinyl analogues for alpha-synuclein aggregation," 2017, J Nucl Med, 58/Supp 1:347, Abstract Only 2 pages.
Yue, X., et al., "Design, Synthesis and in vitro evaluation of quinolinyl analogues for alpha-synuclein aggregation," 2018, Bioorg Med Chem Lett, 28/6:1011-1019, 24 pages.

\* cited by examiner

*Primary Examiner* — James W Rogers
(74) *Attorney, Agent, or Firm* — Stinson LLP

(57) ABSTRACT

The present invention generally relates to various compounds that are useful as α-synuclein ligands. The invention further relates to methods of using these compounds and their radiolabeled analogs for the detection of synucleinopathies, including Parkinson's disease (PD).

12 Claims, 21 Drawing Sheets
(2 of 21 Drawing Sheet(s) Filed in Color)

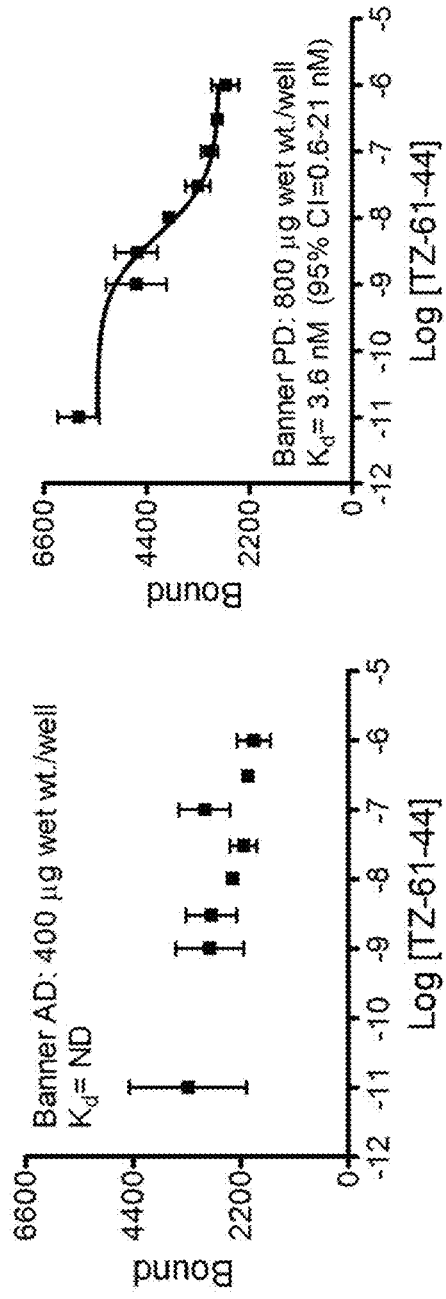
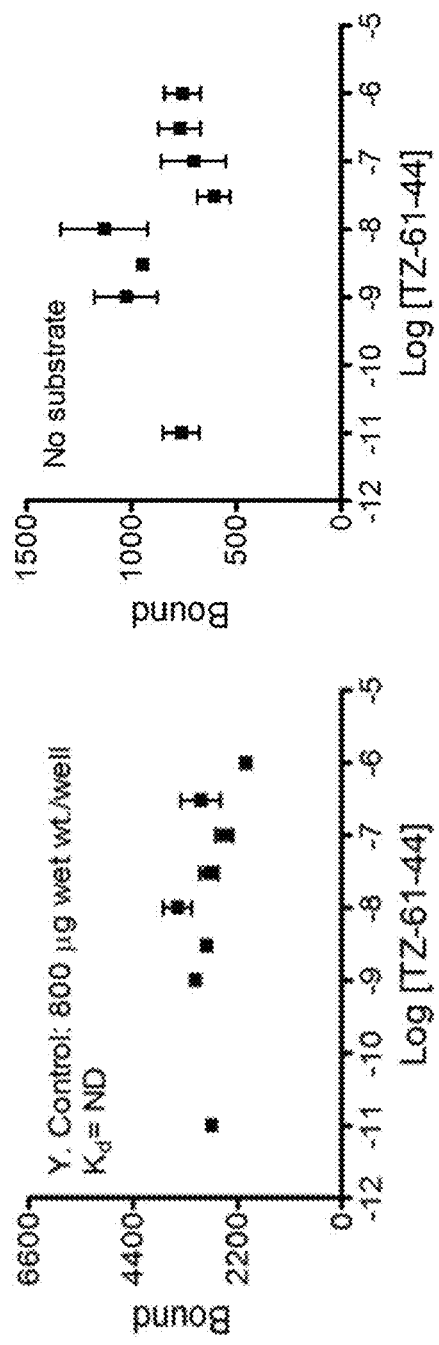
FIG. 2A
FIG. 2B
FIG. 2C
FIG. 2D

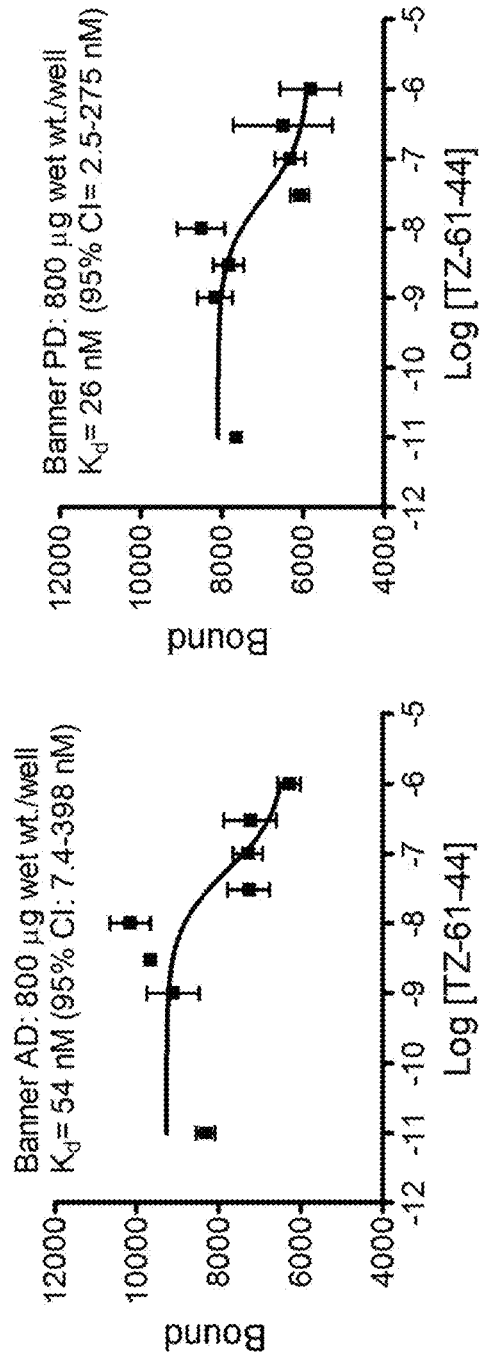
FIG. 3A
FIG. 3B
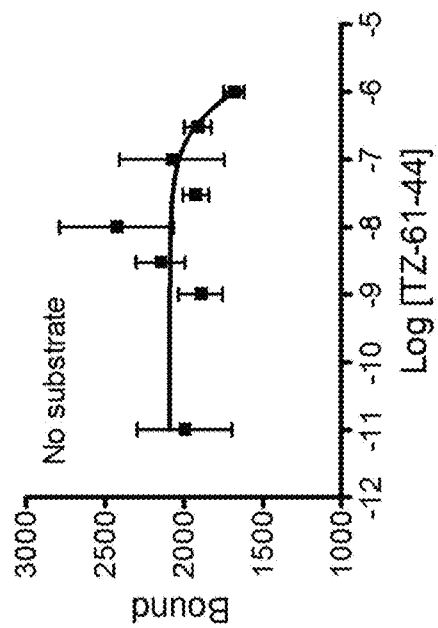
FIG. 3C
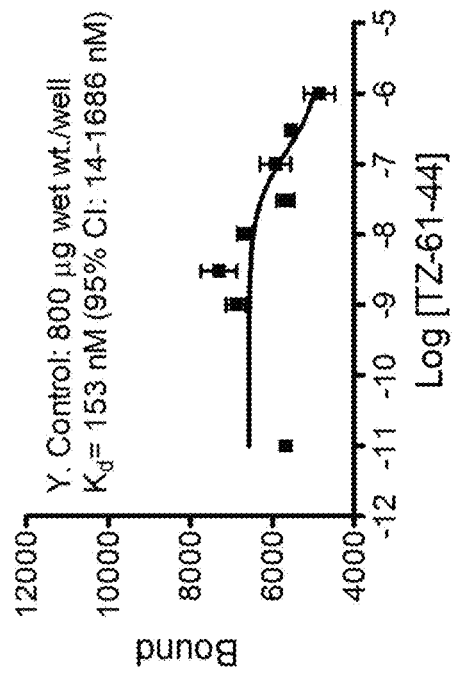
FIG. 3D

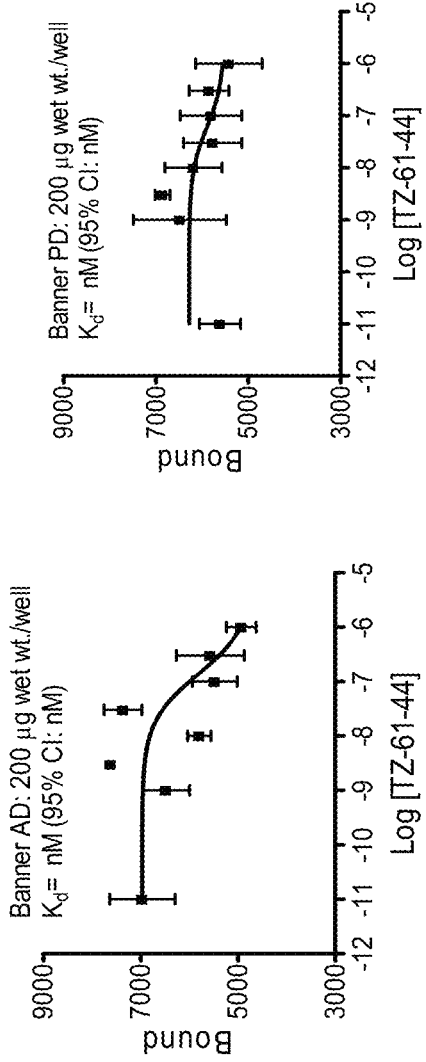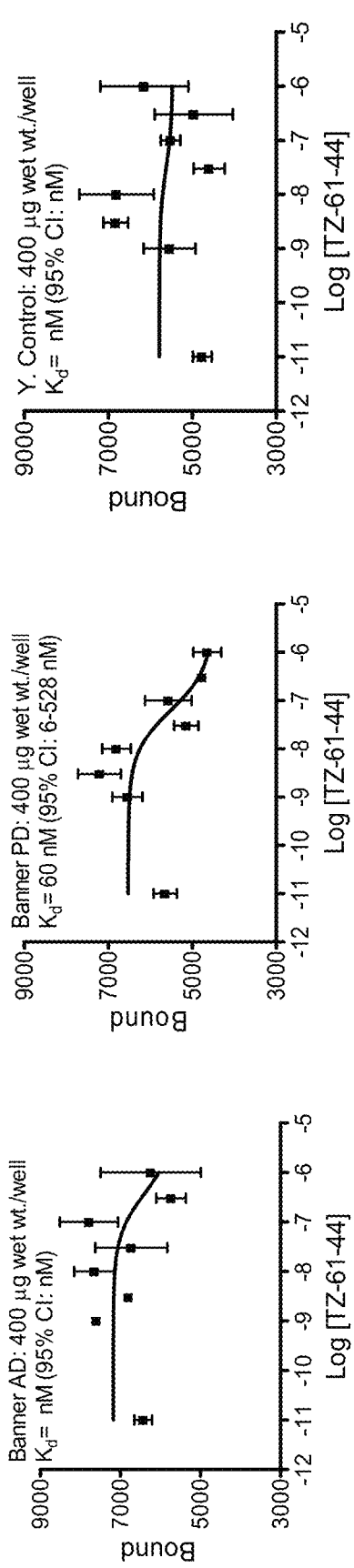

FIG. 5A
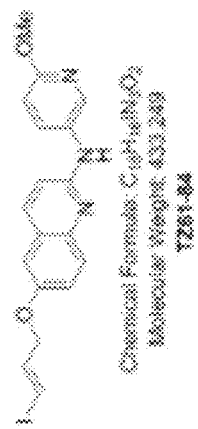
TG-1-90B
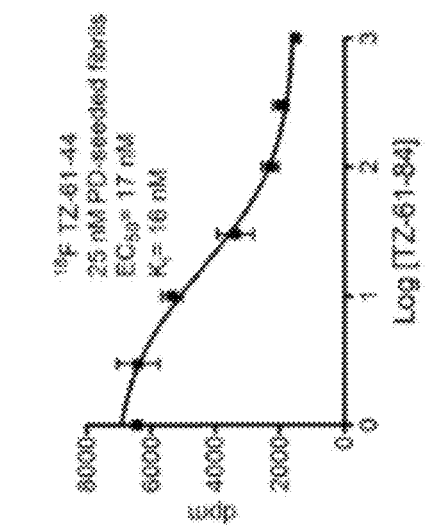
¹⁸F TZ-61-44
25 nM PD-seeded fibrils
$EC_{50}$ = 31 nM
$K_i$ = 29 nM
FIG. 5B
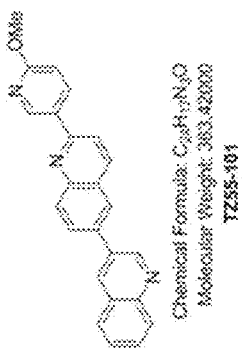
TZ55-101
Chemical Formula: C₂₅H₂₂N₂O
Molecular Weight: 383.42000
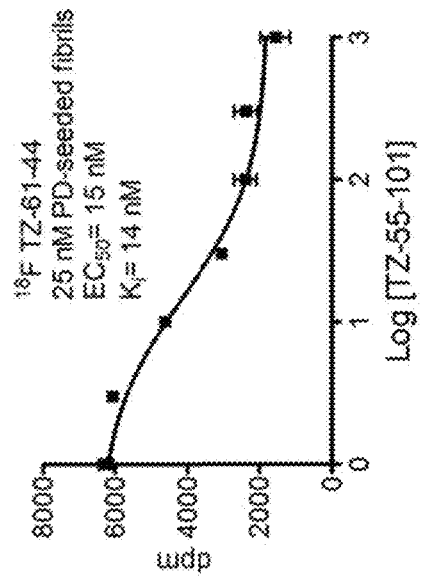
¹⁸F TZ-61-44
25 nM PD-seeded fibrils
$EC_{50}$ = 15 nM
$K_i$ = 14 nM
FIG. 5C
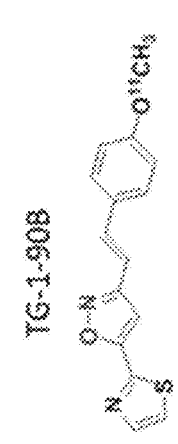
TZ61-44
Chemical Formula: C₂₆H₂₄N₂O
Molecular Weight: 433.000
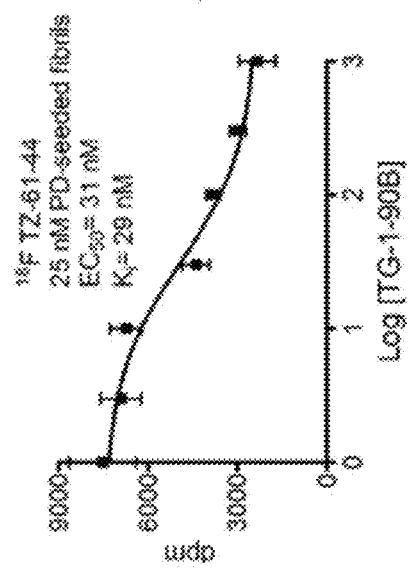
¹⁸F TZ-61-44
25 nM PD-seeded fibrils
$EC_{50}$ = 17 nM
$K_i$ = 16 nM FIG. 5D
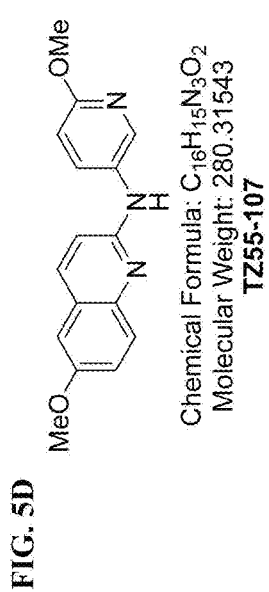
FIG. 5E
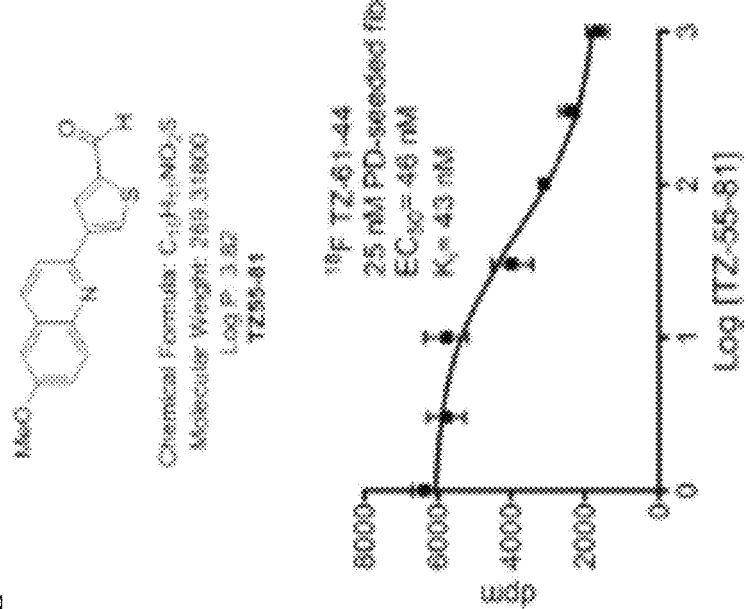
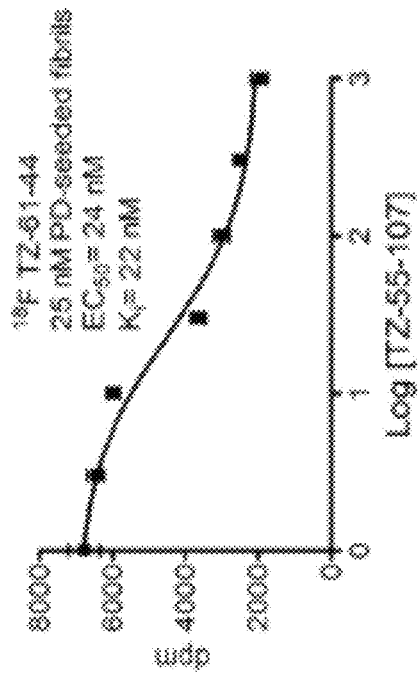

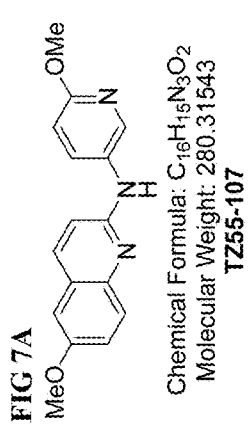
FIG 7A
Chemical Formula: $C_{16}H_{15}N_3O_2$
Molecular Weight: 280.31543
TZ55-107
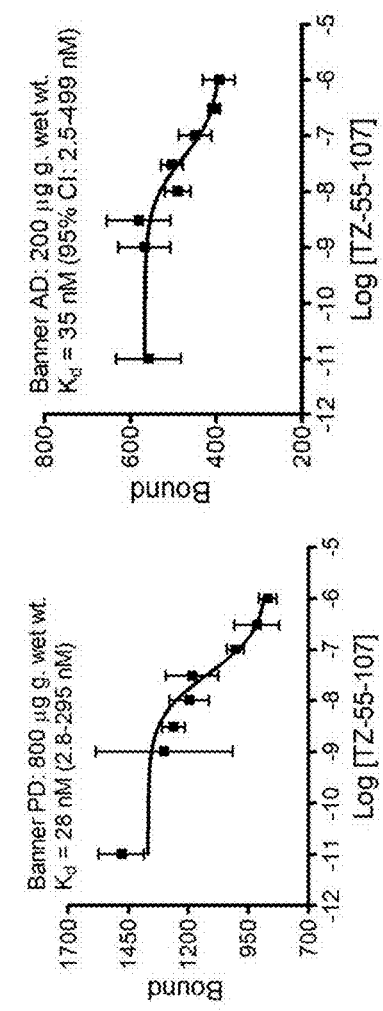
FIG. 7B
FIG. 7C
FIG. 7D
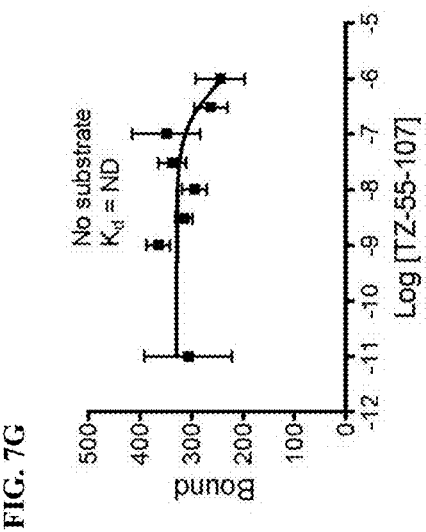
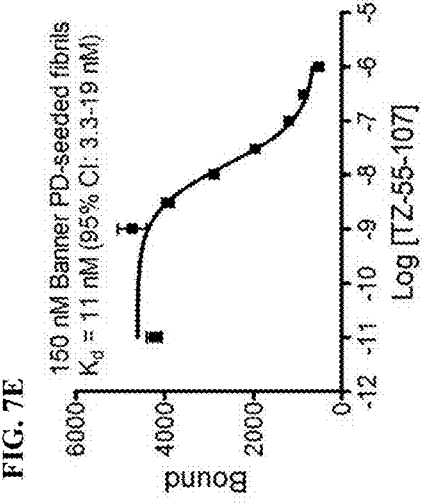
FIG. 7E
FIG. 7F
FIG. 7G

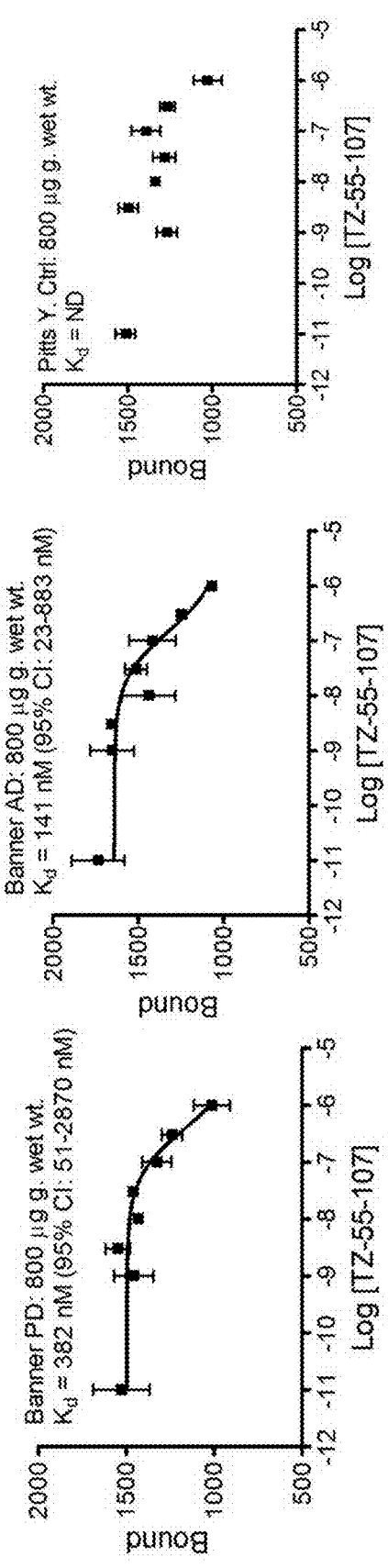
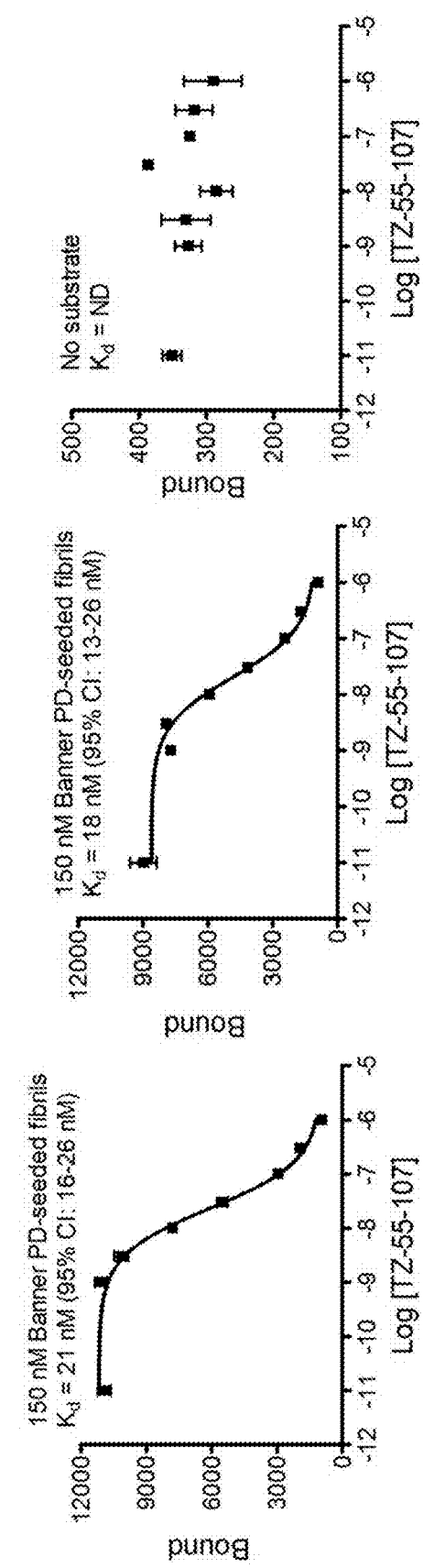
FIG. 9A FIG. 9B FIG. 9C FIG. 9D FIG. 9E FIG. 9F

Tg-1-90-B PD Fibrils Duplicate

FIG. 12A

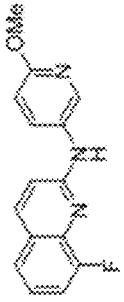

TZ64-013
Chemical Formula: C₁₆H₁₃FN₂O
Molecular Weight: 269.2794

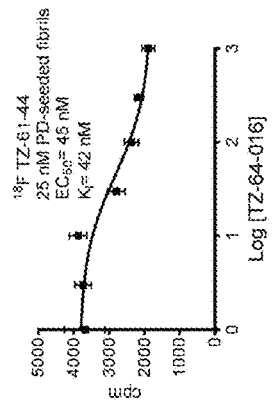

¹⁸F TZ-61-44
25 nM PD-seeded fibrils
EC₅₀= 29 nM
K_i= 27 nM

FIG. 12B

TZ64-015
Chemical Formula: C₁₆H₁₃FN₂O
Molecular Weight: 269.2794

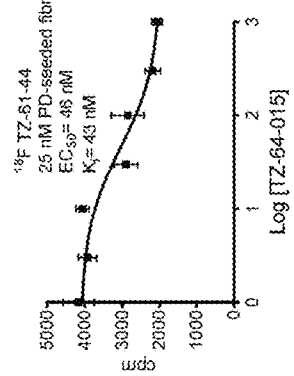

¹⁸F TZ-61-44
25 nM PD-seeded fibrils
EC₅₀= 46 nM
K_i= 43 nM

FIG. 12C

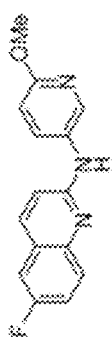

TZ64-016
Chemical Formula: C₁₆H₁₃FN₂O
Molecular Weight: 269.2794

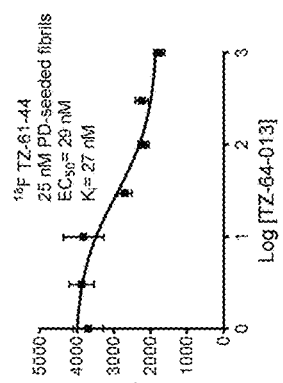

¹⁸F TZ-61-44
25 nM PD-seeded fibrils
EC₅₀= 45 nM
K_i= 42 nM

FIG. 12D

TZ64-018
Chemical Formula: C₁₇H₁₅NO₂S
Molecular Weight: 283.3450

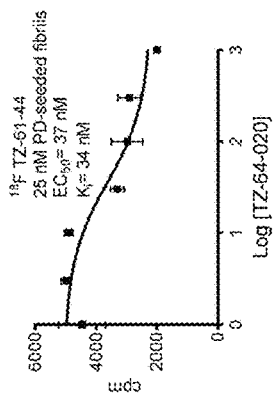

¹⁸F TZ-61-44
25 nM PD-seeded fibrils
EC₅₀= 127 nM
K_i= 119 nM

FIG. 12E

TZ64-019
Chemical Formula: C₁₇H₁₅NO₃
Molecular Weight: 253.2570

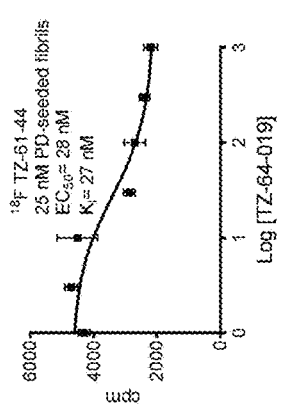

¹⁸F TZ-61-44
25 nM PD-seeded fibrils
EC₅₀= 28 nM
K_i= 27 nM

FIG. 12F

TZ64-020
Chemical Formula: C₁₇H₁₄N₂OS
Molecular Weight: 266.3180

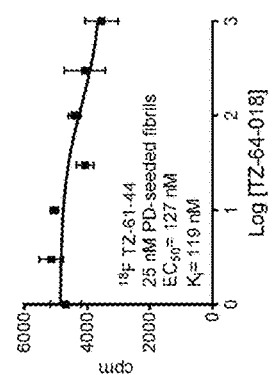

¹⁸F TZ-61-44
25 nM PD-seeded fibrils
EC₅₀= 37 nM
K_i= 34 nM

FIG. 13A 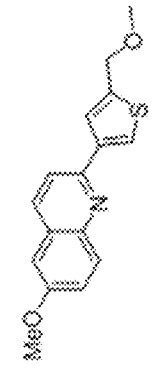 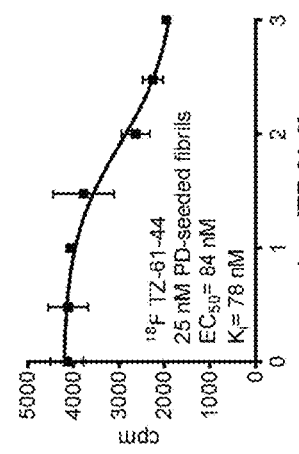
FIG. 13B 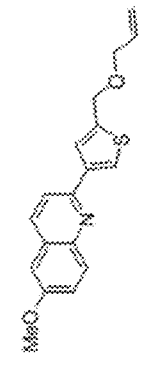 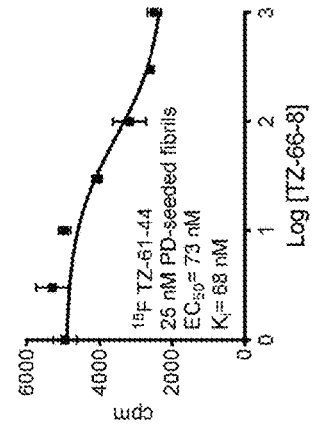
FIG. 13C 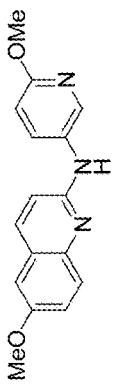 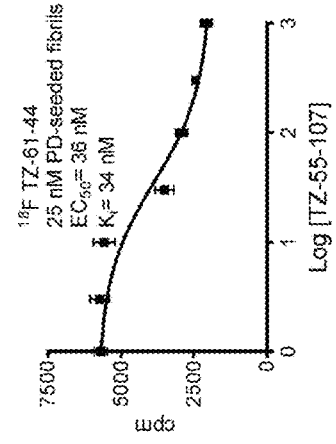
FIG. 13D 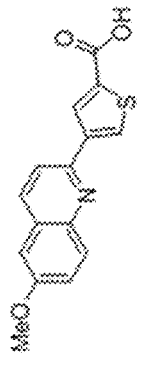 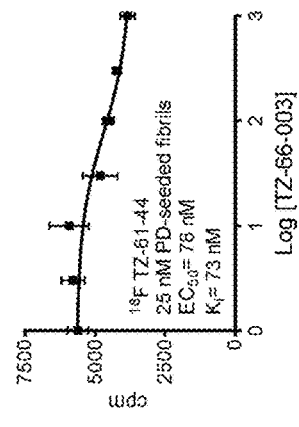

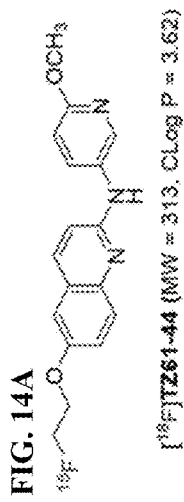
FIG. 14A
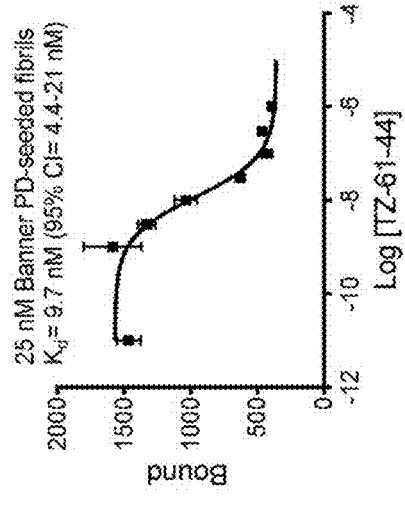
FIG. 14B
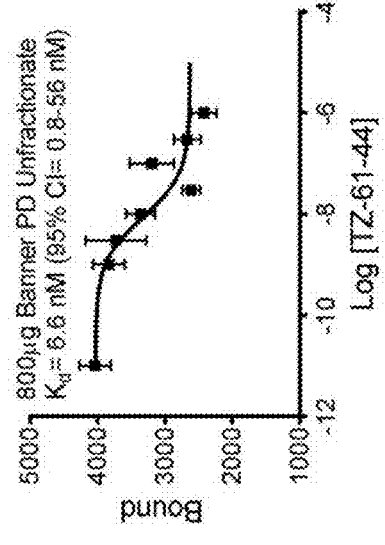
FIG. 14C
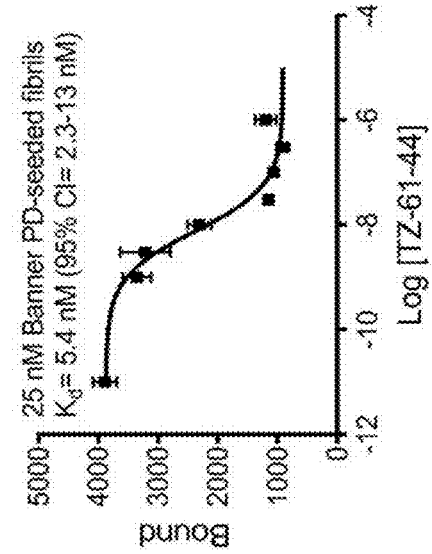
FIG. 14D
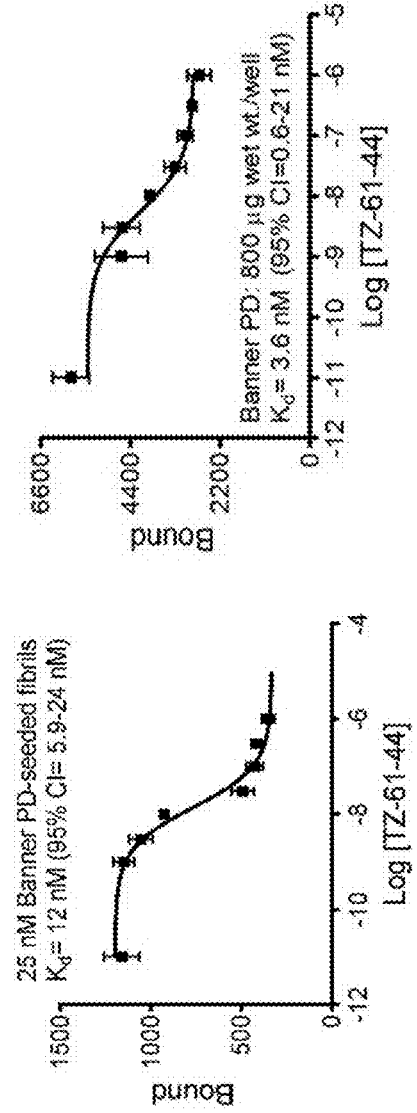
FIG. 14E
FIG. 14F

ALPHA-SYNUCLEIN LIGANDS

CROSS-REFERENCE TO RELATED APPLICATIONS

This application claims benefit of U.S. provisional application Ser. No. 62/632,352, filed Feb. 19, 2018, the entire disclosure of which is incorporated herein by reference.

FIELD OF THE INVENTION

The present invention generally relates to various compounds that are useful as α-synuclein ligands. The invention further relates to methods of using these compounds and their radiolabeled analogs for the detection of synucleinopathies, including Parkinson's disease (PD).

BACKGROUND OF THE INVENTION

Neurodegenerative diseases such as Alzheimer's disease, Parkinson's disease (PD), Huntington's disease, amyotrophic lateral sclerosis and prion diseases are debilitating diseases which affect cognition and/or muscle control. These diseases are a subset of protein misfolding diseases. Protein folding is an essential process for protein function in all organisms, and conditions that disrupt protein folding present a threat to cell viability. In some cases, the disease arises because a specific protein is no longer functional when adopting a misfolded state. In other diseases, the pathological state originates because misfolding occurs concomitantly with aggregation, and the underlying aggregates are detrimental.

Even though neurodegenerative diseases such as Alzheimer's and Parkinson's are caused by different proteins, both involve the accumulation of insoluble fibrous protein deposits, called amyloids. For example, Parkinson's Disease (PD), Dementia with Lewy Bodies (DLB), and multiple system atrophy (MSA), which are collectively referred to as "synucleinopathies," have been linked to the accumulation of aggregated forms of the α-synuclein protein in neurons in the brain. As the primary neuropathologic change of PD, the degeneration of dopaminergic neurons occurs in the substantia nigra, as well as Lewy bodies (LB) and Lewy neurites (LN). To date, the pathogenic mechanism of PD has not been fully discovered.

α-Synuclein is a presynaptic terminal protein that consists of 140-amino acid protein that plays an important function in the central nervous system including synaptic vesicle recycling and synthesis, vesicular storage, and neurotransmitter release. It is specifically upregulated in a discrete population of presynaptic terminals of the brain during acquisition-related synaptic rearrangement. α-Synuclein naturally exists in a highly soluble, unfolded state. Evidence suggests that filamentous aggregates of α-synuclein accumulate at the pre-synaptic membrane and trigger synapse dysfunction and neuronal cell death in synucleinopathies, and may be the cause of Parkinson's and DLB. α-Synuclein aggregation has been identified by antibody-immunohistological studies as the major component of Lewy bodies, which are microscopic protein deposits in deteriorating nerve cells. Accumulation of misfolded, fibrillar α-synuclein in Lewy bodies (LB) and Lewy neurites (LN) is considered a hallmark of PD.

The diagnosis of PD is mainly based on the clinical symptoms such as rest tremor, bradykinesia, and rigidity. The current treatment for PD is to slow the disease progression and minimize the disease symptoms in the patients. Therefore, a method of diagnosing PD in the very early stage can greatly help the physicians to design the therapy accordingly, and to slow the disease progression.

There remains a need for improved diagnostic methods for identifying aggregations of misfolded proteins, including α-synuclein for early detection and ongoing monitoring of PD in subjects.

SUMMARY OF THE INVENTION

In various aspects, the present invention is directed to compounds that function as ligands for α-synuclein as well as radiolabeled analogs of these compounds that are useful for diagnosing or monitoring a synucleinopathy in a subject. For example, ligands for α-synuclein of the present invention include compounds of Formulas (I-a) and (I-b), and pharmaceutically acceptable salts thereof:

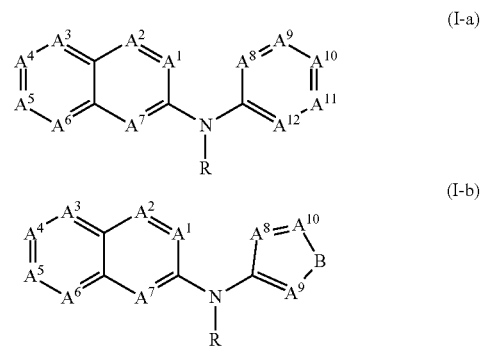

wherein each R is hydrogen, substituted or unsubstituted hydrocarbyl; each $A^1$ is independently C—$R^1$ or nitrogen; each $A^2$ is independently C—$R^2$ or nitrogen; each $A^3$ is independently C—$R^3$ or nitrogen; each $A^4$ is independently C—$R^4$ or nitrogen; each $A^5$ is independently C—$R^5$ or nitrogen; each $A^6$ is independently C—$R^6$ or nitrogen; each $A^7$ is independently C—$R^7$ or nitrogen; each $A^8$ is independently C—$R^8$ or nitrogen; each $A^9$ is independently C—$R^9$ or nitrogen; each $A^{10}$ is independently C—$R^{10}$ or nitrogen; each $A^{11}$ is independently C—$R^{11}$ or nitrogen; each $A^{12}$ is independently C—$R^{12}$ or nitrogen; B is sulfur or oxygen; and each $R^1$, $R^2$, $R^3$, $R^4$, $R^5$, $R^6$, $R^7$, $R^8$, $R^9$, $R^{10}$, $R^{11}$, and $R^{12}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted carboxylate, substituted or unsubstituted alkenyloxy, substituted or unsubstituted amino, substituted or unsubstituted thiourea, or substituted or unsubstituted amido.

In other aspects, ligands for α-synuclein of the present invention include compounds of Formula II and pharmaceutically acceptable salts thereof:

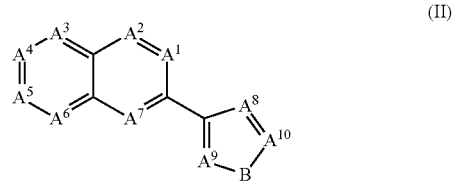

wherein $A^1$ is C—$R^1$ or nitrogen; $A^2$ is C—$R^2$ or nitrogen; $A^3$ is C—$R^3$ or nitrogen; $A^4$ is C—$R^4$ or nitrogen; $A^5$ is C—$R^5$ or nitrogen; $A^6$ is C—$R^6$ or nitrogen; $A^7$ is C—$R^7$ or nitrogen; $A^8$ is C—$R^8$ or nitrogen; $A^9$ is C—$R^9$ or nitrogen; $A^{10}$ is C—$R^{10}$ or nitrogen; B is sulfur or oxygen; and each $R^1$, $R^2$, $R^3$, $R^4$, $R^5$, $R^6$, $R^7$, $R^8$, $R^9$, and $R^{10}$ is independently hydrogen, nitro, halo, hydroxy, carboxyl, substituted or unsubstituted hydrocarbyl, substituted or unsubstituted alkyl, substituted or unsubstituted aryl or heteroaryl, substituted or unsubstituted fused aryl or heteroaryl, substituted or unsubstituted alkoxy, substituted or unsubstituted alkenyloxy, substituted or unsubstituted carboxylate, substituted or unsubstituted amino, substituted or unsubstituted thiourea, or substituted or unsubstituted amido.

In further aspects, ligands for α-synuclein of the present invention include compounds of Formula III and pharmaceutically acceptable salts thereof:

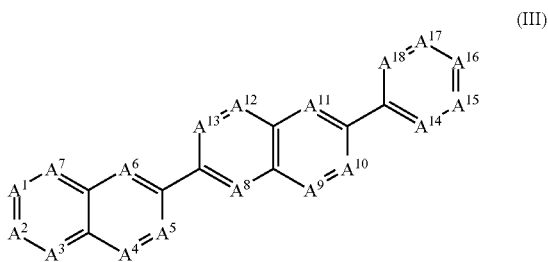

(III)

wherein $A^1$ is C—$R^1$ or nitrogen; $A^2$ is C—$R^2$ or nitrogen; $A^3$ is C—$R^3$ or nitrogen; $A^4$ is C—$R^4$ or nitrogen; $A^5$ is C—$R^5$ or nitrogen; $A^6$ is C—$R^6$ or nitrogen; $A^7$ is C—$R^7$ or nitrogen; $A^8$ is C—$R^8$ or nitrogen; $A^9$ is C—$R^9$ or nitrogen; $A^{10}$ is C—$R^{10}$ or nitrogen; $A^{11}$ is C—$R^{11}$ or nitrogen; $A^{12}$ is C—$R^{12}$ or nitrogen; $A^{13}$ is C—$R^{13}$ or nitrogen, $A^{14}$ is C—$R^{14}$ or nitrogen, $A^{15}$ is C—$R^{15}$ or nitrogen, $A^{16}$ is C—$R^{16}$ or nitrogen, $A^{17}$ is C—$R^{17}$ or nitrogen, $A^{18}$ is C—$R^{18}$ or nitrogen; and each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted carboxylate, substituted or unsubstituted alkenyloxy, substituted or unsubstituted amino, substituted or unsubstituted thiourea, or substituted or unsubstituted amido.

Further aspects of the present invention are directed to compounds of Formulas (I-a), (I-b), (II) and (III) that are radiolabeled, for example, with an isotope useful for positron emission tomography. In other aspects, the present invention is directed to methods for diagnosing or monitoring a synucleinopathy in a subject comprising administering a radiolabeled compound of Formulas (I-a), (I-b), (II) or (III) or a pharmaceutically acceptable salt thereof to the subject; and imaging the subject's brain by positron emission tomography.

Other objects and features will be in part apparent and in part pointed out hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a plot of a homologous competition binding assay of [$^{18}$F]TZ61-44 with 400 μg wet wt./well of Banner AD. Specific activity: 1015 Ci/mmol, hot concentration: 2 nM, 10% counts: 14800 cpm.

FIG. 2B is a plot of a homologous competition binding assay of [$^{18}$F]TZ61-44 with 800 μg wet wt./well of Banner PD. Specific activity: 1015 Ci/mmol, hot concentration: 2 nM, 10% counts: 14800 cpm. $B_{max}$ was 38 pmol/g. wet wt (47.6 pmol/nmol).

FIG. 2C is a plot of a homologous competition binding assay of [$^{18}$F]TZ61-44 with 800 μg wet wt./well of nonspecific substrate. Specific activity: 1015 Ci/mmol, hot concentration: 2 nM, 10% counts: 14800 cpm.

FIG. 2D is a plot of a homologous competition binding assay of [$^{18}$F]TZ61-44 without a substrate. Specific activity: 1015 Ci/mmol, hot concentration: 2 nM, 10% counts: 14800 cpm.

FIG. 3A is a plot of a homologous competition binding assay of [$^{18}$F]TZ61-44 with 800 μg wet wt./well Banner AD. Specific activity: 3277 Ci/mmol, hot concentration: 2 nM, 10% counts: 37000 cpm. $B_{max}$ is 185 pmol/nmol.

FIG. 3B is a plot of a homologous competition binding assay of [$^{18}$F]TZ61-44 with 800 μg wet wt./well Banner PD. Specific activity: 3277 Ci/mmol, hot concentration: 2 nM, 10% counts: 37000 cpm. $B_{max}$: 51 pmol/nmol.

FIG. 3C is a plot of a homologous competition binding assay of [$^{18}$F]TZ61-44 with 800 μg wet wt./well of a non-specific substrate. Specific activity: 3277 Ci/mmol, hot concentration: 2 nM, 10% counts: 37000 cpm. $B_{max}$: 323 pmol/nmol.

FIG. 3D is a plot of a homologous competition binding assay of [$^{18}$F]TZ61-44 without any substrate. Specific activity: 3277 Ci/mmol, hot concentration: 2 nM, 10% counts: 37000 cpm.

FIG. 4A is a plot of a homologous competition binding assay of [$^{18}$F]TZ61-44 with 200 μg wet wt./well Banner AD. Specific activity: 5203 Ci/mmol, hot concentration: 2 nM, 10% counts: 54000 cpm.

FIG. 4B is a plot of a homologous competition binding assay of [$^{18}$F]TZ61-44 with 200 μg wet wt./well Banner PD. Specific activity: 5203 Ci/mmol, hot concentration: 2 nM, 10% counts: 54000 cpm.

FIG. 4C is a plot of a homologous competition binding assay of [$^{18}$F]TZ61-44 with 200 μg wet wt./well of a nonspecific control substrate. Specific activity: 5203 Ci/mmol, hot concentration: 2 nM, 10% counts: 54000 cpm.

FIG. 4D is a plot of a homologous competition binding assay of [$^{18}$F]TZ61-44 with 400 μg wet wt./well Banner AD. Specific activity: 5203 Ci/mmol, hot concentration: 2 nM, 10% counts: 54000 cpm.

FIG. 4E is a plot of a homologous competition binding assay of [$^{18}$F]TZ61-44 with 400 μg wet wt./well Banner PD. Specific activity: 5203 Ci/mmol, hot concentration: 2 nM, 10% counts: 54000 cpm.

FIG. 4F is a plot of a homologous competition binding assay of [$^{18}$F]TZ61-44 with 400 μg wet wt./well of a nonspecific control substrate. Specific activity: 5203 Ci/mmol, hot concentration: 2 nM, 10% counts: 54000 cpm.

FIG. 5A depicts the structure of Tg-1-90B and a plot of a heterologous competition binding assay of TG-1-90B in the presence of the radioligand [$^{18}$F]TZ61-44 and 25 nM PD-seeded fibrils. Specific activity: 1586 Ci/mmol, hot concentration: 2 nM, 10% counts: 18650 cpm.

FIG. 5B depicts the structure of TZ55-101 and a plot of a heterologous competition binding assay of TZ55-101 in the presence of the radioligand [$^{18}$F]TZ61-44 and 25 nM PD-seeded fibrils. Specific activity: 1586 Ci/mmol, hot concentration: 2 nM, 10% counts: 18650 cpm.

FIG. 5C depicts the structure of TZ61-84 and a plot of a heterologous competition binding assay of TZ61-84 in the presence of the radioligand [$^{18}$F]TZ61-44 and 25 nM PD-seeded fibrils. Specific activity: 1586 Ci/mmol, hot concentration: 2 nM, 10% counts: 18650 cpm.

FIG. 5D depicts the structure of TZ55-107 and a plot of a heterologous competition binding assay of TZ55-107 in the presence of the radioligand [$^{18}$F]TZ61-44 and 25 nM PD-seeded fibrils. Specific activity: 1586 Ci/mmol, hot concentration: 2 nM, 10% counts: 18650 cpm.

FIG. 5E depicts the structure of TZ55-81 and a plot of a heterologous competition binding assay of TZ55-81 in the presence of the radioligand [$^{18}$F]TZ61-44 and 25 nM PD-seeded fibrils. Specific activity: 1586 Ci/mmol, hot concentration: 2 nM, 10% counts: 18650 cpm.

FIG. 7A depicts the structure of [$^{11}$C] TZ55-107 and its molecular weight.

FIG. 7B is a plot of a homologous competition binding assay of [$^{11}$C] TZ55-107 with 800 µg wet wt./well Banner PD. Specific activity: 646 Ci/mmol, hot concentration: 3.8 nM.

FIG. 7C is a plot of a homologous competition binding assay of [$^{11}$C] TZ55-107 with 200 µg wet wt./well Banner AD. Specific activity: 646 Ci/mmol, hot concentration: 3.8 nM.

FIG. 7D is a plot of a homologous competition binding assay of [$^{11}$C]TZ55-107 with 800 µg wet wt./well of a nonspecific substrate. Specific activity: 646 Ci/mmol, hot concentration: 3.8 nM.

FIG. 7E is a plot of a homologous competition binding assay of [$^{11}$C] TZ55-107 with 150 nM Banner PD-seeded fibrils. Specific activity: 646 Ci/mmol, hot concentration: 3.8 nM.

FIG. 7F is a plot of a homologous competition binding assay of [$^{11}$C] TZ55-107 with 150 nM Aβ fibrils. Specific activity: 646 Ci/mmol, hot concentration: 3.8 nM.

FIG. 7G is a plot of a homologous competition binding assay of [$^{11}$C] TZ55-107 without a substrate. Specific activity: 646 Ci/mmol, hot concentration: 3.8 nM.

FIG. 9A is a plot of a homologous competition binding assay of [$^{11}$C] TZ55-107 with 800 µg wet wt. Banner PD. Specific activity: 1014 Ci/mmol, hot concentration 2.5 nM.

FIG. 9B is a plot of a homologous competition binding assay of [$^{11}$C] TZ55-107 with 800 µg wet wt. Banner AD. Specific activity: 1014 Ci/mmol, hot concentration 2.5 nM.

FIG. 9C is a plot of a homologous competition binding assay of [$^{11}$C] TZ55-107 with 800 µg wet wt. of a nonspecific substrate. Specific activity: 1014 Ci/mmol, hot concentration 2.5 nM.

FIG. 9D is a plot of a homologous competition binding assay of [$^{11}$C] TZ55-107 with 150 nM Banner PD seeded fibrils. Specific activity: 1014 Ci/mmol, hot concentration 2.5 nM.

FIG. 9E is a plot of a homologous competition binding assay of [$^{11}$C] TZ55-107 with 150 nM Banner PD seeded fibrils. Specific activity: 1014 Ci/mmol, hot concentration 2.5 nM.

FIG. 9F is a plot of a homologous competition binding assay of [$^{11}$C] TZ55-107 without a substrate. Specific activity: 1014 Ci/mmol, hot concentration 2.5 nM.

FIG. 12A depicts the structure of TZ64-013 and a plot of a heterologous competition binding assay of TZ64-013 in the presence of the radioligand [$^{18}$F]TZ61-44 and 25 nM PD-seeded fibrils.

FIG. 12B depicts the structure of TZ64-015 and a plot of a heterologous competition binding assay of TZ64-015 in the presence of the radioligand [$^{18}$F]TZ61-44 and 25 nM PD-seeded fibrils.

FIG. 12C depicts the structure of TZ64-016 and a plot of a heterologous competition binding assay of TZ64-016 in the presence of the radioligand [$^{18}$F]TZ61-44 and 25 nM PD-seeded fibrils.

FIG. 12D depicts the structure of TZ64-018 and a plot of a heterologous competition binding assay of TZ64-018 in the presence of the radioligand [$^{18}$F]TZ61-44 and 25 nM PD-seeded fibrils.

FIG. 12E depicts the structure of TZ64-019 and a plot of a heterologous competition binding assay of TZ64-019 in the presence of the radioligand [$^{18}$F]TZ61-44 and 25 nM PD-seeded fibrils.

FIG. 12F depicts the structure of TZ64-020 and a plot of a heterologous competition binding assay of TZ64-020 in the presence of the radioligand [$^{18}$F]TZ61-44 and 25 nM PD-seeded fibrils.

FIG. 13A depicts the structure of TZ66-3 and a plot of a heterologous competition binding assay of TZ66-3 in the presence of the radioligand [$^{18}$F]TZ61-44 and 25 nM PD-seeded fibrils.

FIG. 13B depicts the structure of TZ66-9 and a plot of a heterologous competition binding assay of TZ66-9 in the presence of the radioligand [$^{18}$F]TZ61-44 and 25 nM PD-seeded fibrils.

FIG. 13C depicts the structure of TZ66-8 and a plot of a heterologous competition binding assay of TZ66-8 in the presence of the radioligand [$^{18}$F]TZ61-44 and 25 nM PD-seeded fibrils.

FIG. 13D depicts the structure of TZ55-107 and a plot of a heterologous competition binding assay of TZ55-107 in the presence of the radioligand [$^{18}$F]TZ61-44 and 25 nM PD-seeded fibrils.

FIG. 14A depicts the structure of [$^{18}$F]TZ61-44 and the molecular weight and Log P thereof.

FIG. 14B is a plot of a homologous competition binding assay of [$^{18}$F]TZ61-44 with 25 nM Banner PD-seeded fibrils.

FIG. 14C is a plot of a homologous competition binding assay of [$^{18}$F]TZ61-44 with 25 nM Banner PD-seeded fibrils.

FIG. 14D is a plot of a homologous competition binding assay of [$^{18}$F]TZ61-44 with 25 nM Banner PD-seeded fibrils.

FIG. 14E is a plot of a homologous competition binding assay of [$^{18}$F]TZ61-44 with 800 μg wet wt./well of Banner PD. Bmax value is 38 pmol/g (wet weight) or 47.6 pmol/nmol.

FIG. 14F is a plot of a homologous competition binding assay of [$^{18}$F]TZ61-44 with 800 μg Banner PD unfractionated.

DESCRIPTION OF THE PREFERRED EMBODIMENTS

Figure 1A:
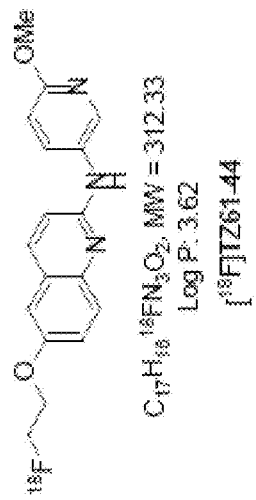
FIG. 1A depicts the structure, molecular weight and Log P of [$^{18}$F]TZ61-44.

Generally, the present invention is directed to compounds that are useful α-synuclein ligands. The compounds possess sufficient binding affinity to α-synuclein fibrils. Also, various compounds of the present invention are highly selective ligands for α-synuclein as compared to other fibrils such as Aβ-fibrils and tau fibrils. As a result, radiolabeled analogs of the compounds described herein are useful for certain diagnostic methods for synucleinopathies such as PD.

The present invention is also directed to the α-synuclein ligands that are radiolabeled with radionuclides such as carbon-11, fluorine-18 and/or iodine-125 to serve as imaging agents (e.g., positron emission tomography (PET) imaging agents) for quantifying α-synuclein protein aggregation in the brain. The in vivo quantification of α-synuclein protein aggregation in patients is useful not only for diagnosing synucleinopathies such as PD, but also for monitoring disease progression.

As noted, fibrillar α-synuclein imaging is a highly useful marker for disease progression. Thus, an α-synuclein imaging agent provides for accurate enrollment of early stage PD patients into trials of therapeutic interventions targeting disease progression. If progressive accumulation of α-synuclein within individual regions or across multiple brain regions correlates with disease progression, particularly in early and intermediate disease stages, an α-synuclein imaging agent could also greatly improve evaluation of therapeutic efficacy for candidate disease-modifying interventions.

To these ends, applicants have discovered compounds that are useful as α-synuclein ligands. In accordance with various aspects of the present invention, useful as α-synuclein ligands comprise compounds of Formulas (I-a), (I-b), (II) and (III).

In certain embodiments, the α-synuclein ligand comprises a compound of Formulas (I-a), (I-b), (II), or (III), and pharmaceutically acceptable salts thereof:

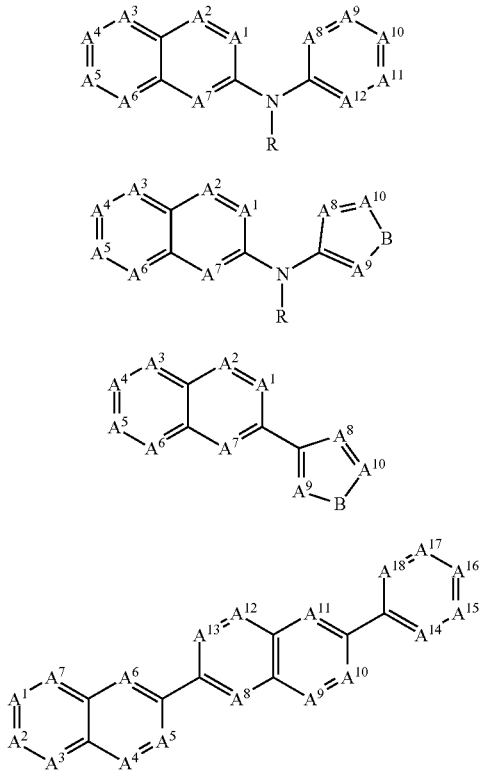

wherein each R is hydrogen, substituted or unsubstituted alkyl, substituted or unsubstituted hydrocarbyl; each $A^1$ is independently C—$R^1$ or nitrogen; each $A^2$ is independently C—$R^2$ or nitrogen; each $A^3$ is independently C—$R^3$ or nitrogen; each $A^4$ is independently C—$R^4$ or nitrogen; $A^5$ is C—$R^5$ or nitrogen; each $A^6$ is independently C—$R^6$ or nitrogen; each $A^7$ is independently C—$R^7$ or nitrogen; each $A^8$ is independently C—$R^8$ or nitrogen; each $A^9$ is independently C—$R^9$ or nitrogen; each $A^{10}$ is independently C—$R^{10}$ or nitrogen; each $A^{11}$ is independently C—$R^{11}$ or nitrogen; each $A^{12}$ is independently C—$R^{12}$ or nitrogen; each $A^{13}$ is independently C—$R^{13}$ or nitrogen, each $A^{14}$ is independently C—$R^{14}$ or nitrogen, each $A^{15}$ is independently C—$R^{15}$ or nitrogen, each $A^{16}$ is independently C—$R^{16}$ or nitrogen, each $A^{17}$ is independently C—$R^{17}$ or nitrogen, each $A^{18}$ is independently C—$R^{18}$ or nitrogen, each B is sulfur or oxygen; and each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted aryl or heteroaryl, substituted or unsubstituted fused aryl or heteroaryl, substituted or unsubstituted carboxylate, substituted or unsubstituted alkenyloxy, substituted or unsubstituted amino, substituted or unsubstituted thiourea, or substituted or unsubstituted amido.

In various embodiments, at least one of the aromatic rings of the compounds of Formulas (I-a), (I-b), (II) and (III) is a heteroaromatic ring and more particularly, a nitrogen-containing heteroaromatic ring. Accordingly, in these embodiments, at least one, at least two, or at least three of $A^1$, $A^2$, $A^3$, $A^4$, $A^5$, $A^6$, $A^7$, $A^8$, $A^9$, $A^{10}$, $A^{11}$, $A^2$, $A^{13}$, $A^{14}$, $A^{15}$, $A^{16}$, $A^{17}$, and $A^{18}$ is nitrogen.

In various embodiments, each R of Formulas (I-a) or (I-b) is independently hydrogen or a substituted or unsubstituted $C_1$ to $C_6$ alkyl. For example, each R can independently be hydrogen or a methyl. In certain embodiments, each R is hydrogen.

In various embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted carboxylate, substituted or unsubstituted aryl or heteroaryl, substituted or unsubstituted fused aryl or heteroaryl, substituted or unsubstituted alkenyloxy, substituted or unsubstituted amino, substituted or unsubstituted thiourea, or substituted or unsubstituted amido.

For example, each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ can be hydrogen, halo, nitro, cyano, substituted or unsubstituted $C_1$ to $C_6$ alkyl, substituted or unsubstituted $C_1$ to $C_6$ alkoxy, substituted or unsubstituted $C_1$ to $C_6$ alkenyloxy, substituted or unsubstituted amino, substituted or unsubstituted amido, substituted or unsubstituted thiourea, or substituted or unsubstituted carboxylate, substituted or unsubstituted aryl or heteroaryl, substituted or unsubstituted fused aryl or fused heteroaryl, or a substituted or unsubstituted heterocyclic ring.

In some embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ can be hydrogen, halo, nitro, hydroxyl, cyano, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, $C_1$ to $C_6$ aminoalkyl, amido, $C_1$ to $C_6$ alkylamido, $C_1$ to $C_6$ amidoalkyl, $C_1$ to $C_6$ alkyl-substituted thiourea, $C_1$ to $C_6$ alkyl-substituted carboxylate, $C_1$ to $C_6$ haloalkyl-substituted carboxylate, a substituted or unsubstituted aryl or heteroaryl, a substituted or unsubstituted fused aryl or heteroaryl, or a substituted or unsubstituted heterocyclic ring.

The compound of Formulas (I-a), (I-b), (II), and (III) will be described in more detail herein below.

Various α-synuclein ligands of the present invention comprise compounds of Formula (I-a) and (I-b), and pharmaceutically acceptable salts thereof:

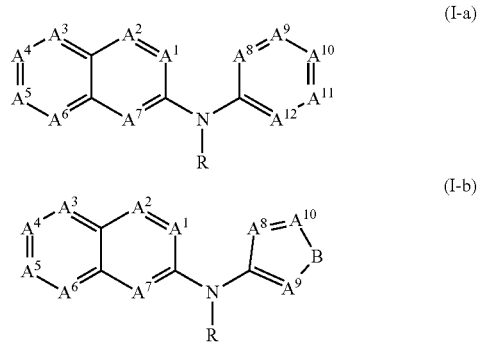

wherein each R is hydrogen, substituted or unsubstituted hydrocarbyl; each $A^1$ is independently C—$R^1$ or nitrogen; each $A^2$ is independently C—$R^2$ or nitrogen; each $A^3$ is independently C—R³ or nitrogen; each A⁴ is independently C—R⁴ or nitrogen; each A⁵ is independently C—R⁵ or nitrogen; each A⁶ is independently C—R⁶ or nitrogen; each A⁷ is independently C—R⁷ or nitrogen; each A⁸ is independently C—R⁸ or nitrogen; each A⁹ is independently C—R⁹ or nitrogen; each A¹⁰ is independently C—R¹⁰ or nitrogen; each A¹¹ is independently C—R¹¹ or nitrogen; each A¹² is independently C—R¹² or nitrogen; B is sulfur or oxygen; and each $R^1$, $R^2$, $R^3$, $R^4$, $R^5$, $R^6$, $R^7$, $R^8$, $R^9$, $R^{10}$, $R^{11}$, and $R^{12}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted carboxylate, substituted or unsubstituted alkenyloxy, substituted or unsubstituted amino, substituted or unsubstituted thiourea, or substituted or unsubstituted amido In some instances, each R can be hydrogen or a substituted or unsubstituted $C_1$-$C_{10}$ alkyl. For example, each R can be hydrogen or methyl. In various embodiments, each R is hydrogen.

In some embodiments, at least one or at least two of $A^1$, $A^2$, $A^3$, $A^4$, $A^5$, $A^6$, $A^7$ $A^8$, $A^9$, $A^{10}$, $A^{11}$, and $A^{12}$ is nitrogen. In further embodiments, at least one of $A^1$, $A^2$, $A^3$, $A^4$, $A^5$, $A^6$, and $A^7$ is nitrogen. In some embodiments, at least one of $A^8$, $A^9$, $A^{10}$, $A^{11}$, and $A^{12}$ is nitrogen. In still further embodiments, at least one of $A^2$, $A^3$, $A^4$, $A^5$, $A^6$, and $A^7$ is nitrogen. In some embodiments, $A^7$ is nitrogen. In further embodiments, at least one of $A^{11}$ and $A^{12}$ is nitrogen. For example, in some instances, $A^7$ and at least one of $A^{11}$ and $A^{12}$ is nitrogen. In some embodiments, at least two of $A^8$, $A^9$ and $A^{10}$ are nitrogen. For example, $A^7$, $A^8$ and $A^9$ can be each nitrogen. In further embodiments, the α-synuclein ligand can comprise a compound of Formula (I-a) wherein at least one of $A^2$, $A^3$, $A^4$, $A^5$, $A^6$, and $A^7$ and at least one of $A^{11}$ and $A^{12}$ are independently nitrogen. In various embodiments, the α-synuclein ligand can comprise a compound of Formula (I-b) wherein $A^7$ is nitrogen.

In some embodiments, $A^1$ is C—$R^1$, $A^8$ is C—$R^8$, $A^9$ is C—$R^9$ and/or $A^{10}$ is C—$R^{10}$. In certain embodiments, each $A^1$, $A^8$ and $A^9$ are independently C—H. In some embodiments, each $A^2$ is C—$R^2$, each $A^3$ is C—$R^3$, each $A^4$ is C—$R^4$, each $A^5$ is C—$R^5$, and/or each $A^6$ is C—$R^6$. In certain embodiments, at least one of $R^2$, $R^3$, $R^4$, $R^5$, and $R^6$ is not hydrogen. In further embodiments, each $A^{10}$ is C—$R^{10}$ wherein $R^{10}$ is not hydrogen.

In some embodiments, B is sulfur. In certain embodiments, B is oxygen. In various embodiments, B is oxygen and $A^8$ and $A^9$ are each C—H.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently hydrogen, halo, nitro, cyano, substituted or unsubstituted $C_1$ to $C_6$ alkyl, substituted or unsubstituted $C_1$ to $C_6$ alkoxy, substituted or unsubstituted $C_1$ to $C_6$ alkenyloxy, substituted or unsubstituted amino, substituted or unsubstituted amido, substituted or unsubstituted thiourea, or substituted or unsubstituted carboxylate.

For example, in further embodiments, $R^1$, $R^2$, $R^3$, $R^4$, $R^5$, $R^6$, $R^7$, $R^8$, $R^9$, $R^{10}$, $R^{11}$, and $R^{12}$ can each be independently hydrogen, halo, nitro, hydroxyl, cyano, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, $C_1$ to $C_6$ aminoalkyl, amido, $C_1$ to $C_6$ alkylamido, $C_1$ to $C_6$ amidoalkyl, $C_1$ to $C_6$ alkyl-substituted thiourea, $C_1$ to $C_6$ alkyl-substituted carboxylate, or $C_1$ to $C_6$ haloalkyl-substituted carboxylate.

In some embodiments, $R^4$ is a halogen, nitro, halo-substituted $C_1$ to $C_6$ alkenyloxy, halo-substituted $C_1$ to $C_6$ alkoxy, or methoxy. In further embodiments, $R^{10}$ is methoxy. In some instances, $R^4$ is a halogen, nitro, halo-substituted $C_1$ to $C_6$ alkenyloxy, halo-substituted $C_1$ to $C_6$ alkoxy, or methoxy and $R^{10}$ is methoxy.

In certain embodiments, each $R^1$, $R^2$, $R^3$, $R^4$, $R^5$, $R^6$, $R^7$, $R^8$, $R^9$, $R^{10}$, $R^{11}$, and $R^{12}$ is independently selected from the group consisting of hydrogen, halo, nitro, —CHO, —COCH₃, —COOH, —CO₂CH₃, —OCH₃, —OCH₂CH₂F, —OCH(CH₃)₂, —OCH₂OCH₃, —CH₂OCH₃, —CH₂OCH₂CH₂F, —NO₂, —CN, —CH₂N(CH₂CH₃)₂, —CH₂OH, —OH,

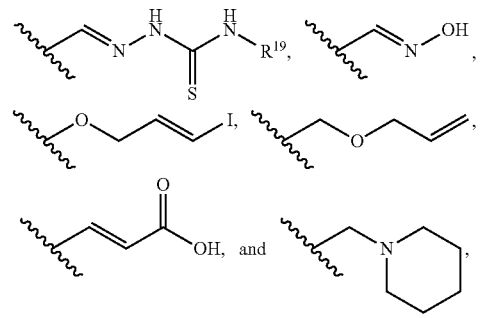

wherein $R^{19}$ is substituted or unsubstituted aryl, substituted or unsubstituted alkyl, substituted or unsubstituted alkenyl, or substituted or unsubstituted alkynyl. In some embodiments, $R^{19}$ is phenyl, $C_1$ to $C_6$ alkyl, $C_1$ to $C_6$ alkenyl, or $C_1$ to $C_6$ alkynyl.

In various embodiments, at least one of $R^2$, $R^3$, $R^4$, $R^5$, and $R^6$ is not hydrogen. In some embodiments, $R^{10}$ is not hydrogen. In other embodiments, $R^1$, $R^2$, $R^3$, $R^5$, $R^6$, $R^7$, $R^8$, and $R^9$ are hydrogen.

In some embodiments, the compound of Formulas (I-a) and (I-b) can be selected from the group consisting of:

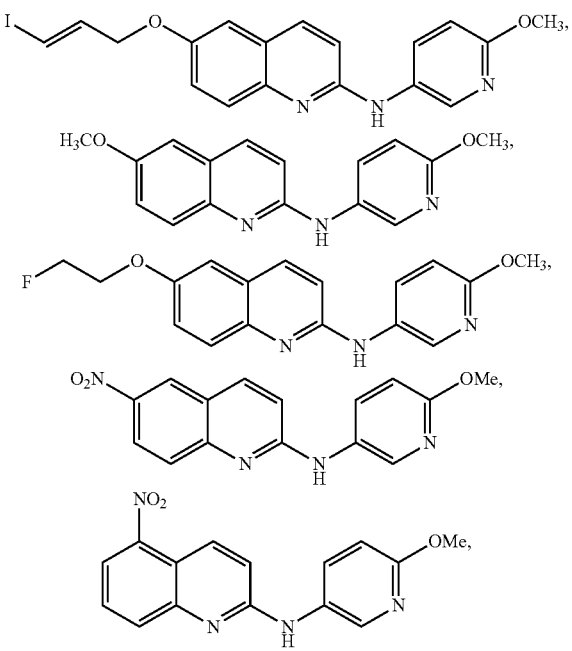

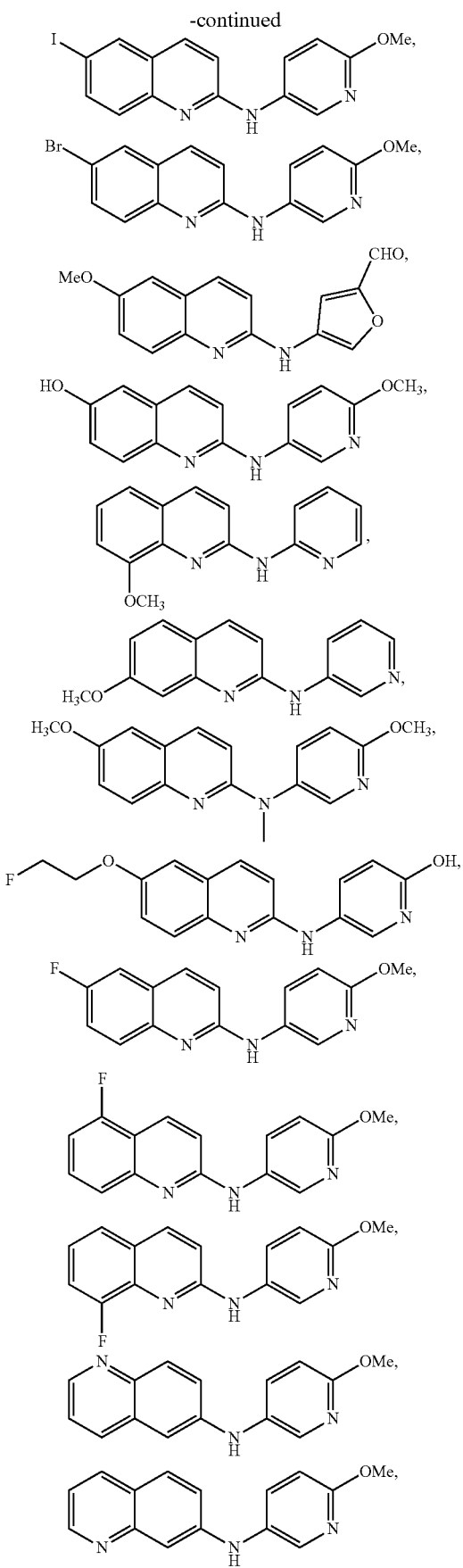

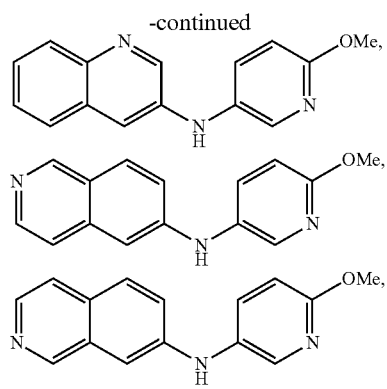

and pharmaceutically acceptable salts thereof.

Other α-synuclein ligands of the present invention comprise compounds of Formula (II) and pharmaceutically acceptable salts thereof:

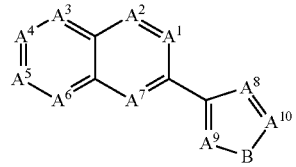

(II)

wherein $A^1$ is C—$R^1$ or nitrogen; $A^2$ is C—$R^2$ or nitrogen; $A^3$ is C—$R^3$ or nitrogen; $A^4$ is C—$R^4$ or nitrogen; $A^5$ is C—$R^5$ or nitrogen; $A^6$ is C—$R^6$ or nitrogen; $A^7$ is C—$R^7$ or nitrogen; $A^8$ is C—$R^8$ or nitrogen; $A^9$ is C—$R^9$ or nitrogen; $A^{10}$ is C—$R^{10}$ or nitrogen; B is sulfur or oxygen; and each $R^1$, $R^2$, $R^3$, $R^4$, $R^5$, $R^6$, $R^7$, $R^8$, $R^9$, and $R^{10}$ is independently hydrogen, nitro, halo, hydroxy, carboxyl, substituted or unsubstituted hydrocarbyl, substituted or unsubstituted alkyl, substituted or unsubstituted aryl or heteroaryl, substituted or unsubstituted fused aryl or heteroaryl, substituted or unsubstituted alkoxy, substituted or unsubstituted alkenyloxy, substituted or unsubstituted carboxylate, substituted or unsubstituted amino, substituted or unsubstituted thiourea, or substituted or unsubstituted amido.

In some embodiments, at least one of $A^2$, $A^3$, $A^4$, $A^5$, $A^6$ and $A^7$ is a nitrogen. In various embodiments, $A^7$ is nitrogen. In some instances, $A^1$ is C—H or C—$R^1$, $A^2$ is C—H or C—$R^2$, $A^3$ is C—H or C—$R^3$, $A^4$ is C—H or C—$R^4$, $A^5$ is C—H or C—$R^5$, and/or $A^6$ is C—H or C—$R^6$. In various embodiments, $A^4$ is C—$R^4$.

In still further embodiments, at least two of $A^8$, $A^9$ and $A^{10}$ are nitrogen. In some embodiments, at least two of $A^8$, $A^9$ and $A^{10}$ are each C—H. In various embodiments, $A^8$ and $A^9$ are either each nitrogen or each C—H. In various embodiments, $A^{10}$ is C—$R^{10}$.

Each $R^1$, $R^2$, $R^3$, $R^4$, $R^5$, $R^6$, $R^7$, $R^8$, $R^9$, and $R^{10}$ can be independently hydrogen, halo, nitro, cyano, substituted or unsubstituted $C_1$ to $C_6$ alkyl, substituted or unsubstituted $C_1$ to $C_6$ alkoxy, substituted or unsubstituted $C_1$ to $C_6$ alkenyloxy, substituted or unsubstituted amino, substituted or unsubstituted amido, substituted or unsubstituted thiourea, or substituted or unsubstituted carboxylate, substituted or unsubstituted aryl or heteroaryl, a substituted or unsubstituted fused aryl or heteroaryl, or a substituted or unsubstituted heterocyclic ring.

In some embodiments, each of $R^1$, $R^2$, $R^3$, $R^4$, $R^5$, $R^6$, $R^7$, $R^8$, $R^9$, and $R^{10}$ can be independently hydrogen, halo, nitro, hydroxyl, cyano, carboxyl, substituted or unsubstituted aryl or heteroaryl, a substituted or unsubstituted fused aryl or heteroaryl, or a substituted or unsubstituted heterocyclic ring, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, $C_1$ to $C_6$ aminoalkyl, amido, $C_1$ to $C_6$ alkylamido, $C_1$ to $C_6$ amidoalkyl, $C_1$ to $C_6$ alkyl-substituted thiourea, $C_1$ to $C_6$ alkyl-substituted carboxylate, or $C_1$ to $C_6$ haloalkyl-substituted carboxylate.

In certain embodiments, $R^4$ is hydrogen, a halo, nitro, —CHO, —COCH$_3$, —COOH, —CO$_2$CH$_3$, —OCH$_3$, —OCH$_2$CH$_2$F, —OCH(CH$_3$)$_2$, —OCH$_2$OCH$_3$, —CH$_2$OCH$_3$, —CH$_2$OCH$_2$CH$_2$F, —NO$_2$, —CN, —CH$_2$N(CH$_2$CH$_3$)$_2$, —CH$_2$OH, —OH,

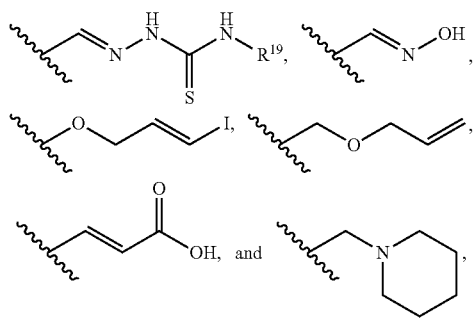

wherein $R^{19}$ is substituted or unsubstituted aryl, substituted or unsubstituted alkyl, substituted or unsubstituted alkenyl, or substituted or unsubstituted alkynyl. In some embodiments, $R^{19}$ is phenyl, $C_1$ to $C_6$ alkyl, $C_1$ to $C_6$ alkenyl, or $C_1$ to $C_6$ alkynyl. In various embodiments, $R^4$ can be —OCH$_3$, —OCH$_2$OCH$_3$, —OCH$_2$CH$_2$F, or —OCH(CH$_3$)$_2$.

In certain embodiments, $R^{19}$ is hydrogen, a halo, nitro, substituted or unsubstituted aryl or heteroaryl, a substituted or unsubstituted fused aryl or heteroaryl, —CHO, —COCH$_3$, —COOH, —CO$_2$CH$_3$, —OCH$_3$, —OCH$_2$CH$_2$F, —OCH(CH$_3$)$_2$, —OCH$_2$OCH$_3$, —CH$_2$OCH$_3$, —CH$_2$OCH$_2$CH$_2$F, —NO$_2$, —CN, —CH$_2$N(CH$_2$CH$_3$)$_2$, —CH$_2$OH, —OH,

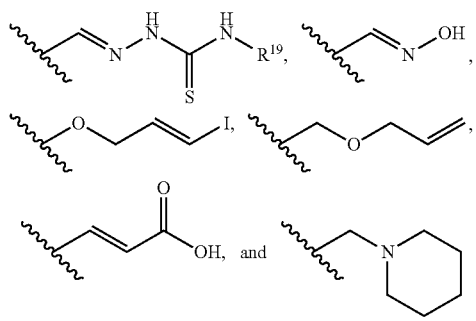

wherein $R^{19}$ is substituted or unsubstituted aryl, substituted or unsubstituted alkyl, substituted or unsubstituted alkenyl, or substituted or unsubstituted alkynyl. In some embodiments, $R^{19}$ is phenyl, $C_1$ to $C_6$ alkyl, $C_1$ to $C_6$ alkenyl, or $C_1$ to $C_6$ alkynyl.

In some embodiments, $R^{19}$ is a $C_5$ to $C_6$ aryl substituted with an alkoxy, a halo, a $C_5$ to $C_6$ heteroaryl or any combination thereof. In further embodiments, $R^{19}$ is a substituted or unsubstituted $C_5$ to $C_6$ heteroaryl. In still further embodiments, $R^{19}$ is a substituted or unsubstituted $C_9$ to $C_{10}$ fused heteroaryl.

The $C_5$ to $C_6$ heteroaryl or the $C_9$ to $C_{10}$ fused heteroaryl can each contains an N, O, or S or any combination thereof. For example, the $C_5$ to $C_6$ heteroaryl can contain a one or two nitrogens, one or two oxygens, a nitrogen and a sulfur, or a nitrogen and an oxygen. Further, the $C_9$ to $C_{10}$ fused heteraryl can contain one or two nitrogens and/or one or two oxygens.

The $C_5$ to $C_6$ heteroaryl or the $C_9$ to $C_{10}$ fused heteroaryl may be unsubstituted. Alternatively, the $C_5$ to $C_6$ heteroaryl or the $C_9$ to $C_{10}$ fused heteroaryl can be substituted with halo, nitro, hydroxyl, cyano, carboxyl, substituted or unsubstituted aryl or heteroaryl, a substituted or unsubstituted fused aryl or heteroaryl, or a substituted or unsubstituted heterocyclic ring, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, $C_1$ to $C_6$ aminoalkyl, amido, $C_1$ to $C_6$ alkylamido, $C_1$ to $C_6$ amidoalkyl, $C_1$ to $C_6$ alkyl-substituted thiourea, $C_1$ to $C_6$ alkyl-substituted carboxylate, or $C_1$ to $C_6$ haloalkyl-substituted carboxylate. For example, the $C_5$ to $C_6$ heteroaryl or the $C_9$ to $C_{10}$ fused heteroaryl may be substituted with an alkoxy (e.g., a methoxy), a halo or any combination thereof.

Accordingly, in some embodiments, $R^{10}$ is selected from the group consisting of: —CN, COOH, —COCH$_3$, —CO$_2$CH$_3$, —CH$_2$OH, —CH$_2$(CH$_2$CH$_3$)$_2$, —CH$_2$OCH$_3$, —CH$_2$OCH$_2$CH$_2$F,

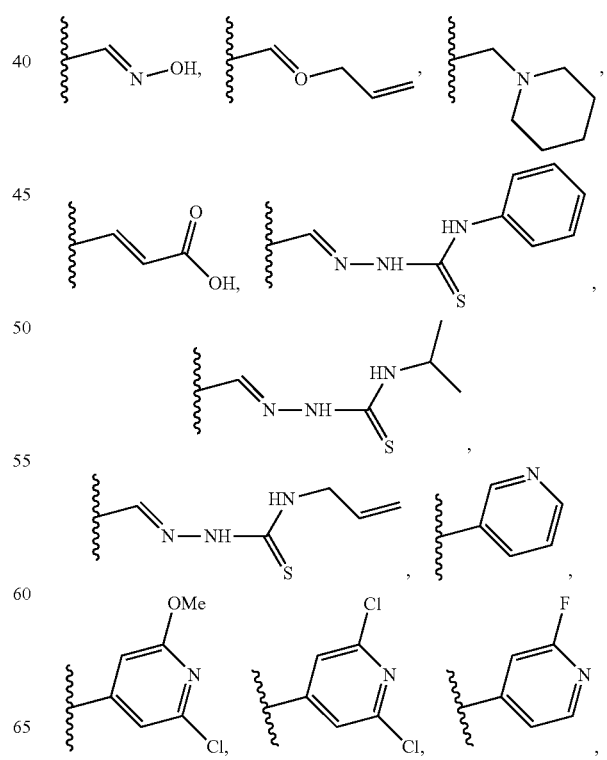

-continued

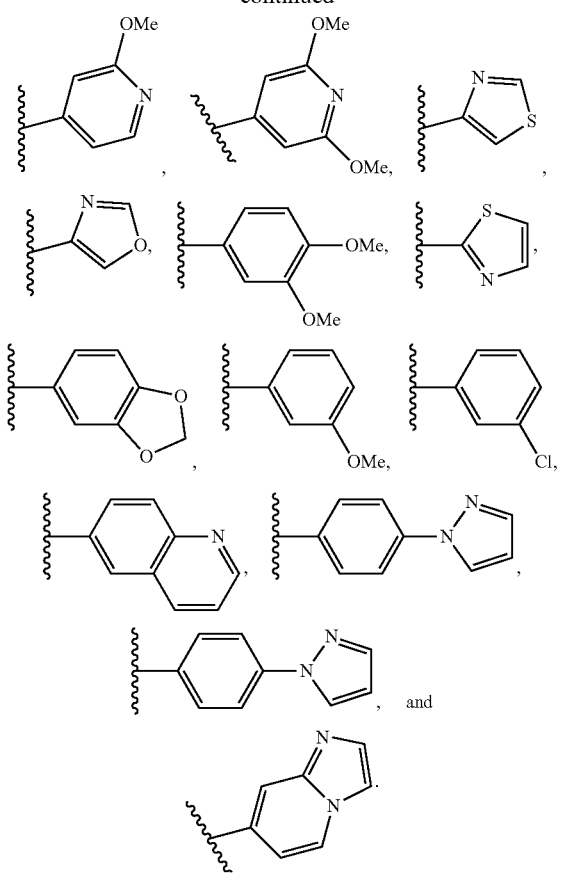

In some embodiments, each of $A^1$, $A^2$, $A^3$, $A^5$, $A^6$ are C—H. In still further embodiments, each of $A^1$, $A^2$, $A^3$, $A^5$, $A^6$ are C—H and $A^8$ and $A^9$ are each C—H or each nitrogen.

B can be oxygen or sulfur. In various embodiments, B is oxygen, and $A^8$ and $A^9$ are either each nitrogen or C—H. In some embodiments, B is sulfur and $A^8$ and $A^9$ are each C—H.

In various embodiments, the compound of Formula (II) can be selected from the group consisting of:

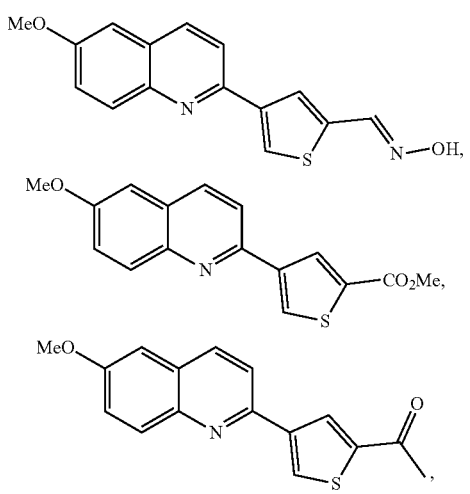

-continued

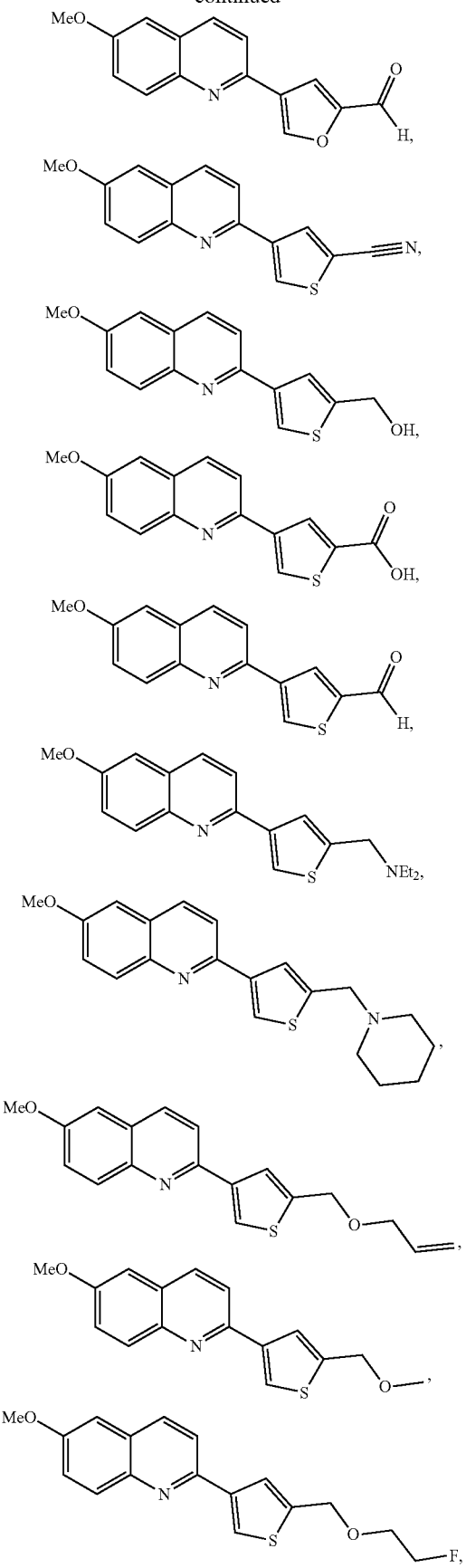

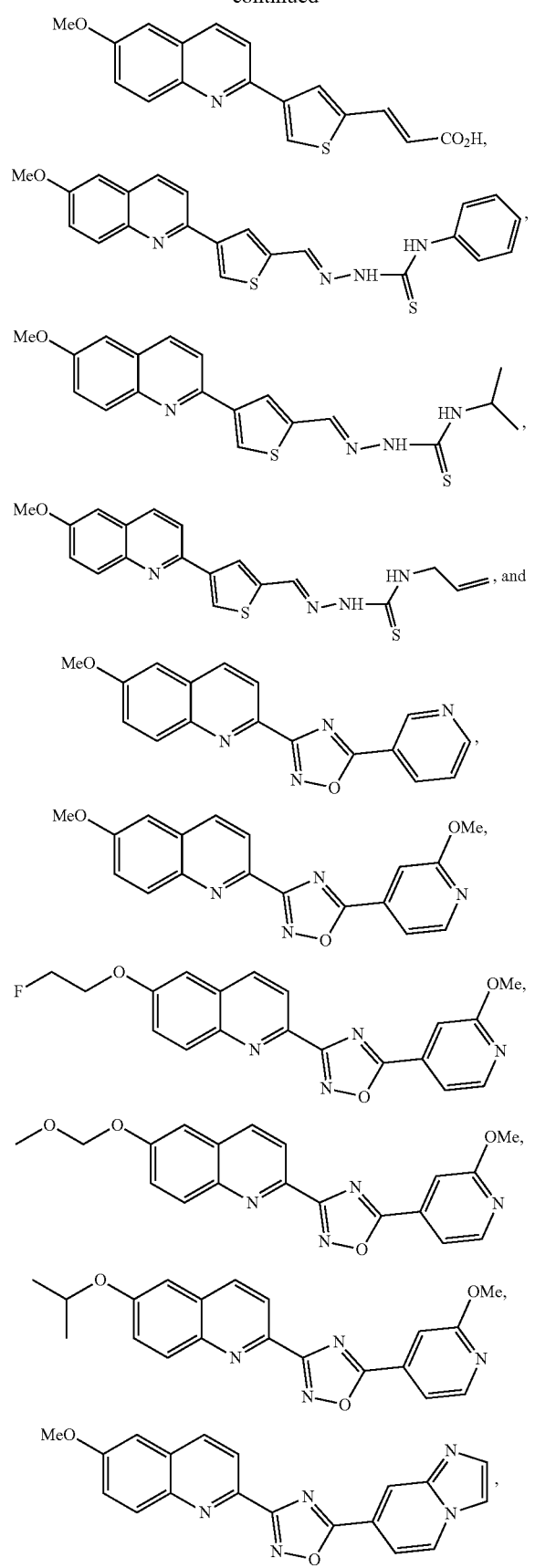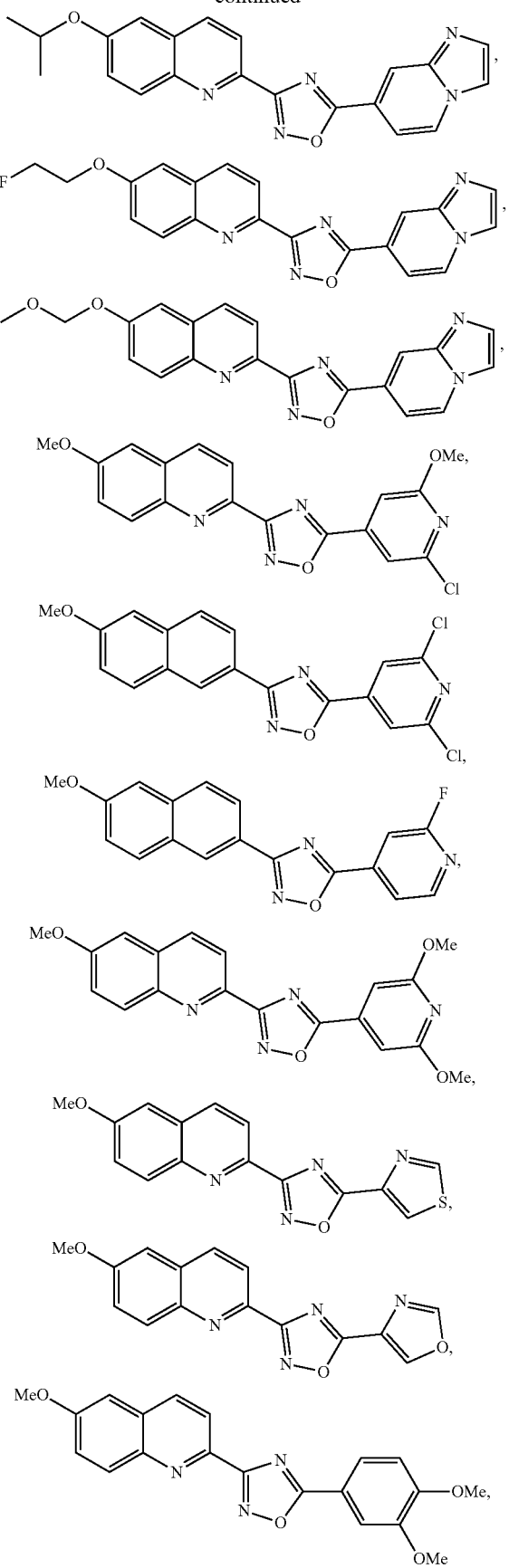

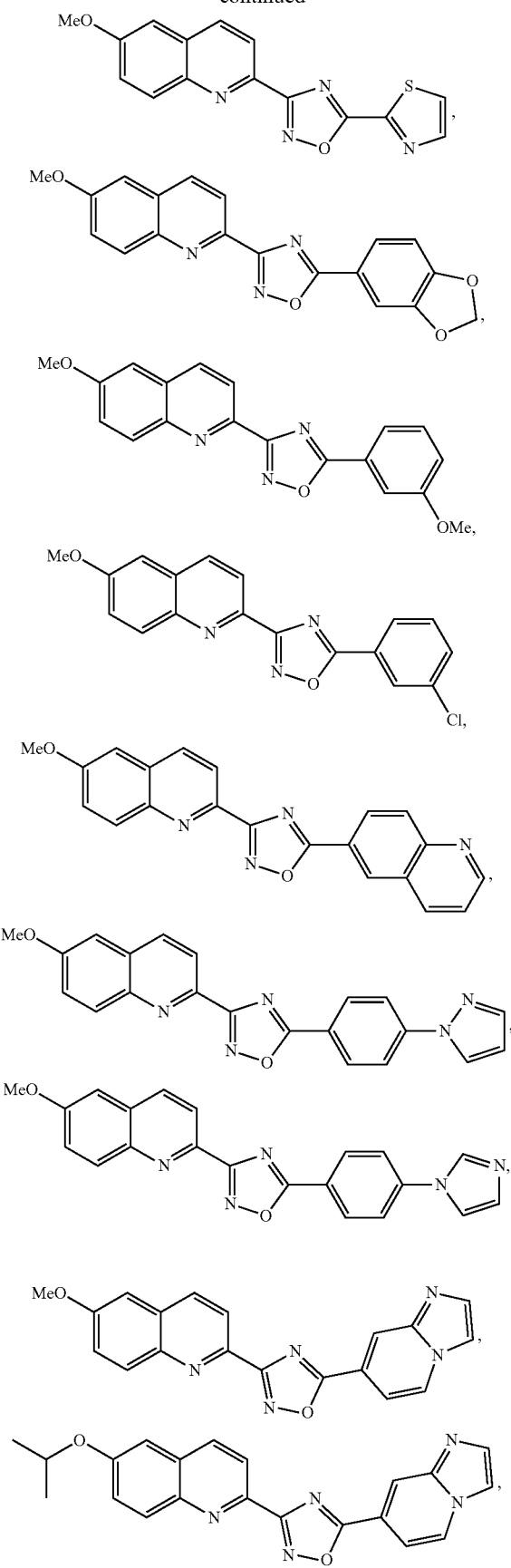

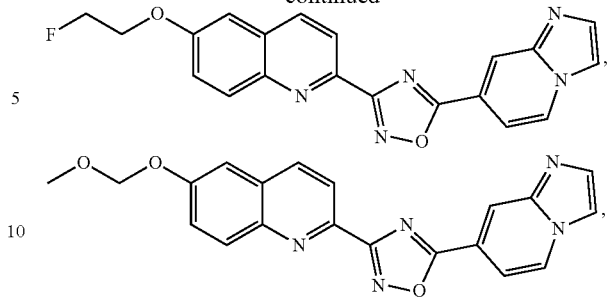

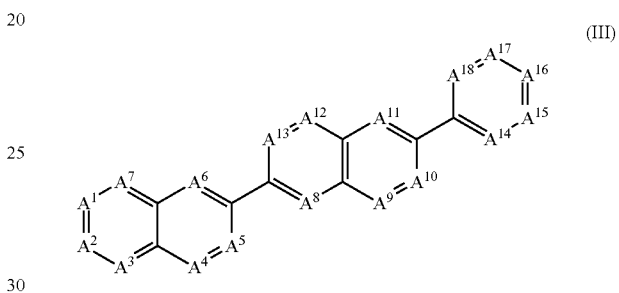

and pharmaceutically acceptable salts thereof.

Further α-synuclein ligands of the present invention comprise compounds of Formula (III) or pharmaceutically acceptable salts thereof:

(III)

wherein $A^1$ is C—$R^1$ or nitrogen; $A^2$ is C—$R^2$ or nitrogen; $A^3$ is C—$R^3$ or nitrogen; $A^4$ is C—$R^4$ or nitrogen; $A^5$ is C—$R^5$ or nitrogen; $A^6$ is C—$R^6$ or nitrogen; $A^7$ is C—$R^7$ or nitrogen; $A^8$ is C—$R^8$ or nitrogen; $A^9$ is C—$R^9$ or nitrogen; $A^{10}$ is C—$R^{10}$ or nitrogen; $A^{11}$ is C—$R^{11}$ or nitrogen; $A^{12}$ is C—$R^{12}$ or nitrogen; $A^{13}$ is C—$R^{13}$ or nitrogen, $A^{14}$ is C—$R^{14}$ or nitrogen, $A^{15}$ is C—$R^{15}$ or nitrogen, $A^{16}$ is C—$R^{16}$ or nitrogen, $A^{17}$ is C—$R^{17}$ or nitrogen, $A^{18}$ is C—$R^{18}$ or nitrogen and each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently hydrogen, nitro, halo, cyano, hydroxy, carboxyl, substituted or unsubstituted hydrocarbyl, substituted or unsubstituted alkyl, substituted or unsubstituted alkoxy, substituted or unsubstituted carboxylate, substituted or unsubstituted alkenyloxy, substituted or unsubstituted amino, substituted or unsubstituted thiourea, or substituted or unsubstituted amido.

In certain embodiments, at least three of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$ and $A^{18}$ are nitrogen. In some embodiments, at least one of $A^1$, $A^2$, $A^3$, $A^4$, $A^5$, $A^6$, $A^7$, at least one of $A^8$, $A^9$, $A^{10}$, $A^{11}$, $A^{12}$, $A^{13}$ and at least one of $A^{14}$, $A^{15}$, $A^{16}$, $A^{17}$ and $A^{18}$ are nitrogen. For example, $A^4$, $A^{11}$ and $A^{17}$ can each be nitrogen.

In some embodiments, $A^1$, $A^2$, $A^3$, $A^5$, $A^6$, $A^7$, $A^8$, $A^9$, $A^{10}$, $A^{12}$, $A^{13}$, $A^{14}$, $A^{15}$, and $A^{17}$ are each C—H. In further embodiments, $A^{16}$ is C—$R^{16}$ and $R^{16}$ is not hydrogen. In further embodiments, $A^{18}$ is C—$R^{18}$ and $R^{18}$ is not hydrogen. In still further embodiments, $A^{16}$ is C—$R^{16}$ and $A^{18}$ is C—$R^{18}$ and each $R^{16}$ and $R^{18}$ are not hydrogen.

Further, each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ can independently be selected from the group consisting of hydrogen, halo, nitro, cyano, substituted or unsubstituted $C_1$ to $C_6$ alkyl, substituted or unsubstituted $C_1$ to $C_6$ alkoxy, substituted or unsubstituted $C_1$ to $C_6$ alkenyloxy, substituted or unsubstituted amino, substituted or unsubstituted amido, and substituted or unsubstituted thiourea.

In some embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ can be selected from the group consisting of hydrogen, halo, nitro, hydroxyl, cyano, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, amido, $C_1$ to $C_6$ alkylamido, $C_1$ to $C_6$ alkyl-substituted thiourea, $C_1$ to $C_6$ alkyl-substituted carboxylate, $C_1$ to $C_6$ haloalkyl-substituted carboxylate.

In certain embodiments, each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ can be selected from the group consisting of hydrogen, a halo, nitro, —CHO, —COCH$_3$, —COOH, —CO$_2$CH$_3$, —OCH$_3$, —OCH$_2$CH$_2$F, —OCH(CH$_3$)$_2$, —OCH$_2$OCH$_3$, —CH$_2$OCH$_3$, —CH$_2$OCH$_2$CH$_2$F, —NO$_2$, —CN, —CH$_2$N(CH$_2$CH$_3$)$_2$, —CH$_2$OH, —OH,

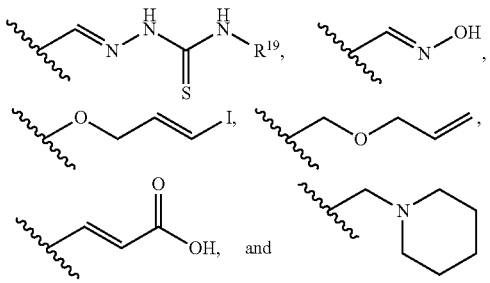

wherein $R^{19}$ is substituted or unsubstituted aryl, substituted or unsubstituted alkyl, substituted or unsubstituted alkenyl, or substituted or unsubstituted alkynyl. In some embodiments, $R^{19}$ is phenyl, $C_1$ to $C_6$ alkyl, $C_1$ to $C_6$ alkenyl, or $C_1$ to $C_6$ alkynyl.

In some embodiments, $R^{16}$ and $R^{18}$ are each independently selected from a group consisting of hydrogen, halo, nitro, cyano, substituted or unsubstituted $C_1$ to $C_6$ alkyl, substituted or unsubstituted $C_1$ to $C_6$ alkoxy, substituted or unsubstituted $C_1$ to $C_6$ alkenyloxy, substituted or unsubstituted amino, substituted or unsubstituted amido, and substituted or unsubstituted thiourea. For example, $R^{16}$ and $R^{18}$ can each be selected from the group consisting of hydrogen, halo, nitro, hydroxyl, cyano, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, $C_1$ to $C_6$ alkenyloxy, halo-substituted $C_1$ to $C_6$ alkenyloxy, amino, $C_1$ to $C_6$ alkylamino, amido, $C_1$ to $C_6$ alkyl-substituted thiourea, $C_1$ to $C_6$ alkyl-substituted carboxylate, $C_1$ to $C_6$ haloalkyl-substituted carboxylate. For example, $R^{16}$ and $R^{18}$ can each be a hydrogen or an alkoxy.

In various embodiments, the compound of Formula (III) can be selected from the group consisting of:

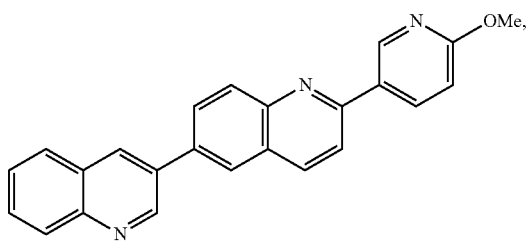

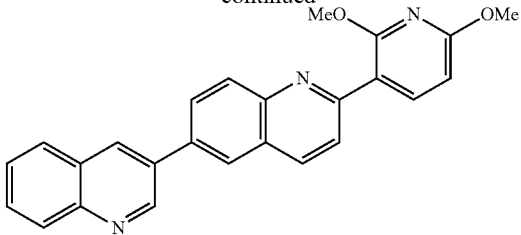

and pharmaceutically acceptable salts thereof.

Unless otherwise indicated, the alkyl, alkenyl, and alkynyl groups described herein preferably from 1 to 20 carbon atoms in the principal chain. They may be straight or branched chain or cyclic. Alkenyl groups can contain saturated or unsaturated carbon chains so long as at least one carbon-carbon double bond is present. Alkynyl groups can contain saturated or unsaturated carbon chains so long as at least one carbon-carbon triple bond is present. Unless otherwise indicated, the alkoxy groups described herein contain saturated or unsaturated, branched or unbranched carbon chains having from 1 to 20 carbon atoms in the principal chain.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl (e.g., cyano), substituted cycloalkyl and the like.

As noted, the compounds of the present invention possess binding affinity to α-synuclein which is useful for certain diagnostic and monitoring methods for synucleinopathies such as PD. One diagnostic method that is suitable for use with the α-synuclein ligands of the present invention is positron emission tomography (PET). PET is known in the art of nuclear medicine imaging as a non-invasive imaging modality that can provide functional information of a living subject at the molecular and cellular level. PET utilizes biologically active molecules in micromolar or nanomolar concentrations that have been labeled with short-lived positron emitting isotopes. The physical characteristics of the isotopes and the molecular specificity of labeled molecules, combined with the high detection efficacy of modern PET scanners provides a sensitivity for in vivo measurements of indicator concentrations that is several orders of magnitude higher than with other imaging techniques.

In order to make measurements with PET, a biologically active tracer molecule labeled with a positron-emitting isotope is administered to a subject, for example, intravenously, orally, or by inhalation. The subject is then scanned, and axial tomographic slices of regional cerebral tracer accumulation are obtained. This tracer accumulation can be related to cerebral metabolism, blood flow, or binding site concentrations by appropriate mathematical models. Thus, by using a small molecular PET radiotracer which has high affinity and selectivity to α-synuclein protein, the level of α-synuclein aggregation can be quantified. This approach not only improves the diagnostic accuracy of PD, but also provides a tool to monitor the progression of the disease and the efficacy of the treatment, and improve the understanding of disease progression.

Accordingly, embodiments of the present invention provide for a radiolabeled compound or composition, or a compound or composition with a radionuclide.

The radiolabeled compound or composition can comprise any compound described herein (e.g., a compound of Formula (I-a), (I-b), (II), or (III)) radiolabeled with a radioactive isotope. References herein to "radiolabeled" include a compound where one or more atoms are replaced or substituted by an atom having an atomic mass or mass number different from the atomic mass or mass number typically found in nature (i.e., naturally occurring). One non-limiting exception is $^{18}$F, which allows detection of a molecule which contains this element without enrichment to a higher degree than what is naturally occurring. Compounds carrying the substituent $^{18}$F may thus also be referred to as "labeled" or the like. The term radiolabeled may be interchangeably used with "isotopically-labeled", "labeled", "isotopic tracer group", "isotopic marker", "isotopic label", "detectable isotope", "radiotracer, and "radioligand". In some embodiments, the compound comprises a single radiolabeled group.

In various embodiments, the compounds of the present invention, including those represented by Formulas (I-a), (I-b), (II) and (III), can be labeled with a radioactive isotope (e.g., synthetic radioactive isotopes) including, for example, carbon-11, nitrogen-13, oxygen-15, fluorine-18, bromine-76, iodine-123, and iodine-125 to serve as tracers for quantifying α-synuclein protein aggregation in the brain. In various embodiments, the compounds of Formulas (I-a), (I-b), (II) and (III) are labeled with a radioactive isotope selected from the group consisting of carbon-11, fluorine-18, iodine-123, and iodine-125. Methods known in the art for radiolabeling the compounds of the present invention may be used. Non-limiting reagents having a radionuclide that may be used in the preparation radiolabeled compounds of the present invention include for example [$^{11}$C]CH$_3$I, [$^{18}$F]CH$_2$CH$_2$OTs, and Na$^{125}$I.

The present invention is also directed to various pharmaceutical compositions comprising one or more of radiolabeled compounds of Formulas (I-a), (I-b), (II) and (III). In various embodiments, the pharmaceutical composition comprises from about 0.001 mg to about 10 g of a compound of Formulas (I-a), (I-b), (II) or (III) and at least about 10 wt. %, at least about 25 wt. %, at least about 50 wt. %, at least about 75 wt. %, at least about 90 wt. %, or at least about 95 wt. % of the compound in the pharmaceutical composition is radiolabeled. The pharmaceutical compositions can also contain one or more excipients.

The compounds of present invention may be formulated in a suitable pharmaceutical delivery medium or vehicle. In various embodiments, the pharmaceutical composition comprises an injectable comprising a compound of the present invention. In other embodiments, the pharmaceutical delivery medium comprises an oral vehicle comprising a compound of the present invention (e.g., capsule, pill, liquid, suspension, etc.).

Further, in accordance with the present invention, methods for diagnosing or monitoring synucleinopathies are provided. In various embodiments, the method for diagnosing or monitoring a synucleinopathy in a subject comprises administering a radiolabeled compound of Formulas (I-a), (I-b), (II) and (III) or pharmaceutically acceptable salts thereof or pharmaceutical composition comprising a radiolabeled compound of Formulas (I-a), (I-b), (II) and (III) or pharmaceutically acceptable salts thereof to the subject; and imaging the subject's brain by positron emission tomography. In various embodiments, the subject is a mammal (e.g., a human). In some embodiments, the subject comprises a human suffering from Parkinson's disease.

Having described the invention in detail, it will be apparent that modifications and variations are possible without departing from the scope of the invention defined in the appended claims.

EXAMPLES

The following non-limiting examples are provided to further illustrate the present invention.

All reagents and chemicals were purchased from commercial suppliers and used without further purification unless otherwise stated. Melting points were determined on a MEL-TEMP 3.0 apparatus and left uncorrected. $^1$H NMR and $^{13}$C NMR spectra were recorded at 400 or 300 MHz on a Varian Mercury-VX spectrometer with CDCl$_3$, CD$_3$COCD$_3$, CD$_3$OD, CD$_3$SOCD$_3$ as solvent and tetramethylsilane (TMS) as the internal standard. All chemical shift values are reported in parts per million (ppm) (δ). With this condition, the chemical shifts (in ppm) of residual solvents are observed at 7.26 (CDCl$_3$), 2.05 (CD$_3$COCD$_3$), 4.80 (CD$_3$OD), 2.50 (CD$_3$SOCD$_3$) for $^1$H NMR. The following abbreviations were used to describe peak patterns wherever appropriate: b=broad, d=doublet, t=triplet, q=quartet, m=multiplet. HRMS analyses were conducted in Washington University Resource for Biomedical and Bioorganic Mass Spectrometry. Preparative chromatography was performed on Chemglass chromatography column using 230-400 mesh silica gel purchase from Silicycle. Analytical TLC was carried out on Merck 60 F$_{254}$ silica gel glass plates, and visualization was aided by UV.

Example 1. Synthesis of Analogues Having Methoxy Groups on Quinolone Ring

New analogues possessing methoxy group on the 7- and 8-position of the quinoline ring were prepared with the goal of improving selectivity for α-synuclein versus Aβ and tau proteins. The palladium-catalyzed coupling reaction gave the product in higher yield than direct aromatic nucleophilic substitution. To confirm that the secondary NH plays an important role for the binding affinity, the secondary amine was converted to a tertiary amine with a methyl protection to give compound TZ61-66 (Scheme 1). Detailed synthesis is shown in Examples 2 and 3 below.

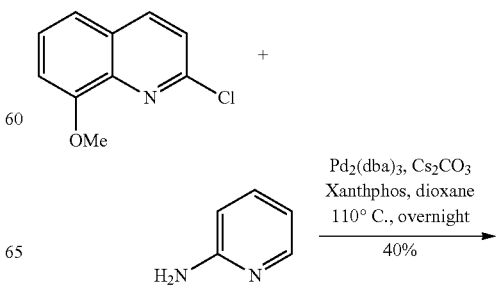

Scheme 1. Synthesis of new α-synuclein compounds bearing a nitrogen bridge.

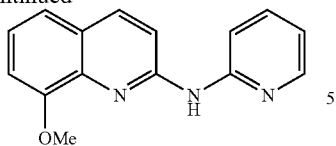

TZ61-61

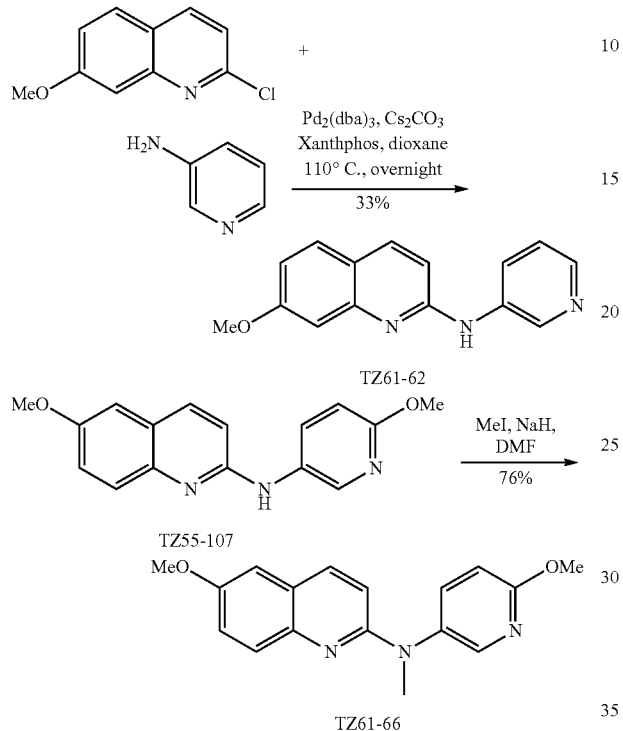

TZ61-62

TZ55-107

TZ61-66

Example 2. Synthesis of TZ61-61 and TZ61-62

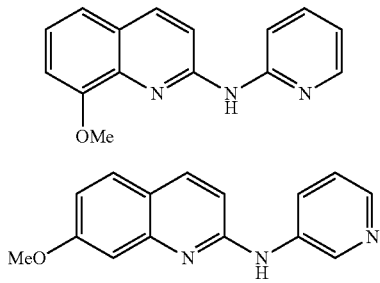

TZ61-61

TZ61-62

To a solution of 2-chloro-8-methoxyquinoline (39 mg, 0.20 mmol) in anhydrous dioxane (6 mL) was added pyridin-2-amine or pyridine-3-amine (19 mg, 0.20 mmol), $Cs_2CO_3$ (130 mg, 0.40 mmol), $Pd_2(dba)_3$ (18 mg, 0.02 mmol), Xantphos (12 mg, 0.02 mmol) successively under nitrogen. The mixture was stirred at 100° C. in a sealed tube overnight. Water was added to quench the reaction and the mixture was extracted with EtOAc. The combined organic phase was washed with saturated aqueous sodium chloride, and dried over anhydrous $Na_2SO_4$. The organic phase was concentrated in vacuo and the residue was subjected to silica gel chromatography (hexane/EtOAc 1/1, v/v) to give the target compound TZ61-61 as a yellow solid (20 mg, 40% yield) or compound TZ61-62 as a solid (33% yield).

Example 3. Synthesis of TZ61-23

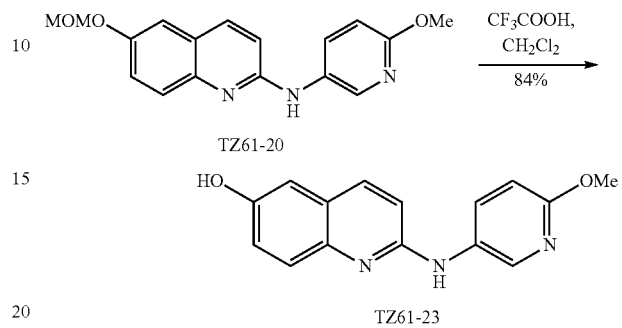

TZ61-20

TZ61-23

To a solution of MOMO group protected TZ61-20 (62 mg, 0.20 mmol) in anhydrous $CH_2Cl_2$ (2 mL) was added $CF_3COOH$ (1 mL) at 0° C. The solution was stirred at room temperature overnight. Water was added to quench the reaction and the mixture was extracted with EtOAc, the combined organic phase was washed with saturated sodium bicarbonate, water, saturated sodium chloride, dried over anhydrous $Na_2SO_4$. The organic layer was concentrated and the residue was subjected to silica gel chromatography (hexane/EtOAc 1/1) to afford product TZ61-23 as a light yellow solid (45 mg, 84% yield).

Example 4. Synthesis of TZ-61-107

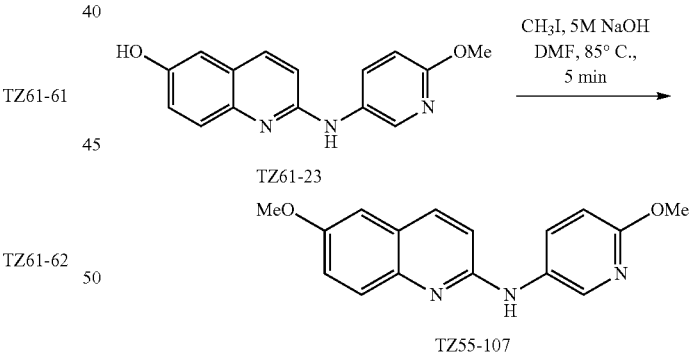

TZ61-23

TZ55-107

The demethylphenol precursor TZ61-23 (~1-2 mg) was dissolved into ~180 μL anhydrous DMF, followed by adding 2 μL of 5 nM into the solution, and vortexed. CH3OI was bubbled into the abovementioned solution within 2-4 minutes and the reaction was heated at ~85° C. for ~5 min and then cooled down to room temperature. The reaction mixture was diluted with corresponding HPLC mobile phase (1.8 mL) and then uploaded onto reverse phase HPLC semi-preparative for purification. The final project was ringed into a dose vial using 0.5 mL absolutely ethanol, which is ready for transferring into biological lab for binding characterization.

Example 5. Synthesis of TZ-61-66

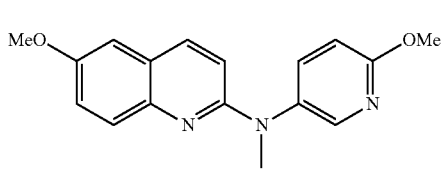

To a solution of TZ55-107 (10 mg, 0.036 mmol) in anhydrous DMF (1 mL) was added NaH (3 mg, 0.11 mmol) at 0° C. 10 min later, MeI (16 mg, 0.11 mmol) was added in one portion. The reaction was allowed to proceed at room temperature overnight. Water was added to quench the reaction and the mixture was extracted with EtOAc. The combined organic phase was washed with saturated aqueous sodium chloride, and dried over anhydrous $Na_2SO_4$. The organic phase was concentrated in vacuo and the residue was subjected to silica gel chromatography (hexane/EtOAc 2/1, v/v) to give the target compound TZ61-66 as a solid (8 mg, 76% yield).

Example 6. Synthesis of Iodine-125 Radiolabeling Precursors

Since preliminary binding assays shows compounds TZ55-107, TZ61-44 have good binding affinity towards PD fibrils and moderate selectivity (see FIGS. 4A-4F and 7A-8F), further development was directed towards an iodine labeled compound. Iodine-125 radiolabeling precursor and a standard reference were synthesized according to Scheme 3. Reaction of compound TZ61-57, prepared as described below, with $CBr_4$ in the presence of $Ph_3P$ afforded compound TZ61-82. Reaction of propargyl alcohol with $Bu_3SnH$ initiated by AIBN produced compound TZ61-83, which was subjected to bromination to give compound TZ61-79. The phenol TZ61-23 (Example 3) reacted with compound TZ61-79 to afford the radiolabeling precursor TZ61-80; when reacting with TZ61-82 afforded standard reference TZ61-84, respectively (Scheme 2). Careful analysis of the NMR spectra and running a second cold reaction, confirmed that TZ61-84 was the correct standard compound as the second peak on HPLC system (Scheme 2).

Scheme 2
Preparation of Iodine-125 radiolabeling precursor (TZ61-80) and standard reference (TZ61-84).

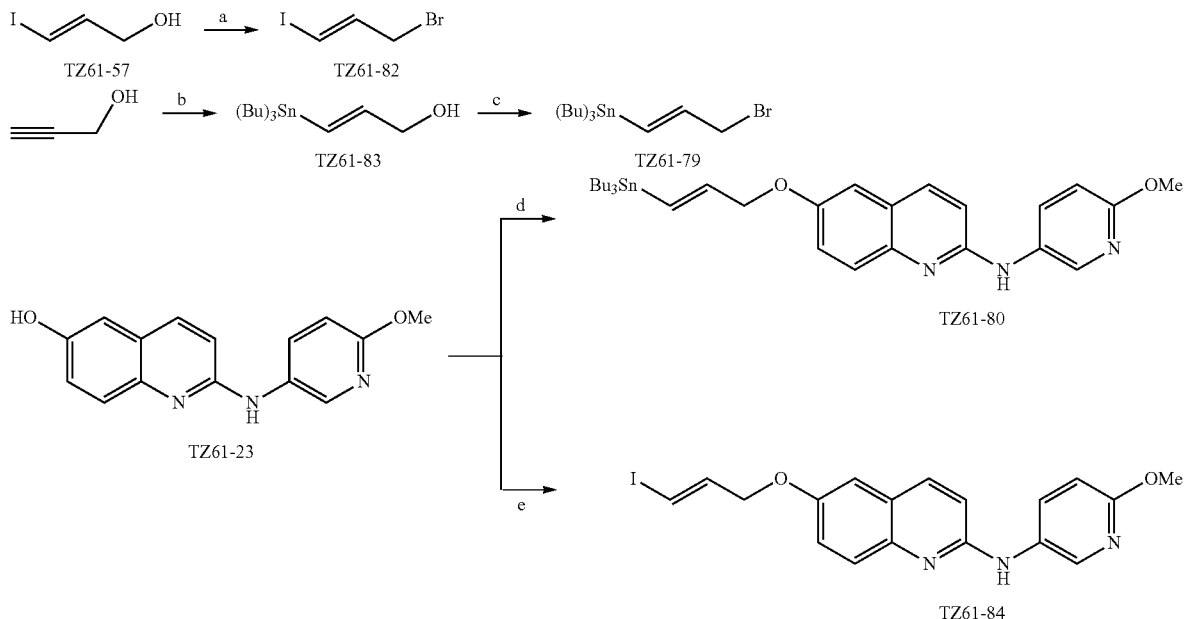

Reagents and conditions:
a $CBr_4$, $Ph_3P$, $CH_2Cl_2$, 90%;
b $Bu_3SnH$, AIBN, toluene, 42%;
c $CBr_4$, $Ph_3P$, $CH_2Cl_2$, 85%;
d TZ61-79, $Cs_2CO_3$, THF, 75° C., 40%;
e TZ61-82, $Cs_2CO_3$, THF, 75° C., 55%.

Example 7. Synthesis of T61-57

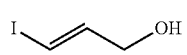

To a solution of TZ61-52 (0.4 g, 1.2 mmol) in $CHCl_3$ (15 mL) was added a solution of iodine (445 mg, 2.0 mmol) in $CHCl_3$ (15 mL). The mixture was stirred at room temperature for 2 h. 5% aqueous sodium metabissulfite was added to quench the reaction and the mixture was extracted with EtOAc, the combined organic phase was washed with saturated sodium chloride, dried over anhydrous $Na_2SO_4$. The combined organic layer was concentrated and the residue was subjected to silica gel chromatography (hexane to hexane/EtOAc 6/1) to afford product TZ61-57 as a light yellow oil (187 mg, 87% yield).

Example 8. Synthesis of TZ61-82

To a solution of (E)-3-iodoprop-2-en-1-ol (TZ61-57, 100 mg, 0.54 mmol) in CH$_2$Cl$_2$ (2 mL) was added CBr$_4$ (215 mg, 0.65 mmol), then Ph$_3$P in CH$_2$Cl$_2$ (170 mg, 0.65 mmol) was added dropwise at 0° C. The mixture was stirred at 0° C. for 1 h, then continued to stir at room temperature for 1 h. The reaction mixture was concentrated in vacuo and the residue was subjected to silica gel chromatography (hexane/EtOAc 10/1) to afford product TZ61-82 as a light yellow oil (120 mg, 90% yield).

Example 9. Synthesis of TZ61-83

To a solution of propargyl alcohol (0.84 g, 15 mmol) in toluene (30 mL) was added Bu$_3$SnH (4.3 g, 15 mmol), azobisisobutyronitrile (0.25 g, 1.5 mmol) under nitrogen, respectively. The mixture was stirred at 120° C. for 10 h. The reaction mixture was concentrated and the residue was subjected to silica gel chromatography (hexane to hexane/EtOAc 6/1) to afford product TZ61-83 as a light yellow oil (2.16 g, 42% yield).

Example 10. Synthesis of TZ61-79

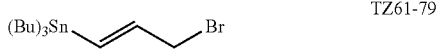

To a solution of TZ61-83 (140 mg, 0.40 mmol) in CH$_2$Cl$_2$ (2 mL) was added CBr$_4$ (159 mg, 0.48 mmol), then Ph$_3$P in CH$_2$Cl$_2$ (126 mg, 0.48 mmol) was added dropwise at 0° C. The mixture was stirred at 0° C. for 1 h, then continued to stir at room temperature for 1 h. The reaction mixture was concentrated in vacuo and the residue was subjected to silica gel chromatography (hexane) to afford product TZ61-79 as a light yellow oil (141 mg, 85% yield).

Example 11. Synthesis of TZ61-80

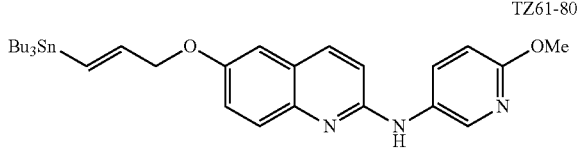

To a solution of TZ61-23, prepared as described in Example 3 (20 mg, 0.075 mmol) in anhydrous THF (2 mL) was added Cs$_2$CO$_3$ (32 mg, 0.098 mmol), (E)-(3-bromoprop-1-en-1-yl)tributylstannane (37 mg, 0.090 mmol) successively. The mixture was stirred at 75° C. in a sealed tube overnight. After cooling down to room temperature, the reaction mixture was concentrated in vacuo and the residue was subjected to silica gel chromatography (hexane/EtOAc 6/1) to afford product TZ61-80 as a yellow solid (18 mg, 40% yield).

Example 12. Synthesis of TZ61-84

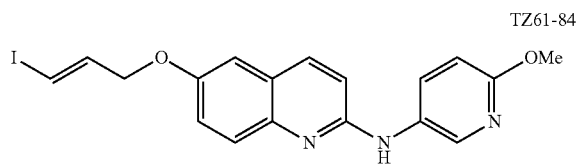 [SMILES: COc1ccc(Nc2ccc3cc(OC/C=C/I)ccc3n2)cn1]

To a solution of TZ61-23, prepared as described in Example 3, (27 mg, 0.10 mmol) in anhydrous THF (2 mL) was added Cs$_2$CO$_3$ (49 mg, 0.15 mmol), (E)-3-bromo-1-iodoprop-1-ene (30 mg, 0.12 mmol) successively. The mixture was stirred at 75° C. in a sealed tube overnight. After cooling down to room temperature, the reaction mixture was concentrated in vacuo and the residue was subjected to silica gel chromatography (hexane/EtOAc 2/1) to afford product TZ61-84 as a yellow solid (24 mg, 55% yield).

Example 13. Synthesis of TZ61-44 (non-radiolabeled)

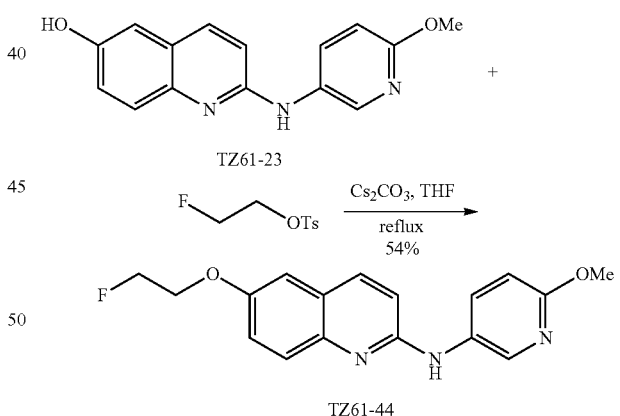

To a solution of TZ61-23, prepared as described in Example 3, (11 mg, 0.040 mmol) in anhydrous THF (2 mL) was added Cs$_2$CO$_3$ (21 mg, 0.064 mmol), 2-fluoroethyl tosylate (13 mg, 0.060 mmol) successively. The mixture was stirred at 70° C. in a sealed tube overnight. Water was added to quench the reaction and the mixture was extracted with EtOAc, the combined organic phase was washed with saturated sodium chloride, dried over anhydrous Na$_2$SO$_4$. The combined organic layer was concentrated and the residue was subjected to silica gel chromatography (hexane/EtOAc 1/1) to afford product TZ61-44 as a yellow solid (7 mg, 54% yield).

Initial competitive binding assay showed that TZ61-44 had good binding affinity towards α-synuclein fibrils and moderate binding affinity for PD tissues (see FIGS. 1A-4F).

Example 14. Synthesis of TZ61-78

Reaction of TZ61-44 with neat HBr (48%) gave the radiolabeling precursor TZ61-78 in 84% yield (Scheme 3).

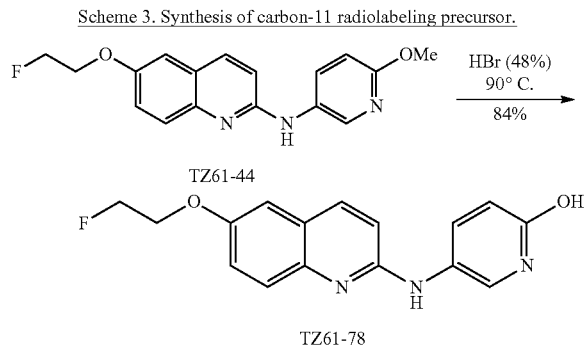

Scheme 3. Synthesis of carbon-11 radiolabeling precursor.

A solution of TZ61-44 (15 mg, 0.048 mmol) in HBr (48%, 2 mL) was heated at 90° C. in a sealed tube overnight. Water was added to quench the reaction and saturated sodium bicarbonate solution was added slowly to neutralize the reaction, then the mixture was extracted with EtOAc. The combined organic phase was washed with saturated aqueous sodium chloride, and dried over anhydrous $Na_2SO_4$. The organic phase was concentrated in vacuo and the residue was subjected to silica gel chromatography (hexane/EtOAc 1/1 to EtOAc) to give the target compound TZ61-78 as a yellow solid (12 mg, 87% yield).

Example 15. Synthesis of Analogues Containing a Quinolinyl Moiety and an Oxadiazole Bridge (e.g., Compounds 18-34)

General: All reagents and chemicals were purchased from commercial suppliers and used without further purification unless otherwise stated. $^1H$ NMR and $^{13}C$ NMR spectra were recorded at 400 MHz on a Varian spectrometer with $CDCl_3$, $CD_3COCD_3$, $CD_3SOCD_3$ as solvent and tetramethylsilane (TMS) as the internal standard. All chemical shift values are reported in parts per million (ppm) (δ). Under these conditions, the chemical shifts (in ppm) of residual solvents are observed at 7.26 ($CDCl_3$), 2.05 ($CD_3COCD_3$), 2.50 ($CD_3SOCD_3$) for $^1H$ NMR. The following abbreviations were used to describe peak patterns wherever appropriate: br=broad, d=doublet, t=triplet, m=multiplet. HRMS analyses were conducted in Washington University Resource for Biomedical and Bio-organic Mass Spectrometry. Preparative chromatography was performed on Chemglass chromatography column using 230-400 mesh silica gel purchase from Silicycle. Analytical TLC was carried out on Merck 60 $F_{254}$ silica gel glass plates, and visualization was aided by UV.

The synthesis of new quinolinyl analogues with an oxadiazole bridge is described in Scheme 4. Briefly, reaction of commercially available 6-methoxyquinoline-2-carbonitrile 17 with hydroxylamine hydrochloride afforded carboximidamide 18 in near quantititative yield, which was used for the next condensation reaction without further purification. Removal of the methyl group in compound 17 gave phenol 19 which was alkylated to produce 6-position modified compounds 20-22. Compounds 20-22 were converted to corresponding carboximidamides 23-25 using a similar strategy as 18. Condensation of compounds 18, 23-25 with nicotinic acid or isonicotinic acid afforded compounds 26-30. By a similar strategy, four imidazolepyridine analogs 31-34 were obtained in moderate yield (Scheme 4). Detailed descriptions of reactions (a-d) are provided in the following examples.

Scheme 4. Synthesis of oxadiazole containing α-synuclein compounds.

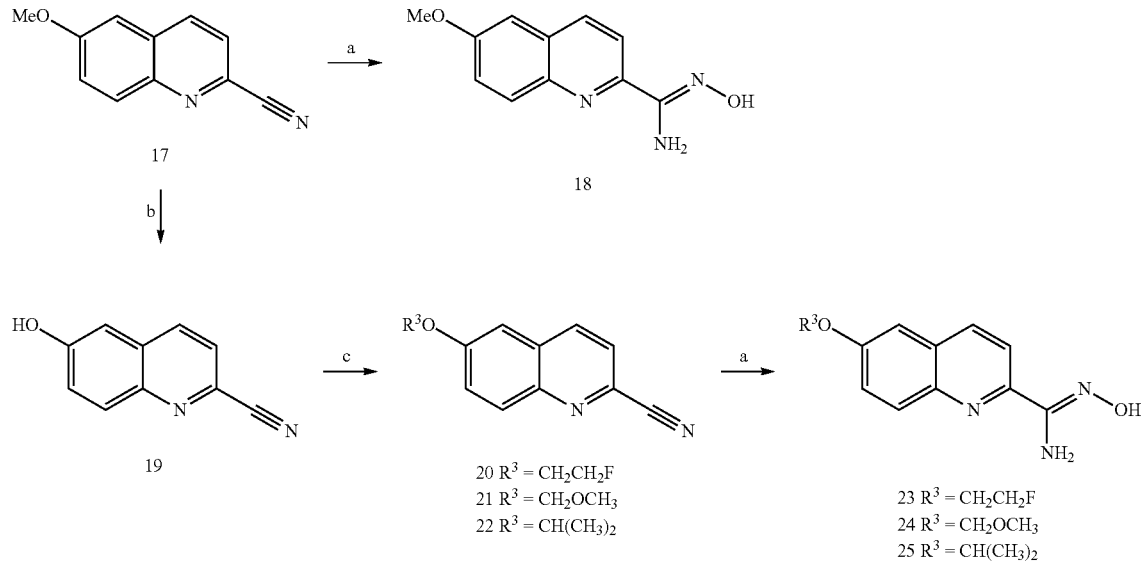

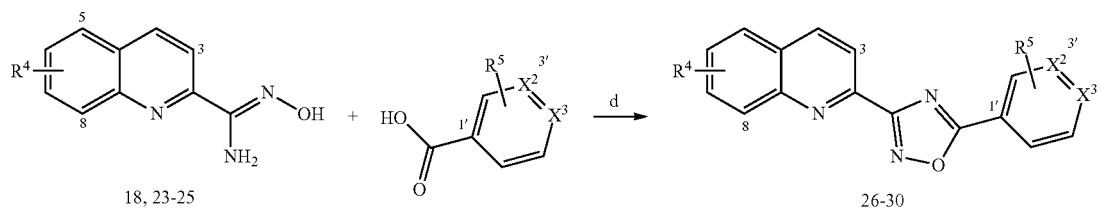

26. R⁴ = 6-OMe, R⁵ = H, X² = N, X³ = H;
27. R⁴ = 6-OMe, R⁵ = 3′-OMe, X² = H, X³ = N;
28. R⁴ = 6-FCH₂CH₂O, R⁵ = 3′-OMe, X² = H, X³ = N;
29. R⁴ = 6-CH₃OCH₂O, R⁵ = 3′-OMe, X² = H, X³ = N;
30. R⁴ = 6-CH(CH₃)₂O, R⁵ = 3′-OMe, X² = H, X³ = N.

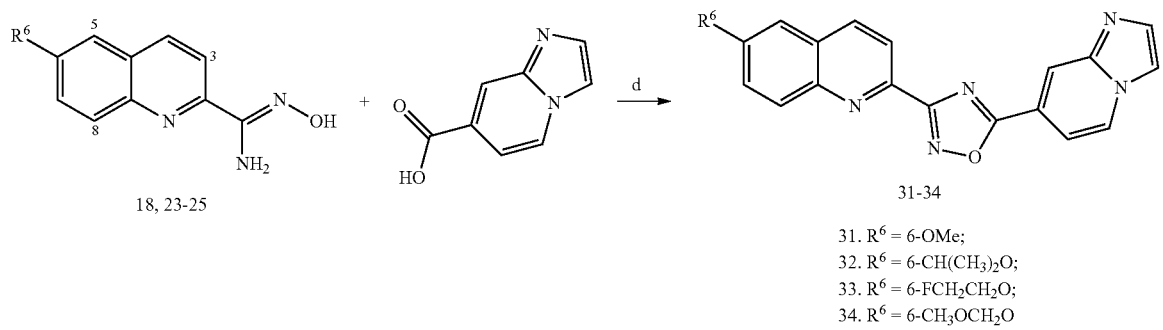

31. R⁶ = 6-OMe;
32. R⁶ = 6-CH(CH₃)₂O;
33. R⁶ = 6-FCH₂CH₂O;
34. R⁶ = 6-CH₃OCH₂O

Reagents and conditons:
a NH₂OH·HCl, EtOH/H₂O (2/1, v/v), NaHCO₃;
b AlCl₃, ClCH₂CH₂Cl;
c Cs₂CO₃, THF, 70° C., TsOCH₂CH₂F for 20, MeOCH₂Cl for 21, CHBr(CH₃)₂ for 22;
d EDCI·HCl, HOBt, DIPEA, DMF, 130° C.

Example 16. General Procedure for Carboximidamide Formation (Scheme 4, Reaction "a")

To a solution of quinoline-2-carbonitrile derivatives (0.4 M, 1 equiv.) in EtOH/H₂O (2/1, v/v) was added hydroxylamine hydrochloride (1 equiv.), sodium bicarbonate (2 equiv.) successively. The mixture was stirred at 100° C. overnight. Upon cooling to the room temperature, water was added and the reaction mixture was extracted with EtOAc. The combined organic phase was washed with water, saturated aqueous sodium chloride, and dried over anhydrous Na₂SO₄. The organic phase was then concentrated to afford the carboximidamide product, which was used without further purification for the next condensation step. Compounds 18, 23, 24, and 25 were prepared in this way from precursors 17, 20, 21, and 22, respectively.

Example 17. Synthesis of 6-Hydroxyquinoline-2-carbonitrile (19) (Scheme 4, Reaction "b")

To a solution of 6-methoxyquinoline-2-carbonitrile (552 mg, 3 mmol) in CH₂Cl₂ (20 mL) was added AlCl₃ (1.0 g, 7.5 mmol). The reaction was stirred at 45° C. overnight in a sealed tube. TLC showed the starting material remained so a second portion of AlCl₃ was added (1.0 g, 7.5 mmol). Water was added to quench the reaction and the mixture was extracted with EtOAc. The combined organic phase was washed with saturated bicarbonate solution, saturated sodium chloride, respectively. The concentrated residue was subjected to silica gel chromatography (hexane/EtOAc, 3/1, v/v) to afford 6-hydroxyquinoline-2-carbonitrile (268 mg, 52% yield). ¹H NMR (400 MHz, CD₃COCD₃) δ 9.41 (s, 1H), 8.22 (d, J=8.5 Hz, 1H), 7.87 (d, J=9.2 Hz, 1H), 7.68-7.62 (m, 1H), 7.44-7.38 (m, 1H), 7.20 (d, J=1.8 Hz, 1H).

Example 18. General Procedure for Alkylation of 6-hydroxyquinoline. (Scheme 4, Reaction "c")

To a solution of 6-hydroxyquinoline-2-carbonitrile (1 equiv.) in anhydrous THF (0.08 M) was added Cs₂CO₃ (1.8 equiv.), 2-fluoroethyl tosylate (1.8 equiv.). The reaction was stirred at 70° C. overnight in a sealed tube. The mixture was concentrated and the residue was subjected to silica gel chromatography to afford the alkylation product.

Example 19. General Procedure for Oxadiazole Formation. (Scheme 4, Reaction "d")

To a solution of acid (1 equiv.) in anhydrous DMF (0.18 M) was added EDCI·HCl (1 equiv.), and HOBt (1 equiv.) successively in a sealed tube. The mixture was stirred at rt for 30 min. Carboximidamide (1 equiv.) was added in one portion and the reaction was placed in a pre-heated 130° C. oil bath and continued to stir overnight. Water was added to quench the reaction and the mixture was extracted with EtOAc. The combined organic phase was washed with saturated aqueous sodium bicarbonate solution, water, saturated aqueous sodium chloride, and dried over anhydrous Na₂SO₄. The organic phase was concentrated in vacuum and the residue was subjected to silica gel chromatography to give the target oxadiazole compound.

Example 20. Synthesis of (Z)-6-(2-Fluoroethoxy)-N'-hydroxyquinoline-2-carboximidamide (20)

Compound was synthesized according to reaction "c" as described in Example 20 from precursor 6-hydroxyquinoline-2-carbonitrile (19). $^1$H NMR (400 MHz, CD$_3$COCD$_3$) δ 8.31 (d, J=8.5 Hz, 1H), 7.91 (d, J=9.3 Hz, 1H), 7.72 (d, J=8.5 Hz, 1H), 7.46 (dd, J=9.3, 2.8 Hz, 1H), 7.36 (d, J=2.8 Hz, 1H), 4.81-4.67 (m, 2H), 4.41-4.32 (m, 2H).

Example 21: Synthesis of 6-(Methoxymethoxy)quinoline-2-carbonitrile (21)

Compound was synthesized according to reaction "c" as described in Example 20 from precursor 6-hydroxyquinoline-2-carbonitrile (19) using MeOCH$_2$Cl instead of 2-fluoroethyl tosylate. $^1$H NMR (400 MHz, CD$_3$COCD$_3$) δ 8.31 (d, J=8.4 Hz, 1H), 7.89 (d, J=9.2 Hz, 1H), 7.69 (d, J=8.5 Hz, 1H), 7.46 (dd, J=9.2, 2.7 Hz, 1H), 7.41 (s, 1H), 5.26 (s, 2H), 3.34 (s, 3H).

Example 22. Synthesis of 6-Isopropoxyquinoline-2-carbonitrile (22)

Compound was synthesized according to reaction "c" as described in Example 20 from precursor 6-hydroxyquinoline-2-carbonitrile (19) using CHBr(CH$_3$)$_2$ instead of 2-fluoroethyl tosylate. $^1$H NMR (400 MHz, CD$_3$COCD$_3$) δ 8.41 (d, J=8.5 Hz, 1H), 7.99 (d, J=9.2 Hz, 1H), 7.81 (dd, J=8.5, 1.2 Hz, 1H), 7.51-7.48 (m, 1H), 7.43 (d, J=2.3 Hz, 1H), 4.98-4.76 (m, 1H), 1.39 (d, J=6.0 Hz, 6H).

Example 23. Synthesis of 3-(6-Methoxyquinolin-2-yl)-5-(pyridin-3-yl)-1,2,4-oxadiazole (26)

Compound was synthesized according to reaction "d" as described in Example 21 from precursors 18 and nicotinic acid. White solid. MP 175-177° C. $^1$H NMR (400 MHz, CDCl$_3$) δ 9.46 (s, 1H), 8.78 (d, J=4.7 Hz, 1H), 8.50 (d, J=8.0 Hz, 1H), 8.19-8.12 (m, 3H), 7.45 (dd, J=7.9, 4.9 Hz, 1H), 7.37 (dd, J=9.2, 2.6 Hz, 1H), 7.05 (d, J=2.6 Hz, 1H), 3.88 (s, 3H). $^{13}$C NMR (101 MHz, CDCl$_3$) δ 174.47, 169.17, 158.97, 153.44, 149.31, 144.28, 143.36, 135.86, 135.53, 131.90, 130.14, 123.77, 123.31, 120.47, 120.45, 104.86, 55.61. HRMS (ESI) calcd. for C$_{17}$H$_{13}$N$_4$O$_2$ [M+H]$^+$ 305.1033, found: 305.0950.

Example 24. Synthesis of 5-(2-Methoxypyridin-4-yl)-3-(6-methoxyquinolin-2-yl)-1,2,4-oxadiazole (27)

Compound was synthesized according to reaction "d" as described in Example 21 from precursors 18 and 2-methoxyisonicotinic acid. White solid. MP 188-189° C. $^1$H NMR (400 MHz, CDCl$_3$) δ 8.33 (d, J=5.3 Hz, 1H), 8.24-8.04 (m, 3H), 7.64 (d, J=5.2 Hz, 1H), 7.54 (s, 1H), 7.38 (dd, J=9.3, 2.7 Hz, 1H), 7.06 (d, J=2.6 Hz, 1H), 3.95 (s, 3H), 3.90 (s, 3H). $^{13}$C NMR (101 MHz, CDCl$_3$) δ 174.68, 169.31, 164.88, 159.01, 148.40, 144.31, 143.32, 135.88, 133.30, 131.93, 130.16, 123.34, 120.45, 114.49, 109.81, 104.86, 55.62, 53.98. HRMS (ESI) calcd. for C$_{18}$H$_{15}$N$_4$O$_3$ [M+H]$^+$ 335.1139, found: 335.1051.

Example 25. Synthesis of 3-(6-(2-Fluoroethoxy)quinolin-2-yl)-5-(2-methoxypyridin-4-yl)-1,2,4-oxadiazole (28)

Compound was synthesized according to reaction "d" as described in Example 21 from precursors 23 and 2-methoxyisonicotinic acid. White solid. MP 235-237° C. NMR (400 MHz, CDCl$_3$) δ 8.34 (d, J=5.3 Hz, 1H), 8.25-8.11 (m, 3H), 7.65 (d, J=5.3 Hz, 1H), 7.55 (s, 1H), 7.44 (dd, J=9.3, 2.7 Hz, 1H), 7.09 (d, J=2.7 Hz, 1H), 4.88-4.68 (m, 2H), 4.37-4.24 (m, 2H), 3.96 (s, 3H). $^{13}$C NMR (101 MHz, CDCl$_3$) δ 174.75, 169.28, 164.90, 157.78, 148.42, 144.46, 143.67, 136.00, 133.28, 132.18, 130.00, 123.38, 120.56, 114.49, 109.83, 105.84, 81.63 (d, J=172.7 Hz), 67.41 (d, J=21.2 Hz), 54.00. HRMS (ESI) calcd. for C$_{19}$H$_{16}$FN$_4$O$_3$ [M+H]$^+$ 367.1201, found: 367.1104.

Example 26. Synthesis of 3-(6-(Methoxymethoxy)quinolin-2-yl)-5-(2-methoxypyridin-4-yl)-1,2,4-oxadiazole (29)

Compound was synthesized according to reaction "d" as described in Example 21 from precursors 24 and 2-methoxyisonicotinic acid. White solid. MP 180-181° C. $^1$H NMR (400 MHz, CDCl$_3$) δ 8.33 (d, J=5.2 Hz, 1H), 8.22-8.15 (m, 3H), 7.64 (d, J=5.2 Hz, 1H), 7.54 (s, 1H), 7.44 (d, J=9.2 Hz, 1H), 7.35 (s, 1H), 5.27 (s, 2H), 3.96 (s, 3H), 3.48 (s, 3H). $^{13}$C NMR (101 MHz, CDCl$_3$) δ 174.72, 169.29, 164.88, 156.43, 148.40, 144.56, 143.81, 136.30, 133.28, 132.01, 129.99, 123.55, 120.41, 114.48, 109.81, 108.79, 94.46, 56.30, 53.98. HRMS (ESI) calcd. for C$_{19}$H$_{17}$N$_4$O$_4$ [M+H]$^+$ 365.1244, found: 365.1405.

Example 27. Synthesis of 3-(6-Isopropoxyquinolin-2-yl)-5-(2-methoxypyridin-4-yl)-1,2,4-oxadiazole (30)

Compound was synthesized according to reaction "d" as described in Example 21 from precursors 25 and 2-methoxyisonicotinic acid. Light yellow solid. MP 171-173° C. $^1$H NMR (400 MHz, CDCl$_3$) δ 8.32 (d, J=5.2 Hz, 1H), 8.20-8.03 (m, 3H), 7.63 (dd, J=5.2, 0.8 Hz, 1H), 7.53 (s, 1H), 7.34 (dd, J=9.3, 2.6 Hz, 1H), 7.04 (d, J=2.5 Hz, 1H), 4.66 (dt, J=12.1, 6.0 Hz, 1H), 3.95 (s, 3H), 1.37 (s, 3H), 1.35 (s, 3H). $^{13}$C NMR (101 MHz, CDCl$_3$) δ 174.64, 169.33, 164.87, 157.27, 148.38, 144.02, 143.13, 135.74, 133.31, 131.97, 130.21, 124.21, 120.33, 114.48, 109.79, 106.77, 70.30, 53.96, 21.87. HRMS (ESI) calcd. for C$_{20}$H$_{19}$N$_4$O$_3$ [M+H]$^+$ 363.1452, found: 363.1353.

Example 28. Synthesis of 5-(Imidazo[1,2-c]pyridin-7-yl)-3-(6-methoxyquinolin-2-yl)-1,2,4-oxadiazole (31)

Compound was synthesized according to reaction "d" as described in Example 21 from precursors 18 and imidazo[1,2-a]pyridine-7-carboxylic acid. Light yellow solid. MP 277-279° C. $^1$H NMR (400 MHz, CDCl$_3$) δ 8.58 (s, 1H), 8.27-8.14 (m, 4H), 7.80 (s, 1H), 7.72-7.63 (m, 2H), 7.39 (dd, J=9.2, 2.8 Hz, 1H), 7.08 (d, J=2.7 Hz, 1H), 3.91 (s, 3H). $^{13}$C NMR (101 MHz, CDCl$_3$) δ 175.02, 169.27, 158.97, 144.31, 144.15, 143.53, 136.47, 135.88, 131.95, 130.15, 126.16, 123.29, 120.50, 119.52, 119.12, 114.18, 110.72, 104.88, 55.64. HRMS (ESI) calcd. for C$_{19}$H$_{14}$N$_5$O$_2$ [M+H]$^+$ 344.1142, found: 344.1052.

Example 29. Synthesis of 5-(Imidazo[1,2-c]pyridin-7-yl)-3-(6-isopropoxyquinolin-2-yl)-1,2,4-oxadiazole (32)

Compound was synthesized according to reaction "d" as described in Example 21 from precursors 25 and imidazo[1,2-a]pyridine-7-carboxylic acid. Brown yellow solid. MP 203-205° C. $^1$H NMR (400 MHz, CD$_3$SOCD$_3$) δ 8.84 (d, J=7.0 Hz, 1H), 8.48 (d, J=7.4 Hz, 2H), 8.31-8.15 (m, 2H), 8.09 (d, J=8.9 Hz, 1H), 7.90 (s, 1H), 7.65 (d, J=7.1 Hz, 1H), 7.48 (d, J=14.6 Hz, 2H), 4.93-4.77 (m, 1H), 1.39 (s, 3H), 1.38 (s, 3H). NMR (101 MHz, CD$_3$SOCD$_3$) δ 175.05, 169.14, 157.06, 143.68, 143.38, 143.34, 136.72, 135.96, 131.48, 130.38, 128.64, 124.61, 120.84, 119.40, 117.73, 116.05, 110.34, 107.76, 70.33, 22.10. HRMS (ESI) calcd. for C$_{21}$H$_{18}$N$_5$O$_2$ [M+H]$^+$372.1455, found: 372.1356.

Example 30. Synthesis of 3-(6-(2-Fluoroethoxy)quinolin-2-yl)-5-(imidazo[1,2-c]pyridin-7-yl)-1,2,4-oxadiazole (33)

Compound was synthesized according to reaction "d" as described in Example 21 from precursors 23 and imidazo[1,2-a]pyridine-7-carboxylic acid. Brown yellow solid. MP 188-190° C. $^1$H NMR (400 MHz, CDCl$_3$) δ 8.66-8.44 (m, 1H), 8.24-8.11 (m, 4H), 7.75 (d, J=41.1 Hz, 1H), 7.67-7.62 (m, 1H), 7.44-7.37 (m, 1H), 7.08-7.03 (m, 2H), 4.89-4.66 (m, 2H), 4.40-4.23 (m, 2H). $^{13}$C NMR (101 MHz, CDCl$_3$) δ 175.05, 169.22, 157.38, 144.45, 144.14, 143.86, 136.45, 135.98, 132.18, 129.97, 126.17, 123.30, 121.20, 120.60, 119.11, 114.20, 110.71, 105.86, 81.63 (d, J=171.7 Hz), 67.41 (d, J=21.2 Hz). HRMS (ESI) calcd. for C$_{20}$H$_{15}$FN$_5$O$_2$ [M+H]$^+$ 376.1204, found: 376.1104.

Example 31. Synthesis of 5-(Imidazo[1,2-c]pyridin-7-yl)-3-(6-(methoxymethoxy)-quinolin-2-yl)-1,2,4-oxadiazole (34)

Compound was synthesized according to reaction "d" as described in Example 21 from precursors 24 and imidazo[1,2-a]pyridine-7-carboxylic acid. Light yellow solid. MP 209-210° C. $^1$H NMR (400 MHz, CDCl$_3$) δ 8.58 (s, 1H), 8.30-8.06 (m, 5H), 7.80-7.65 (m, 3H), 7.50-7.39 (m, 1H), 7.37 (s, 1H), 5.28 (s, 2H), 3.48 (s, 3H). $^{13}$C NMR (101 MHz, CDCl$_3$) δ 175.06, 169.25, 156.40, 144.57, 144.16, 144.02, 136.49, 136.29, 132.03, 129.98, 126.16, 123.49, 120.46, 119.49, 119.14, 114.19, 110.71, 108.82, 94.47, 56.31. HRMS (ESI) calcd. for C$_{20}$H$_{16}$N$_5$O$_3$ [M+H]$^+$ 374.1248, found: 374.1148.

Example 32. Synthesis of 2-(5-(2-Methoxypyridin-4-yl)-1,2,4-oxadiazol-3-yl)quinolin-6-ol (38)

To a solution of compound 34 (26 mg, 0.07 mmol) in CH$_2$Cl$_2$ (2 mL) was added CF$_3$COOH (0.5 mL) at 0° C. The mixture was stirred at room temperature for 3 h. Saturated sodium bicarbonate was added to neutralize the reaction and the mixture was extracted with EtOAc. The combined organic layer was washed with saturated sodium chloride, dried over anhydrous sodium sulfate, concentrated in vacuo, and the residue was subjected to silica gel chromatography (hexane/EtOAc 1/1) to afford product 38 as a yellow solid (18 mg, 79% yield). MP 217-219° C. $^1$H NMR (400 MHz, CD$_3$COCD$_3$) δ 9.17 (s, 1H), 8.37 (d, J=5.2 Hz, 1H), 8.23 (d, J=8.6 Hz, 1H), 8.07 (d, J=8.6 Hz, 1H), 7.97 (d, J=9.1 Hz, 1H), 7.63-7.58 (m, 1H), 7.43-7.35 (m, 2H), 7.21 (d, J=2.4 Hz, 1H), 3.88 (s, 3H). $^{13}$C NMR (101 MHz, CD$_3$SOCD$_3$) δ 172.81, 167.72, 163.16, 155.98, 147.82, 141.58, 140.85, 134.57, 132.06, 130.02, 129.02, 122.26, 119.05, 113.42, 107.64, 107.17, 53.74. HRMS (ESI) calcd. for C$_{17}$H$_{13}$N$_4$O$_3$ [M+H]$^+$ 321.0982, found: 321.0982.

Example 33. Indirect Affinity Determination ($K_i$) of Compounds 26-34 Using Thioflavin T Fluorescence Assay with Recombinant α-Synuclein Fibrils The binding affinity of compounds 26-34 to α-synuclein was measured by an indirect method that comprised a competitive assay using the fluorescent dye Thioflavin T (ThT), which has the structure shown below.

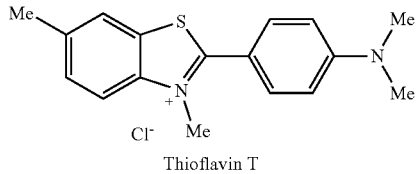

Thioflavin T

ThT is a benzothiazole dye that exhibits enhanced fluorescence upon binding to amyloid fibrils, and is used for the selective staining and identification of amyloid fibrils both in vitro and ex vivo. The changes in the fluorescent properties of ThT upon binding to amyloid fibrils include a shift in its excitation state and an increase in quantum yield. ThT in protic solvents principally absorbs at 340 nm with an emission maximum at 445 nm. Upon binding to amyloid fibrils, a peak at approximately 440 nm becomes dominant with the fluorescent emission maximum shifted to 480 nm. This is accompanied by a strong enhancement of the fluorescence.

The ThT fluorescence emission spectrum has been confirmed to be consistent with reported data. ThT incubated with α-synuclein fibrils prepared as described in this Example has a maximum fluorescence emission wavelength ($\lambda_{em}$) of 485 nm and an excitation wavelength ($\lambda_{ex}$) of 440 nm. No increase in fluorescence emission is observed when ThT is incubated in the presence of monomeric α-synuclein or in α-synuclein free buffer. Furthermore, the ratio of ThT's fluorescence intensity in the presence of α-synuclein fibrils compared to ThT's fluorescence intensity in either monomeric α-synuclein or α-synuclein free buffer has been observed to be about 30-fold.

α-Synuclein recombinant protein was produced in E. coli. BL21(DE3)RIL E. coli were transformed with a pRK172 bacterial expression plasmid containing the human α-synuclein coding sequence. Freshly transformed BL21 colonies were inoculated into 2 L baffled flasks containing 250 mL sterilized TB (1.2% bactotryptone, 2.4% yeast extract, 0.4% glycerol, 0.17 M KH$_2$PO$_4$, 0.72 M K$_2$HPO$_4$) with 50 µg/ml ampicillin, and incubated overnight at 37° C. with shaking. Overnight cultures were pelleted by centrifugation at 3,900×g for 10 min at 25° C. Bacterial pellets were resuspended in 20 mL osmotic shock buffer (30 mM Tris-HCl, 2 mM EDTA, 40% sucrose, pH 7.2) by gentle vortexing and incubated at room temperature for 10 minutes. The cell suspension was then centrifuged at 8,000×g for 10 min at 25° C. and the pellet was resuspended in 22.5 mL cold H$_2$O before adding 9.4 µL 2 M MgCl$_2$ to each tube. The suspension was incubated on ice for 3 min prior to centrifugation at 20,000×g for 15 min at 4° C. The supernatant was transferred to a fresh tube, streptomyocin was added to a final concentration of 10 mg/mL, and then centrifuged at 20,000×g for 15 min at 4° C. The supernatant from this step was collected and dithiothreitol (DTT) and Tris-HCl were added to final concentrations of 1 mM and 20 mM respectively, before boiling for 10 min to precipitate heat-sensitive proteins, which were pelleted at 20,000×g for 15 minutes at 4° C. The supernatant was collected and filtered through a 0.45 μm surfactant free cellulose acetate filter (Corning, Corning, NY) before loading onto a 1 mL DEAE Sepharose column equilibrated in 20 mM Tris-HCl pH 8, 1 mM EDTA, and 1 mM DTT. The DEAE column was washed with 20 mM Tris-HCl pH 8, 1 mM EDTA, 1 mM DTT before eluting α-synuclein protein in 20 mM Tris-HCl, pH 8, buffer with 1 mM EDTA, 1 mM DTT and 0.3 M NaCl. The purified α-synuclein protein was dialyzed overnight in 10 mM Tris-HCl, pH 7.6, 50 mM NaCl, and 1 mM DTT. Preparations contained greater than 95% α-synuclein protein as determined by SDS-PAGE and BCA assay with a typical yield of 30 mg protein per 250 ml culture.

The purified, recombinant α-synuclein monomer (2 mg/mL) was incubated in Tris-HCl (20 mM) and NaCl (100 mM) while shaking at 1000 rpm in an Eppendorf Thermomixer in a 37° C. temperature-controlled room for 72 hours. To determine the concentration of fibrils, the reaction mixture (100 μL) was centrifuged at 18,000×g for 10 minutes to separate fibrils from monomer. The α-synuclein monomer and other soluble proteins in the supernatant were removed, and the fibril pellet was resuspended in 100 μL solution of Tris-HCl (20 mM) and NaCl (100 mM). This fibril suspension was used in a bicinchoninic acid (BCA) protein assay along with a bovine serum albumin (BSA) standard curve to determine the concentration of fibrils in the 72 hour fibril reaction mixture.

To prepare the fibrils for performing binding assays, the fibril reaction mixture prepared above was centrifuged at 18,000×g for 10 minutes. The supernatant was discarded and the fibril pellet was resuspended in Tris-HCl buffer (30 nM, pH=7.4) to achieve the desired concentration (3 or 6 μM) of fibrils for use in the assay.

The ThT solution (6 μM) in Tris-HCl buffer (30 nM, pH=7.4, 40 μL) was added to each of three cells in a 96 cell plate for fluorescence detection containing α-synuclein fibrils suspension (3.0 μM) in the Tris-HCl buffer (30 nM, pH=7.4, 40 μL). The mixture was incubated at room temperature for 1 hour on the shaking plate. The reaction plate was scanned by the excitation wavelength range from 430 to 465 nm. The maximum excitation wavelength ($\lambda_{ex}$) was determined according to the fluorescent intensity-excitation wavelength curve. At ($\lambda_{ex}$), the emission wavelength was scanned to get maximum emission wavelength ($\lambda_{em}$). Then $\lambda_{ex}$ and $\lambda_{em}$ for the free ThT and ThT-monomeric α-synuclein was determined by the procedure described above.

ThT solutions of various concentration from 10 nM to 40 μM in Tris-HCl buffer (30 nM, pH=7.4, 40 μL) were added to a 96 cell plate containing α-synuclein fibrils (3.0 μM) in the Tris-HCl buffer (30 nM, pH=7.4, 40 μL). The mixture was incubated at room temperature for 1 hour on the shaking plate. The fluorescent intensity for each cell was measured by the fluorescence reader at $\lambda_{ex}$ and $\lambda_{em}$. The ThT-α-synuclein fibrils saturation curve and $K_d$ value were produced by the software Prism 5. The $K_d$ value for ThT binding to α-synuclein fibrils has been determined to be 948±271 nM.

Once the ThT-α-synuclein saturation binding curve and dissociation constant ($K_d$) were determined the competitive assay for determining the binding affinity of various test compounds was conducted. ThT solution (12 μM) in Tris-HCl buffer (30 nM, pH=7.4, 20 μL) was added to a 96 cell plate containing α-synuclein fibrils (6.0 μM) in the Tris-HCl buffer (30 nM, pH=7.4, 20 μL) and test compounds at various concentrations (from 1 nM to 10 μM) in Tris-HCl buffer (30 nM, pH=7.4, 40 μL) with 10% dimethyl sulfoxide. The mixture was incubated at room temperature for 60 minutes on the shaking plate. The fluorescent intensity for each cell was measured by the fluorescence reader at $\lambda_{ex}$ and $\lambda_{em}$. The $K_i$ value for each compound was calculated by the corresponding inhibition curve.

$EC_{50}$ values for each compound were determined by fitting the data to the equation $Y=\text{Bottom}+(\text{Top}-\text{Bottom})/(1+(X-\text{Log } EC_{50})^{-Hillcoefficient})$ using nonlinear regression by Kaleidagraph software, where Top and Bottom are the Y values for the top and bottom plateaus of the binding curve. The $K_i$ values were derived from the $EC_{50}$ values using the Cheng-Prusoff equation: $K_i=EC_{50}/(1+[\text{radioligand}]/K_d)$.

Although fluorescence quenching can potentially interfere with measurement of competitive binding, the data for the individual compounds closely fit a competitive binding model. Absorbance spectra were measured at the $EC_{50}$ concentration for each compound. Absorbance was less than 0.001 in the range of 400-500 nM for all of the compounds, indicating that absorbance at the excitation or emission wavelengths did not interfere with the fluorescence assay.

Table 1 below describes the dissociation constant (Ki) of compounds 26-34, and TZ64-55, TZ64-82, TZ64-102, TZ64-105, TZ64-19, TZ66-16, TZ66-25 and TZ64-91 as determined by the Thioflavin T assay described herein. For oxadiazole containing compounds 26-34, one fragment was 6-position modified quinolinyl moiety and the other part included a pyridyl or imidazolepyridyl fragment. Of the oxadiazole containing compounds, compound 28 displayed high binding affinity with a $K_i$ value of 17 nM, but the other compounds had very weak potency with Ki values>1000 nM (Table 1). Compounds TZ64-55, TZ64-82, TZ64-102, TZ64-105, TZ64-19, TZ66-16, TZ66-25 and TZ64-91 were found to have high potency.

TABLE 1

| Compound | Thioflavin T assay $K_i$ (nM) [a] | Log P [b] |
|---|---|---|
| 26 | >1000 | 3.42 |

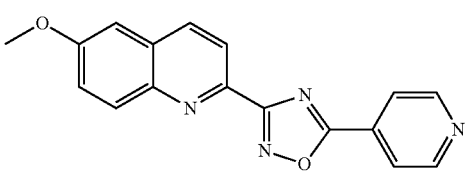 [SMILES: COc1ccc2nc(-c3noc(-c4ccncc4)n3)ccc2c1]

TABLE 1-continued

| Compound | | Thioflavin T assay $K_i$ (nM)[a] | Log P[b] |
|---|---|---|---|
| 27 | [6-methoxyquinolin-2-yl with 1,2,4-oxadiazole linked to 2-methoxypyridin-4-yl] | 630 | 4.01 |
| 28 | [6-(2-fluoroethoxy)quinolin-2-yl with 1,2,4-oxadiazole linked to 2-methoxypyridin-4-yl] | 17 | 4.20 |
| 29 | [6-(methoxymethoxy)quinolin-2-yl with 1,2,4-oxadiazole linked to 2-methoxypyridin-4-yl] | >1000 | 4.13 |
| 30 | [6-isopropoxyquinolin-2-yl with 1,2,4-oxadiazole linked to 2-methoxypyridin-4-yl] | >1000 | 4.67 |
| 31 | [6-methoxyquinolin-2-yl with 1,2,4-oxadiazole linked to imidazo[1,2-a]pyridine] | >1000 | 3.62 |
| 32 | [6-isopropoxyquinolin-2-yl with 1,2,4-oxadiazole linked to imidazo[1,2-a]pyridine] | >1000 | 4.28 |
| 33 | [6-(2-fluoroethoxy)quinolin-2-yl with 1,2,4-oxadiazole linked to imidazo[1,2-a]pyridine] | >1000 | 3.81 |
| 34 | [6-(methoxymethoxy)quinolin-2-yl with 1,2,4-oxadiazole linked to imidazo[1,2-a]pyridine] | >1000 | 3.74 |
| TZ64-55 | [6-nitroquinolin-2-yl-NH-(6-methoxypyridin-3-yl)] | 15 | 3.41 |

TABLE 1-continued

| Compound | | Thioflavin T assay $K_i$ (nM)[a] | Log P[b] |
|---|---|---|---|
| TZ64-82 | 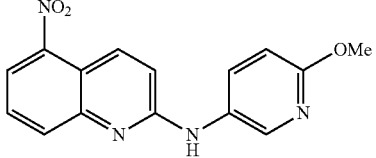 [SMILES: COc1ccc(Nc2ccc3c([N+](=O)[O-])cccc3n2)cn1] | 18 | 3.71 |
| TZ64-102 | 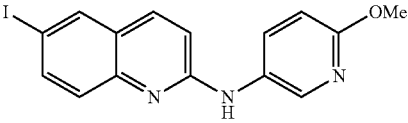 [SMILES: COc1ccc(Nc2ccc3cc(I)ccc3n2)cn1] | 12 | 4.91 |
| TZ64-105 | 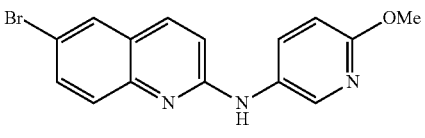 [SMILES: COc1ccc(Nc2ccc3cc(Br)ccc3n2)cn1] | 10 | 4.38 |
| TZ64-19 | 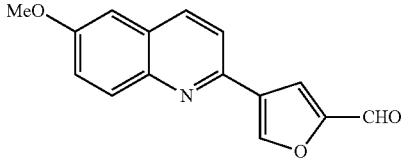 [SMILES: COc1ccc2nc(-c3coc(C=O)c3)ccc2c1] | 10.4 | 2.45 |
| TZ66-16 |  | 11 | 4.21 |
| TZ66-25 | 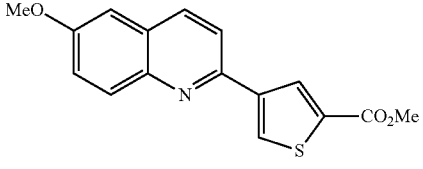 [SMILES: COC(=O)c1cc(-c2ccc3cc(OC)ccc3n2)cs1] | 17 | 3.89 |
| TZ64-91 | 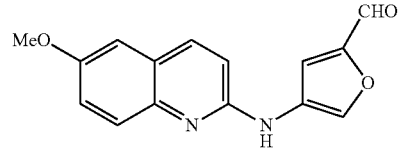 [SMILES: COc1ccc2nc(Nc3coc(C=O)c3)ccc2c1] | 18 | 2.53 |

[a] Ki values (mean ± SD nM) were determined in at least three experiments.
[b] Calculated by ChemBioDraw Ultra 16.0

Based on the results from Table 1, Compound 28 was chosen for further Fluorine-18 radiolabeling to further evaluate its binding potency via a direct radioligand binding method that provides higher accuracy and sensitivity than thioflavin T method. In addition, other compounds, including radiolabeled TZ64-44, TZ61-84 and TZ55-107, were evaluated using these direct radioligand binding assays to examine their binding efficacy towards α-synuclein fibrils, and tissue samples from patients with Parkinson's disease (PD) or Alzheimer's disease (AD). Radiosynthesis of radiolabeled versions of these compounds as well as the methodology behind radioligand binding assays are provided in the following examples.

Example 34. General Procedures for [$^{18}$F] Radiolabeling

Production of [$^{18}$F]Fluoride

[$^{18}$F]Fluoride was produced by $^{18}$O (p, n)$^{18}$F reaction through proton irradiation of enriched $^{18}$O water (95%) using a RDS111 cyclotron (Siemens/CTI Molecular Imaging, Knoxville, TN). [$^{18}$F]Fluoride is first passed through an ion-exchange resin and then is eluted with 0.02 M potassium carbonate ($K_2CO_3$) solution.

A General Procedure for the Radiosynthesis of [$^{18}$F]Fluoroethyl Tosylate

A sample of ~200 mCi [$^{18}$F]/fluoride was added to a reaction vessel containing $K_{222}$ (6-8 mg). The syringe was washed with 2×0.4 mL ethanol. The resulting solution was evaporated under nitrogen flow with a bath temperature of 110° C. To the mixture acetonitrile (3×1.0 mL) was added and water was azeotropically removed by evaporation. After all the water was removed, 5-6 mg of the corresponding precursor 1,2-ethylene ditosylate was dissolved in acetonitrile (200 μL) under vortex, and the precursor solution was transferred into the reaction vessel containing [$^{18}$F]fluoride/K$_{222}$/K$_2$CO$_3$. The reaction tube was capped and the reaction mixture was briefly mixed, and then subjected to heating in an oil bath that was preheated to 110° C. for 10 min.

After heating for 10 minutes, the reaction mixture was diluted with 3.0 mL of HPLC mobile phase (50:50 Acetonitrile/0.1 M ammonium formate buffer (pH ~6.5)) and passed through an alumina Neutral Sep-Pak Plus cartridge. The crude product was then loaded onto an Agilent SB-C18 semi-preparative HPLC column (250 mm×10 mm) with a UV detector set at 254 nm. The HPLC system used a 5 mL injection loop. With 50:50 Acetonitrile/0.1 M ammonium formate buffer (pH ~6.5) as eluent at 4.0 mL/min flow rate, the retention time of the product was 10-11 min. The retention time of the precursor was 23-24 min. In situ monitored by the radioactivity detector, the HPLC collection was diluted with ~50 mL sterile water and the diluted collection went through a C-18 Sep-Pak Plus cartridge to trap the [$^{18}$F]fluoroethyl tosylate on the Sep-Pak. The trapped product was eluted with diethyl ether (3 mL).

The eluted solution formed two phases, the top ethereal phase was transferred out, and the bottom aqueous phase was extracted with another 1 mL of ether. The combined ether solution was passed through a set of two stacked Sep-Pak Plus dry cartridges into a reaction vessel. After the ether was evaporated with a nitrogen stream at 25° C. The dried tracer was used for next reaction.

General Procedure for the Conjugation of [$^{18}$F]Fluoroethyl Tosylate with Precursor 1.0-1.5 mg (4-5 mg for $^{19}$F-MNI659) of precursor was dissolved in appropriate solvent and was transferred to a vial containing related base. After vortexing for 1 min, the solution was added into the reaction tube containing the activity. The tube was capped and briefly swirled with a vortex, and then was kept at appropriate temperature for 10 min or 15 min. Subsequently, the residual was diluted with 3 mL HPLC mobile phase and loaded onto a Semi-Prep HPLC system for purification. The HPLC system contains a 5 mL injection loop, a UV detector at 254 nm and a radioactivity detector, at 4.0 mL/min flow rate. After the HPLC collection was diluted with ~50 mL sterile water, the product was trapped on a C-18 Sep-Pak Plus cartridge and washed with 20 mL water. The trapped product was eluted with ethanol (0.6 mL) followed by 5.4 mL of 0.9% saline. After sterile filtration into a glass vial, the final product was ready for quality control (QC) analysis and animal studies. An aliquot of sample was assayed by an analytical HPLC system. The sample was authenticated by co-injecting with the cold standard solution. The radiochemical purity was >99%. The entire procedure took ~2 h for two-step radiolabeling and 3 hours for three-step radiolabeling.

Example 35. Radiolabeling $^{18}$F-TZ-61-44

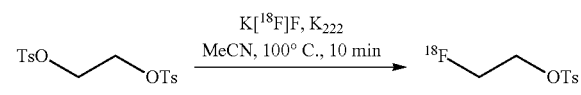

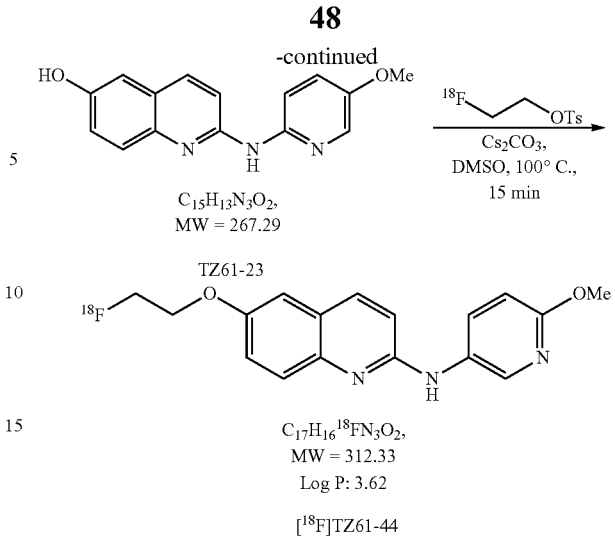

[$^{18}$F]TZ61-44

To the reaction vial containing dried 2-[$^{18}$F]fluoroethyl tosylate was added 2-3 mg of precursor, 3-4 mg of Cs$_2$CO$_3$ in a solution of 300 μL DMSO. The reaction was placed in a 100° C. oil-bath and heated for 15 min, shaking occasionally. The reaction vessel was removed from the oil-bath, quenched with 3.0 mL of the HPLC mobile phase (42% MeCN in 58% 0.1 M ammonium formate buffer, pH=4.5), and injected onto the HPLC column (Agilent SB-C18 250× 9.6 mm, 5μ, UV=254 nm, 4.0 mL/min). The desired fraction was collected into a water bottle prefilled with 50 mL steric water. The dilute fraction was passed through a C18 Sep-pak and rinsed with another 20 mL steric water. The product was eluted with USP grade ethanol and delivered for competitive binding assay. The product was analyzed for radioactivity and the results are shown in Table 2 below.

TABLE 2

| Study done | Product activity | Radiochemical purity | Delivery | QC ppm | SA (Ci/mmol) |
|---|---|---|---|---|---|
| NHP scan on Chong and binding assay | 34.1 mCi | >99% | 20.6 + 2.4 | 0.22 | 5203 |

Example 36. General Procedures for $^{11}$C Radiolabeling

Production of [$^{11}$C]CH$_3$I

Production of [$^{11}$C]CH$_3$I followed the reported method. Briefly, [$^{11}$C]CH$_3$I was produced on-site from [$^{11}$C]CO$_2$ using a GE PETtrace MeI Microlab. Up to 1.4 Ci of [$^{11}$C]carbon dioxide was produced from the JSW BC-16/8 cyclotron by irradiating a gas target of 0.5% O$_2$ in N$_2$ for 15-30 min with a 40 μA beam of 16 MeV protons in the Barnard Cyclotron Facility of Washington University School of Medicine. After the GE PETtrace MeI Microlab system converted the [$^{11}$C]CO$_2$ to [$^{11}$C]CH$_4$ using a nickel catalyst [Shimalite-Ni (reduced), Shimadzu, Japan P. N. 221-27719] in the presence of hydrogen gas at 360° C.; the [$^{11}$C]CH$_4$ was further converted to [$^{11}$C]CH$_3$I by reaction with iodine in the gas phase at 690° C. Approximately 12 min following the end-of-bombardment (EOB), several hundred millicuries of [$^{11}$C]CH$_3$I were delivered in the gas phase to the hot cell where the radiosynthesis was accomplished.

A General Procedure for [11]C-Radiolabeling

[11C]CH₃I was bubbled for a period of 2-3 min into a solution of precursor (1-2 mg) in appropriate solvent (0.25 mL) containing 3.0-5.0 μL of base solution (5.0 N) at room temperature. When the trap of radioactivity was completed, the sealed reaction vessel was heated at appropriate temperature for 5 min. After the heating source was removed, 1.75 mL of the HPLC mobile phase was added into to the reaction vessel. The mixture was loaded onto a reversed phase HPLC system to purify the mixture. Under these conditions, the product was collected into a vial that contained 50 mL aseptic water. After finishing the collection, the collected fraction was passed through a C-18 Plus Sep-Pak® cartridge to remove the mobile phase solvent, whereby target tracer was retained on the cartridge. Then the Sep-Pak cartridge was rinsed using 20 mL of sterile water. Finally, the tracer trapped on the Sep-Pak® was eluted with 0.6 mL of ethanol, following with 5.4 mL 0.9% sodium chloride solution, passing through a 0.22μ (Whatman Puradisc 13 mm syringe filter) sterile filter into a sterile pyrogen-free glass vial for delivery. For quality control, an aliquot of sample was assayed by an analytical HPLC system, UV at 254 nm. The sample was authenticated by co-injecting with the corresponding cold standard solution. The radiochemical purity was >99%. The radiosynthesis typically took 1 hour.

Example 37. Radiolabeling of [11]C-TZ55-107

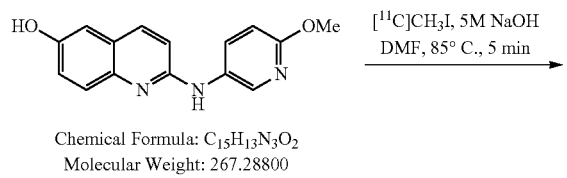

Chemical Formula: $C_{15}H_{13}N_3O_2$
Molecular Weight: 267.28800

TZ61-23

[11C]CH₃I, 5M NaOH
DMF, 85° C., 5 min

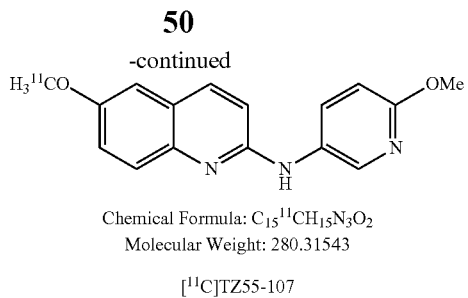

Chemical Formula: $C_{15}{}^{11}CH_{15}N_3O_2$
Molecular Weight: 280.31543

[11C]TZ55-107

The demethylphenol precursor TZ61-23 (~1-3 mg) was dissolved into 180 μL anhydrous DMF, followed by adding 2 μL of 5 nM into the solution, vortexed. [11C]CH₃OI was bubbled into the abovementioned solution within 2-4 minutes and the reaction was heated at ~85° C. for ~5 min and then cooled down to room temperature. The reaction mixture was diluted with the HPLC mobile phase (1.8 mL, 48% MeCN+52% 0.1 M AMF; pH=4.5) and then uploaded onto reverse phase HPLC semi-preparative for purification. The radioactive product was diluted with sterile water and then passed through the C-18 light cartridge (Agilent Zorbax, 250×9.6 mm, 5μ, UV-254 nm, 4.0 mL/min). The final project was ringed into a dose vial using 0.5 mL absolutely ethanol, which is ready for transferring into biological lab for binding characterization. The product was analyzed for radioactivity and the results are depicted in Table 3 below.

TABLE 3

| Study done | Product activity | Radiochemical purity | Delivery | QC ppm | SA (Ci/mmol) |
|---|---|---|---|---|---|
| NHP scan on Bud and Binding assay | 58.2 mCi | >99% | 27.8 mCi + 5.4 mCi | 1.4 | 1014 |

Example 38. Radiolabeling of [125I]TZ-61-84

Cold Reaction

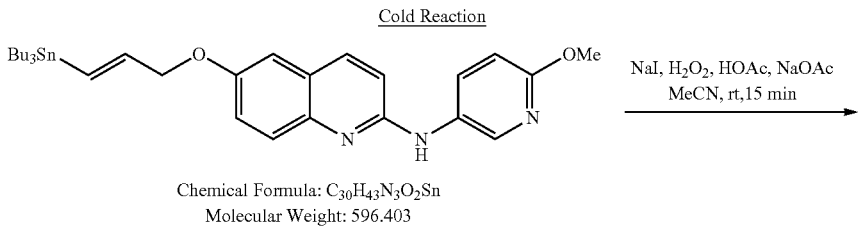

Chemical Formula: $C_{30}H_{43}N_3O_2Sn$
Molecular Weight: 596.403

TZ61-80

NaI, H₂O₂, HOAc, NaOAc
MeCN, rt, 15 min

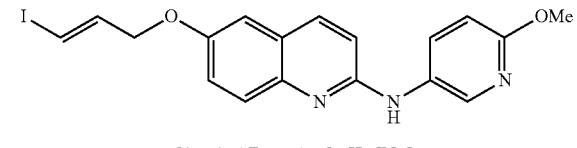

Chemical Formula: $C_{18}H_{16}IN_3O_2$
Molecular Weight: 433.249

TZ61-84

-continued
Hot reaction

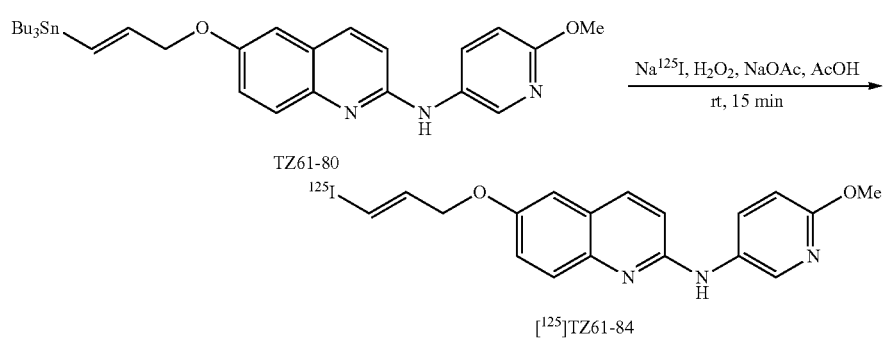

To a mixture of tin precursor TZ61-80 (200 μg, 0.34 μmol) in 50 μL acetonitrile was added a solution of sodium acetate in glacial acetic acid (50 μL, 5%, w/v). [$^{125}$I]NaI (2.3 mCi, 20 μL in 0.01 M NaOH) was added to the reaction vial, followed by a solution of acetic acid and 30% hydrogen peroxide (50 μL, 2/1, v/v). After the mixture was stirred at room temperature for 15 min, the mixture was diluted with acetonitrile (100 μL) and was loaded onto a reversed HPLC column for purification (Agilent C18 column, 250×10 mm, mobile phase consisting of acetonitrile in 0.1 M ammonium formate, 65/35, v/v, pH 4.5, flow rate 3.0 mL/min, UV detection wavelength 254 nm). The retention times for the product [$^{125}$I]TZ61-84 was 17-18 min.

Example 39. Radiosynthesis of [$^{18}$F]28

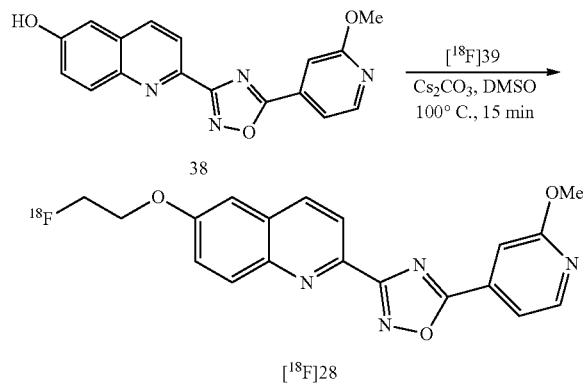

[$^{18}$F]28 was prepared from the non-radioactive precursor 38 (synthesized as described in Example 32) using $^{18}$F fluoroethyl tosylate (39). [$^{18}$F]Fluoride produced in Washington University School of Medicine Cyclotron Facility was first passed through an ion-exchange resin and was then eluted with 0.02 M potassium carbonate (K$_2$CO$_3$) solution. 1.0-1.5 mg of the appropriate phenol precursor (38) was dissolved in Cs$_2$CO$_3$ saturated solution in anhydrous DMSO (200 μL). After vortexing for 1 min, the phenol precursor solution was added into a reaction tube containing [$^{18}$F] fluoroethyl tosylate, which was readily prepared as described in example 34. The reaction vessel was capped and briefly swirled, and then kept at 100° C. for 15 min. Subsequently, the residue was diluted with 3 mL of the appropriate HPLC mobile phase (acetonitrile in 0.1 M ammonium formate, 51/49, v/v, pH 4.5 for [$^{18}$F]28) then loaded onto a semi-preparative HPLC (Agilent Zorbax, SB-C18, 250×9.6 mm, 5μ) system for purification at 4.0 mL/min flow rate. The HPLC system contains a 5 mL injection loop, a UV detector at 254 nm and a radioactivity detector. After HPLC collection of the desired fraction, (the retention time for [$^{18}$F]28 was 22 min), the product fraction was diluted with ~50 mL sterile water. The product was then trapped on a C-18 Sep-Pak Plus cartridge and washed with 20 mL water. The trapped product was eluted with ethanol (0.6 mL) followed by 5.4 mL of 0.9% saline. After passing through a 0.22μ sterile filter into a sterile pyrogen-free glass vial, the final product was ready for quality control (QC) analysis and direct binding assays. For quality control, an aliquot of sample was assayed by an analytical HPLC system. The sample was authenticated by co-injecting with the reference standard solution. The entire procedure took ~2 h for two-step radiolabeling. [$^{18}$F]28 was produced in 30±4% yield, specific activity>37 GBq/μmol (decay corrected to the end of synthesis).

Example 40. Radioligand Binding Assays

The equilibrium dissociation constant (K$_d$) for a series of compounds was determined using direct radioactive competitive binding assays (homologous or heterologous) with either recombinant α-synuclein fibrils or brain tissue homogenates from AD cases.

Preparation of Recombinant α-Synuclein and Tau Protein

Recombinant protein was produced in *E. coli* using protocols based on previously described methods for α-synuclein [Giasson, B. I., et al., "Mutant and wild type human alpha-synucleins assemble into elongated filaments with distinct morphologies in vitro," 1999, *J Biol. Chem.*, 274: 7619-7622; Huang, C., et al., "A new method for purification of recombinant human alpha-synuclein in *Escherichia coli*," 2005, Protein Expr Purif, 42:173-177; Yu, L., et al, "Synthesis and in vitro evaluation of á-synuclein ligands," 2012, *Bioorg. Med. Chem.*, 20:4625-4634] and tau [Li, W., et al., "Characterization of two VQIXXK motifs for tau fibrillization in vitro," 2006, *Biochemistry*, 45:15692-15701]. BL21 (DE3)RIL *E. coli* were transformed with a pRK172 bacterial expression plasmid containing the human α-synuclein coding sequence. Freshly transformed BL21 colonies were inoculated into 2 L baffled flasks containing 250 ml sterilized TB (1.2% bactotryptone, 2.4% yeast extract, 0.4% glycerol, 0.17 M KH$_2$PO$_4$, 0.72 M K$_2$HPO$_4$) with 50 μg/ml ampicillin, and incubated overnight at 37° C. with shaking. Overnight cultures were centrifuged at 3,900×g for 10 min at 25° C. and the bacterial pellets were resuspended by gentle vortexing in 20 ml osmotic shock buffer (30 mM Tris-HCl, 2 mM EDTA, 40% Sucrose, pH 7.2) and then incubated at room temperature for 10 min. The cell suspension was then centrifuged at 8,000×g for 10 min at 25° C. and the pellet was resuspended in 22.5 ml cold $H_2O$ before adding 9.4 µl 2 M $MgCl_2$ to each tube. The suspension was incubated on ice for 3 min prior to centrifugation at 20,000×g for 15 min at 4° C. After the supernatant was transferred to a fresh tube, streptomycin was added to a final concentration of 10 mg/ml and centrifuged at 20,000×g for 15 min at 4° C. The supernatant from this step was collected and dithiothreitol (DTT) and Tris-HCl pH 8.0 were added to final concentrations of 1 mM and 20 mM respectively, before boiling for 10 min to precipitate heat-sensitive proteins, which were pelleted at 20,000×g for 15 min at 4° C. The supernatant was collected and filtered through a 0.45 µm surfactant-free cellulose acetate filter (Corning) before loading onto a 1 ml DEAE Sepharose column equilibrated in 20 mM Tris-HCl pH 8.0, 1 mM EDTA, and 1 mM DTT. The DEAE column was washed with 20 mM Tris-HCl pH 8.0, 1 mM EDTA, 1 mM DTT before eluting α-synuclein protein in 20 mM Tris-HCl pH 8.0 buffer with 1 mM EDTA, 1 mM DTT and 0.3 M NaCl. Purified α-synuclein protein was dialyzed overnight in 10 mM Tris-HCl pH 7.6, 50 mM NaCl, 1 mM DTT. Preparations contained greater than 95% α-synuclein protein as determined by sodium dodecyl sulfate polyacrylamide gel electrophoresis (SDS-PAGE) and bicinchoninic acid (BCA) protein assay (Thermo Scientific, Rockford, IL), with a typical yield of 30 mg protein per 250 ml culture.

Recombinant tau protein was produced in *E. coli*. BL21 (DE3)RIL *E. coli* were transformed with a pRK172 bacterial expression plasmid encoding a human tau fragment containing the four microtubule binding repeats (amino acids 243-375) [Frost, B., et al, "Propagation of tau misfolding from the outside to the inside of a cell," 2009, *J Biol. Chem.* 284: 2845-12852]. Cultures were inoculated and grown overnight as above for α-synuclein protein production. Purified tau protein was prepared using the method described in reference [Li, W., et al., "Characterization of two VQIXXK motifs for tau fibrillization in vitro," 2006, *Biochemistry*, 45:15692-15701] and dialyzed overnight in 100 mM sodium acetate pH 7.0.

Preparation of Recombinant α-Synuclein Fibrils

Purified recombinant α-synuclein monomer (2 mg/ml) was incubated in 20 mM Tris-HCl, pH 8.0, 100 mM NaCl for 72 h at 37 C with shaking at 1000 rpm in an Eppendorf Thermomixer. To determine the concentration of fibrils, the fibril reaction mix was centrifuged at 15,000×g for 15 min to separate fibrils from monomer. The concentration of α-synuclein monomer in the supernatant was determined in a BCA protein assay according to the manufacturer's instructions, using a bovine serum albumin (BSA) standard curve. The measured decrease in α-synuclein monomer concentration was used to determine the concentration of fibrils in the 72 h fibril reaction mixture.

Preparation of $A\beta_{1-42}$ Fibrils

Synthetic $A\beta_{1-42}$ peptide (1 mg) (Bachem, Torrance, CA) was first dissolved in 50 µl DMSO. An additional 925 µl of $mQ-H_2O$ was added. Finally, 25 µl 1M Tris-HCl pH 7.6 was added to bring the final peptide concentration to 222 µM (1 mg/ml) [16]. The dissolved peptide was incubated for 30 h at 37° C. with shaking at 1000 rpm in an Eppendorf Thermomixer. Fibril formation was confirmed by ThioT fluorescence. To determine the concentration of fibrils, the fibril reaction mix was centrifuged at 15,000×g for 15 min to separate fibrils from monomer. The concentration of Aβ monomer in the supernatant was determined in a BCA protein assay using a BSA standard curve that contained DMSO at a percentage equivalent to the samples.

Preparation of Recombinant Tau Fibrils

Purified recombinant tau monomer (300 ng/ml) was incubated in 20 mM Tris-HCl pH 8.0, 100 mM NaCl, 25 µM low molecular weight heparin, 0.5 mM DTT for 48 h at 37° C. with shaking at 1000 rpm in an Eppendorf Thermomixer. To determine the concentration of fibrils, the fibril reaction mixer was centrifuged at 15,000×g for 15 min to separate fibrils from monomer. The concentration of tau monomer in the supernatant was determined in a BCA protein assay along with a BSA standard curve. The measured decrease in monomer concentration was used to determine the concentration of tau fibrils in the 48 h fibril reaction mixture.

Preparation of α-Synuclein, $A\beta_{1-42}$, and Tau Fibrils for Binding and Competition Assays The prepared fibril mixture was centrifuged at 15,000×g for 15 min to prepare fibrils for binding assays. The supernatant was discarded and the fibril pellet was resuspended in 30 mM Tris-HCl pH 7.4, 0.1% BSA to achieve the desired concentration of fibrils for use in the assay.

Acquisition of Human Post-Mortem Tissue Samples for Binding and Competition Assays.

Brain tissue samples were selected from an autopsy case series of patients evaluated for parkinsonism by movement disorders specialists at the Movement Disorders Center of Washington University School of Medicine in St. Louis. The clinical diagnosis of idiopathic PD was based on modified United Kingdom Parkinson's Disease Society Brain Bank clinical diagnostic criteria with clear clinical response to levodopa [Hughes, A. J., et al, "Accuracy of clinical diagnosis of idiopathic Parkinson's disease: a clinico-pathological study of 100 cases," 1992, *J. Neurol. Neurosurg. Psychiatry*, 55:181-184]. Dementia was determined by a movement disorders specialist based on clinical assessment of cognitive dysfunction sufficiently severe to impair activities of daily living, with further evaluation of cognitive impairment using the AD8 and Mini-Mental Status Exam (MMSE) [Galvin, J. E., et al., "The AD8: a brief informant interview to detect dementia," 2005, Neurology 65:559-564; Folstein, M. F., et al., ""Mini-mental state". A practical method for grading the cognitive state of patients for the clinician," 1975, *J Psychiatr Res*, 12:189-198]. LB stage was assessed at autopsy using a PD staging scale (range: 0, 1-6) [Braak, H., et al., "Stages in the development of Parkinson's disease-related pathology," 2004, *Cell Tissue Res.*, 318:121-134]. PD cases were selected based on a clinical diagnosis of PD plus dementia, Braak LB stage 5-6 pathology, and the absence of significant Aβ or tau pathology determined by immunohistochemistry. Control cases were selected based on the absence of α-synuclein, Aβ and tau pathology. Samples were used from both male and female subjects.

Preparation of Human Brain Tissue for In Vitro Binding and Competition Studies

Grey matter was isolated from frozen postmortem frontal cortex tissue by dissection with a scalpel. To prepare insoluble fractions, dissected tissue was sequentially homogenized in four buffers (3 ml/g wet weight of tissue) with glass Dounce tissue grinders (Kimble): 1) High salt (HS) buffer: 50 mM Tris-HCl pH 7.5, 750 mM NaCl, 5 mM EDTA; 2) HS buffer with 1% Triton X-100; 3) HS buffer with 1% Triton X-100 and 1 M sucrose; and 4) phosphate buffered saline (PBS). Homogenates were centrifuged at 100,000×g after each homogenization step and the pellet was resuspended and homogenized in the next buffer in the sequence. For comparison in initial binding studies, crude tissue homogenates were also prepared by homogenization of tissue in only PBS.

General Procedure for Direct Binding (Homologous Competition) Assays.

These direct binding assays used a fixed concentration of either fibrils or PD/AD tissue and the radioligand (e.g., [$^{18}$F]28) and varying concentration ranges of corresponding homologous non-radiolabeled standard reference compound. In brief, the standard homologous reference compound was diluted in 30 mM Tris-HCl pH 7.4, 0.1% BSA. Reactions were incubated at 37° C. for 1 h before quantifying bound radioligand. Bound and free radioligand were separated by vacuum filtration through 1.0 μm glass fiber filters in 96-well filter plates (Millipore), followed by three 200 μL washes with ice-cold assay buffer. Filters containing the bound ligand were mixed with 150 μL of Optiphase Supermix scintillation cocktail (PerkinElmer) and counted immediately. All data points were performed in triplicate. The dissociation constant ($K_d$) and the maximal number of binding sites ($B_{max}$) values were determined by fitting the data to the equation. Bound=($B_{max}$*[Radioligand])/([Radioligand]+[Unlabeled compound]+$K_d$)+Bottom by nonlinear regression using Graphpad Prism software (version 4.0), where (Bottom) is nonspecific binding and [Radioligand], [Unlabeled compound], and $K_d$ are expressed in nM.

Example 41. Homologous Competition Binding Assays of α-Synuclein Ligands on PD-Seeded Fibrils, Aβ Fibrils, Banner AD, Banner PD, and α-Synuclein Fibrils The binding efficacies of [$^{18}$F]TZ61-44, [$^{11}$C]TZ61-107, [$^{11}$C]TZ55-81, [$^{11}$C]TZ55-101, [$^{125}$I]TZ64-84, and [$^{18}$F]28 were evaluated on different substrates (PD-seeded fibrils, Aβ fibrils, Banner AD, Banner PD, as indicated) using homologous radioactive binding assays as described in Example 40. The results for [$^{18}$F]TZ61-44 are depicted in FIG. 1A-FIGS. 4F and 6A-6B; for [$^{11}$C]TZ61-107 in FIGS. 7A-9F; for [$^{11}$C]TZ55-81 in FIGS. 10B-10G; for [$^{11}$C]TZ55-101 in FIG. 11B-11D; for [$^{125}$I]TZ64-84 in FIG. 15B-15C; and for [$^{18}$F]28 in FIG. 16A-16B. The $K_d$ as determined during each run is summarized in Table 4, below. Notable trials for [$^{18}$F]TZ61-44, [$^{125}$I]TZ61-84, [$^{18}$F]28 are also described herein.

[$^{18}$F]TZ61-44

Figure 14G:
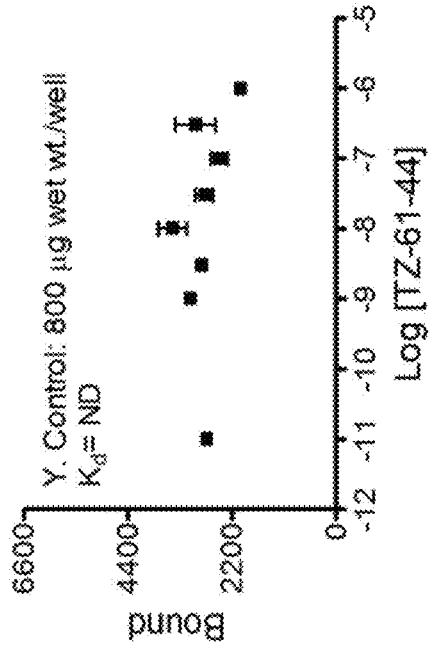
FIG. 14G is a plot of a homologous competition binding assay of [$^{18}$F]TZ61-44 with 400 μg wet wt./well Banner AD tissue.
Figure 14I:
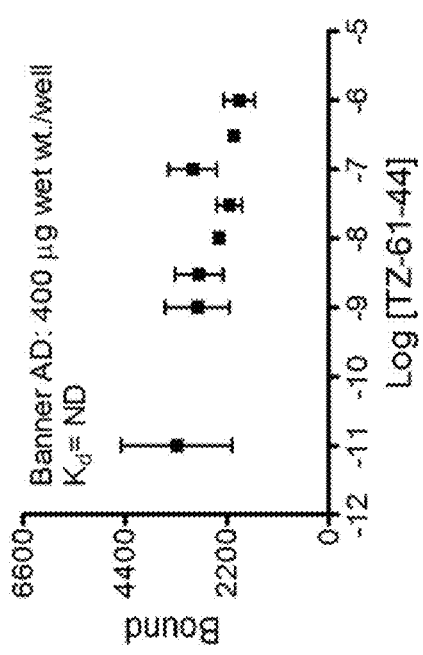
FIG. 14I is a plot of a homologous competition binding assay of [$^{18}$F]TZ61-44 with no substrate.
Figure 14H:
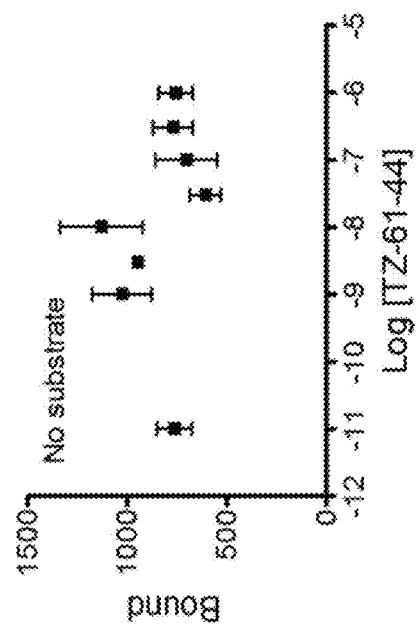
FIG. 14H is a plot of a homologous competition binding assay of [$^{18}$F]TZ61-44 with 800 μg wet wt./well nonspecific control.

Table 4 also includes the results of three separate experiments testing the $K_d$ of [$^{18}$F]TZ61-44 synthesized in three separate batches. Each batch was evaluated independently using the homologous radioactive binding assays described herein. The results for these independent assays are summarized in FIGS. 14B-14I. Notably, using 25 nM of homologous Banner PD-seeded α-synuclein fibrils, the $K_d$ values were determined to be 5.4, 9.7 and 12 nM (FIG. 14B-14D). When 800 μg of Banner PD tissue was used, the $K_d$ values were 3.6 and 6.6 nM (FIGS. 14E and 14F). Notably, [$^{18}$F]TZ61-44 had no significant binding towards 400 μg of Banner AD tissue or 800 μg healthy control tissue (FIG. 14G-14I).

[$^{125}$I]TZ-61-84

Figure 15A:
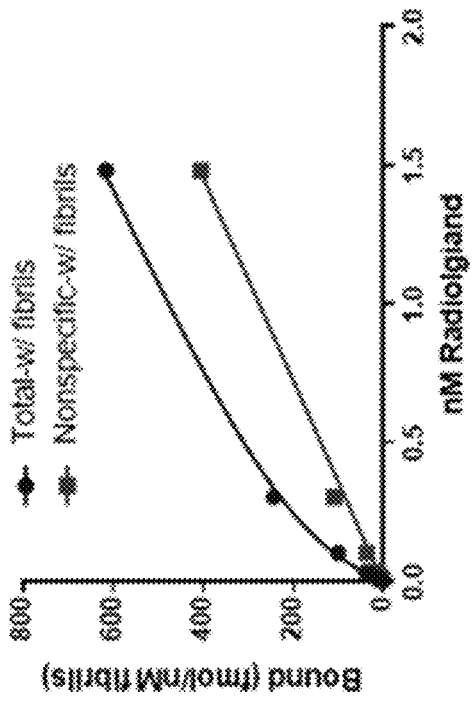
FIG. 15A depicts the structure of [$^{125}$I]TZ61-84.
Figure 15B:
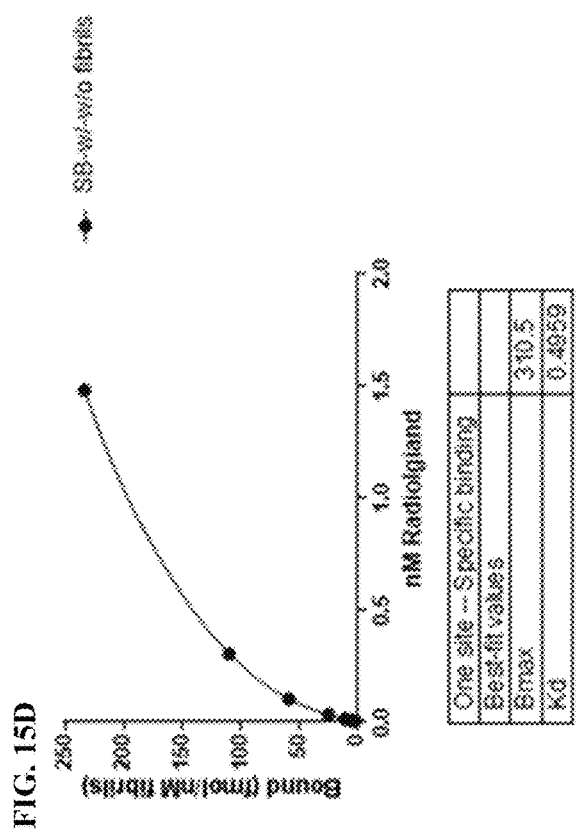
FIG. 15B is a saturation plot of [$^{125}$I]TZ61-84 showing specific and non-specific binding to 100 nM fibrils.
Figure 15C:
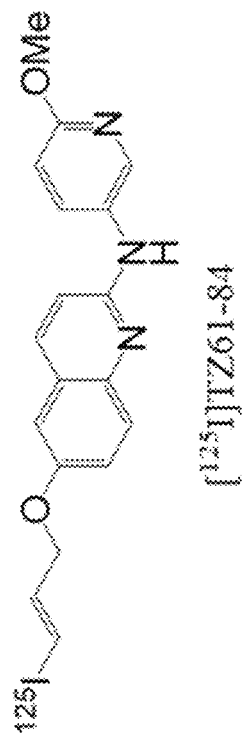
FIG. 15C is a saturation plot of [$^{125}$I]TZ61-84 showing specific and non-specific binding to 100 nM fibrils. Also shown are the calculated $B_{max}$ (259.7) and $K_d$ 0.3376 of [$^{125}$I]TZ61-84 for the experiment.
Figure 15D:
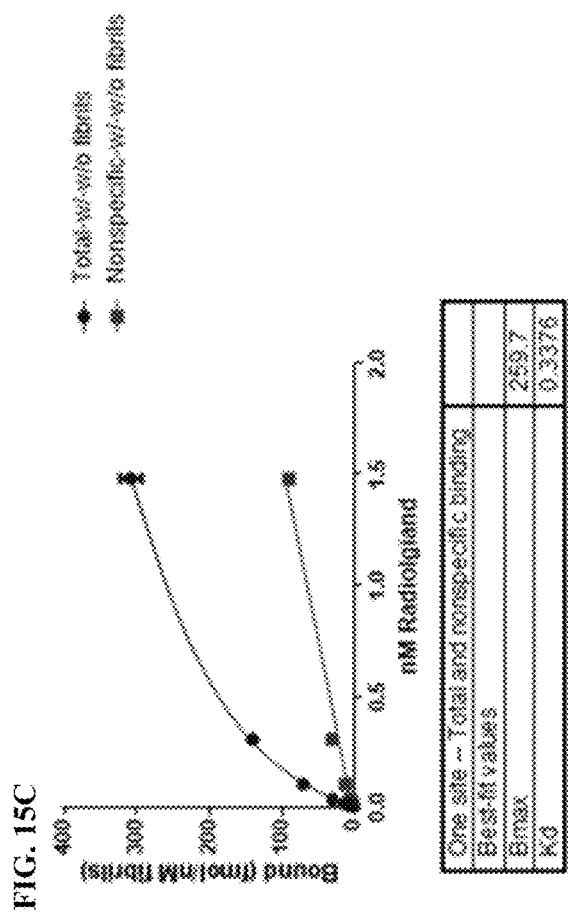
FIG. 15D is a saturation plot of [$^{125}$I]TZ61-84 showing specific and non-specific binding to 100 nM fibrils. Also shown are the calculated $B_{max}$ (310.5) and $K_d$ 0.4959 of [$^{125}$I]TZ61-84 for the experiment.

The binding efficacy ($K_d$) of TZ-61-84 was determined using a modified protocol. Specifically, saturation plots of radiolabeled [$^{125}$I]TZ61-84 were obtained measuring total and nonspecific binding of TZ61-84 to 100 nM Banner seeded fibrils. The results are depicted in FIG. 15B-15D and that TZ61-84 has a high binding affinity to α-synuclein ($K_d$<1 nM).

[$^{18}$F]28

Figure 16B:
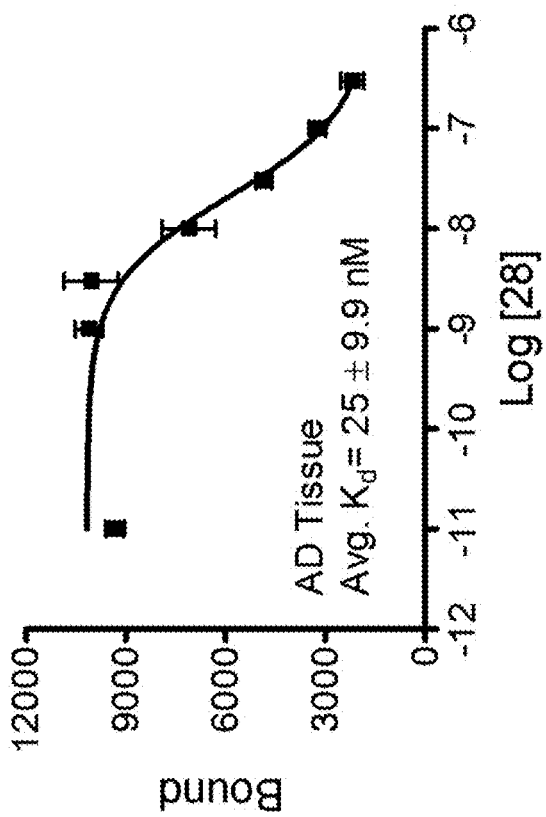
FIG. 16B is a plot of a homologous competition binding assay of [$^{18}$F]28 with AD tissue.

Using the direct radioligand binding assay described herein, the binding affinity of compound [$^{18}$F]28 was determined to be 18 nM towards α-synuclein fibrils (FIG. 16A) and 25 nM towards AD tissue ($B_{max}$=1082 pmol/mg), FIG. 16B. The result found for α-synuclein fibrils is comparable to the $K_i$ value of 17 nM for [$^{18}$F]28 as determined using the Thioflavin T-fluorescence assay (Example 33) but the similar $K_d$ determined for AD tissue suggests that [$^{18}$F]28 lacks selectivity for α-synuclein fibrils over AD tissues.

TABLE 4

Figure 1C:
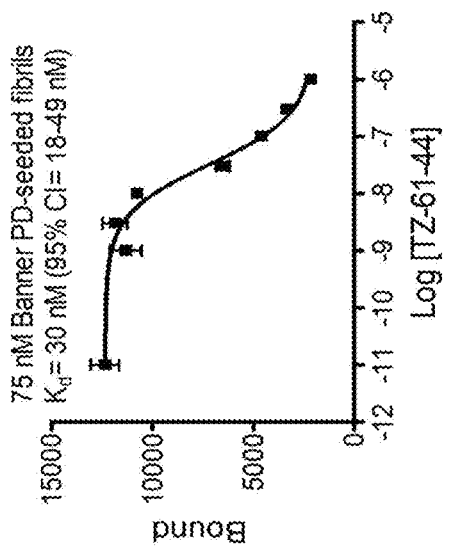
FIG. 1C is a plot of a homologous competition binding assay of [$^{18}$F]TZ61-44 with 25 nM Banner PD seeded fibrils. Specific activity: 1015 Ci/mmol, hot concentration: 2 nM, 10% counts: 14800 cpm. $B_{max}$ was 44 pmol/nmol.
Figure 1B:
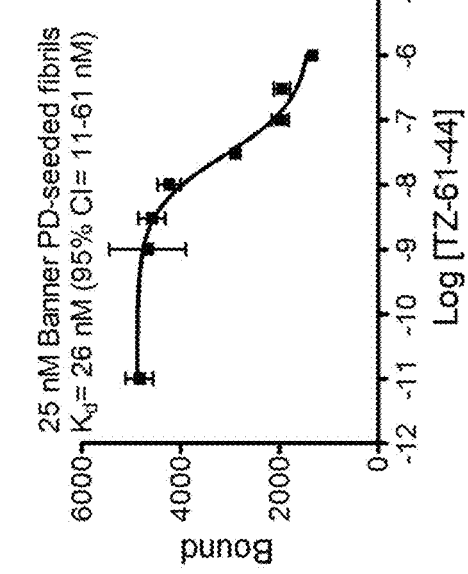
FIG. 1B is a plot of a homologous competition binding assay of [$^{18}$F]TZ61-44 with 25 nM Banner PD seeded fibrils. Specific activity: 1015 Ci/mmol, Hot concentration: 2 nM, 10% counts: 14800. $B_{max}$ was 40 pmol/nmol.
Figure 6A:
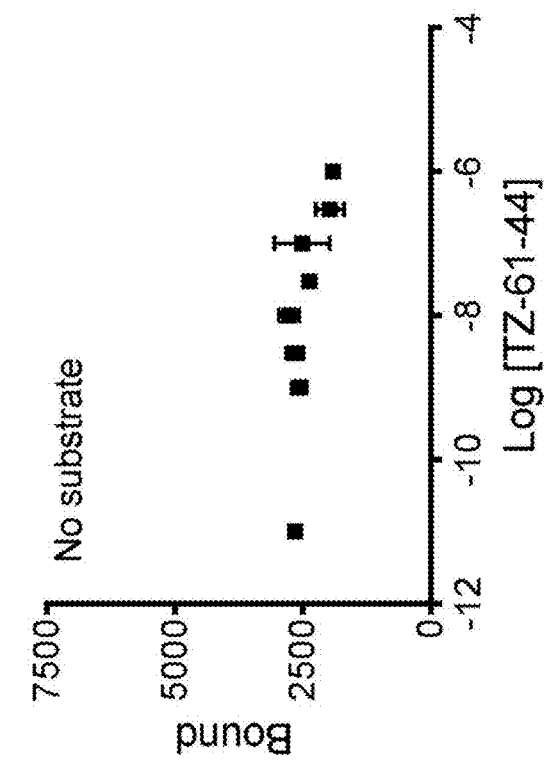
FIG. 6A is a plot of a homologous competition binding assay of [$^{18}$F]TZ61-44 with 25 nM Banner PD-seeded fibrils. Specific activity: 1506 Ci/mmol, hot concentration: 2 nM, 3.3 mCi in 300 µL in 100% ethanol.
Figure 6B:
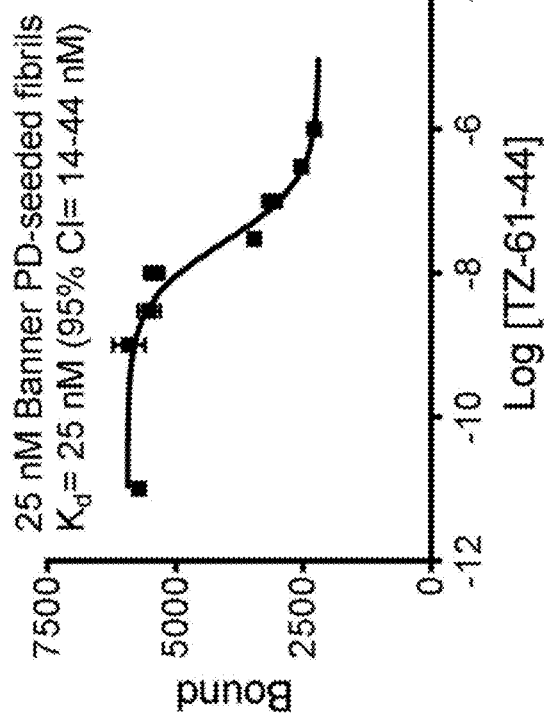
FIG. 6B is a plot of a homologous competition binding assay of [$^{18}$F]TZ61-44 without a substrate. Specific activity: 1506 Ci/mmol, hot concentration: 2 nM, 3.3 mCi in 300 µL in 100% ethanol.
Figure 8A:
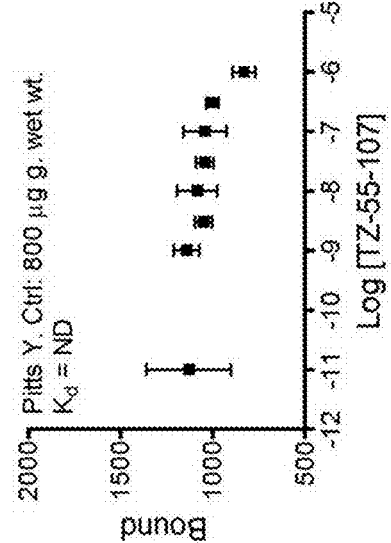
FIG. 8A is a plot of a homologous competition binding assay of [$^{11}$C] TZ55-107 with 800 µg wet wt./well Banner PD. Specific activity: 858 Ci/mmol, hot concentration: 2.9 nM.
Figure 8B:
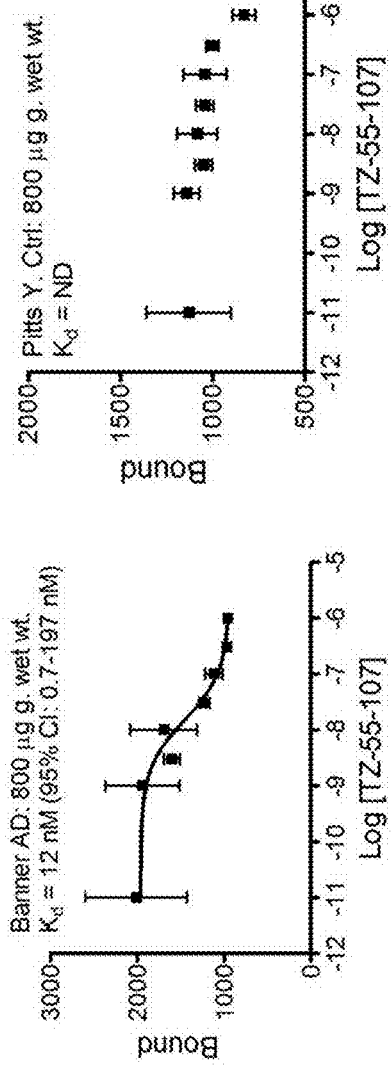
FIG. 8B is a plot of a homologous competition binding assay of [$^{11}$C] TZ55-107 with 800 µg wet wt./well Banner AD. Specific activity: 858 Ci/mmol, hot concentration: 2.9 nM.
Figure 8C:
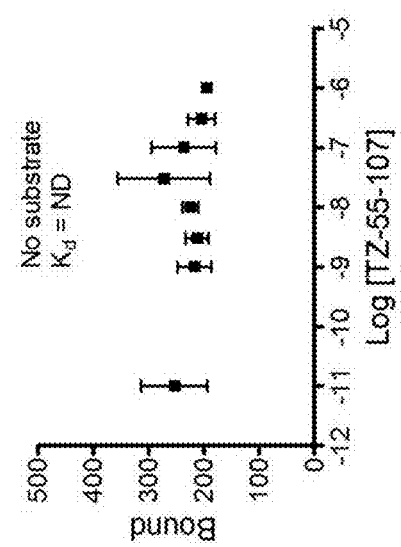
FIG. 8C is a plot of a homologous competition binding assay of [$^{11}$C] TZ55-107 with 800 µg wet wt./well of a nonspecific substrate. Specific activity: 858 Ci/mmol, hot concentration: 2.9 nM.
Figure 8D:
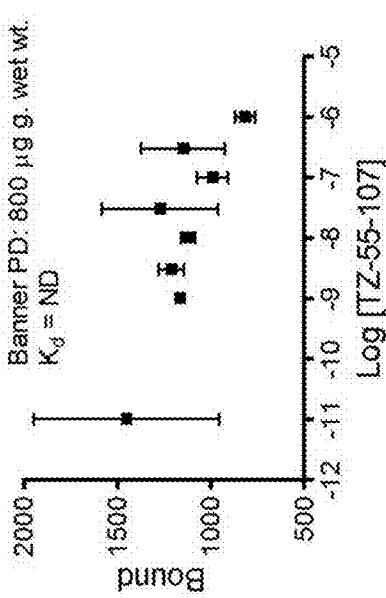
FIG. 8D is a plot of a homologous competition binding assay of [$^{11}$C] TZ55-107 with 150 nM Banner PD-seeded fibrils. Specific activity: 858 Ci/mmol, hot concentration: 2.9 nM.
Figure 8E:
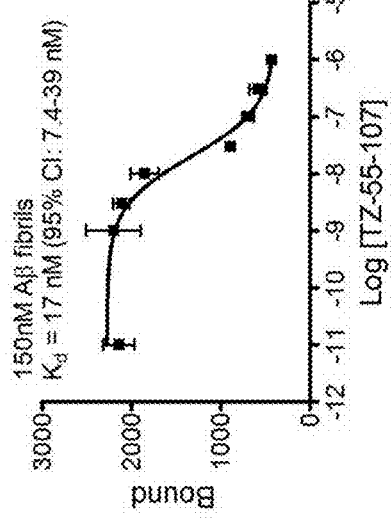
FIG. 8E is a plot of a homologous competition binding assay of [$^{11}$C] TZ55-107 with 150 nM Aβ fibrils. Specific activity: 858 Ci/mmol, hot concentration: 2.9 nM.
Figure 8F:
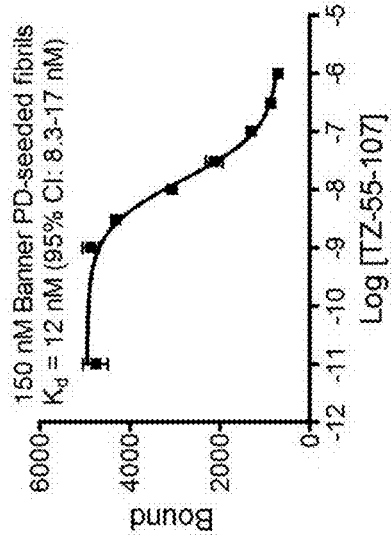
FIG. 8F is a plot of a homologous competition binding assay of [$^{11}$C] TZ55-107 without a substrate. Specific activity: 858 Ci/mmol, hot concentration: 2.9 nM.
Figure 10A:
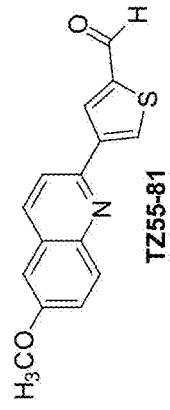
FIG. 10A depicts the structure of TZ55-81.
Figure 10B:
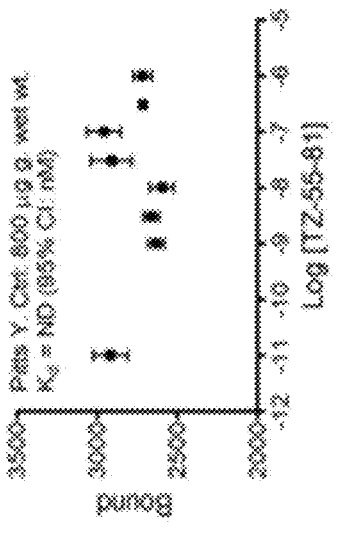
FIG. 10B is a plot of a homologous competition binding assay of [$^{11}$C]TZ55-81 with 800 µg wet. wt of Banner PD. Specific activity: 953 Ci/mmol, hot concentration 2.6 nM.
Figure 10C:
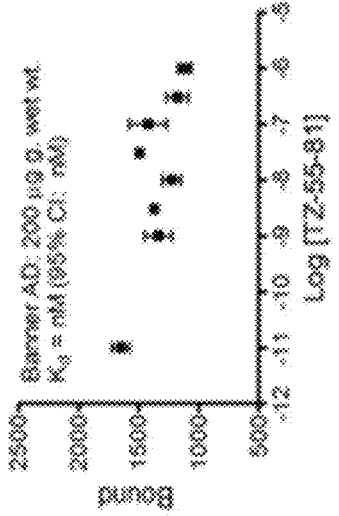
FIG. 10C is a plot of a homologous competition binding assay of [$^{11}$C]TZ55-81 with 200 µg wet. wt of Banner AD. Specific activity: 953 Ci/mmol, hot concentration 2.6 nM.
Figure 10D:
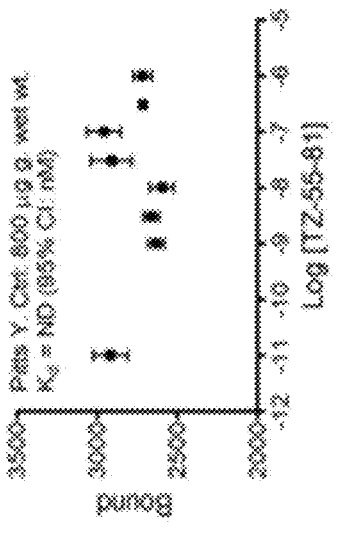
FIG. 10D is a plot of a homologous competition binding assay of [$^{11}$C]TZ55-81 with 800 µg wet. wt of a nonspecific substrate. Specific activity: 953 Ci/mmol, hot concentration 2.6 nM.
Figure 10E:
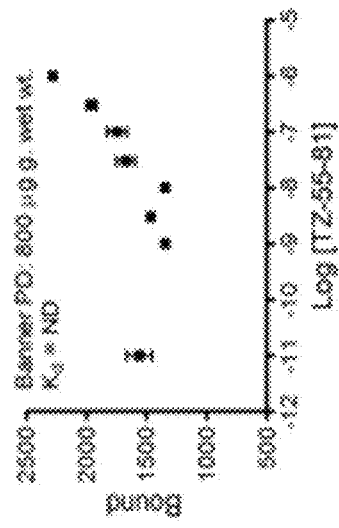
FIG. 10E is a plot of a homologous competition binding assay of [$^{11}$C]TZ55-81 with 150 nM Banner PD-seeded fibrils. Specific activity: 953 Ci/mmol, hot concentration 2.6 nM.
Figure 10F:
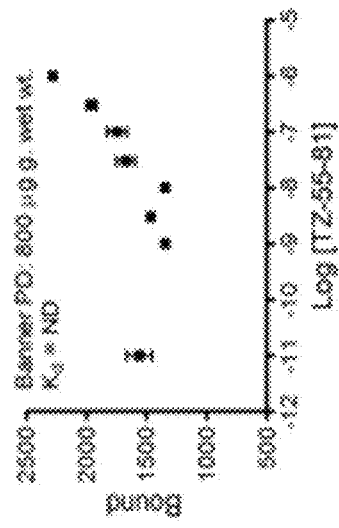
FIG. 10F is a plot of a homologous competition binding assay of [$^{11}$C]TZ55-81 with 150 nM of Aβ fibrils. Specific activity: 953 Ci/mmol, hot concentration 2.6 nM.
Figure 10G:
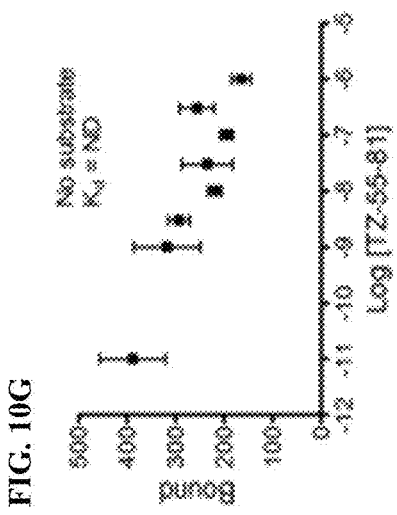
FIG. 10G is a plot of a homologous competition binding assay of [$^{11}$C]TZ55-81 without a substrate. Specific activity: 953 Ci/mmol, hot concentration 2.6 nM.
Figure 16A:
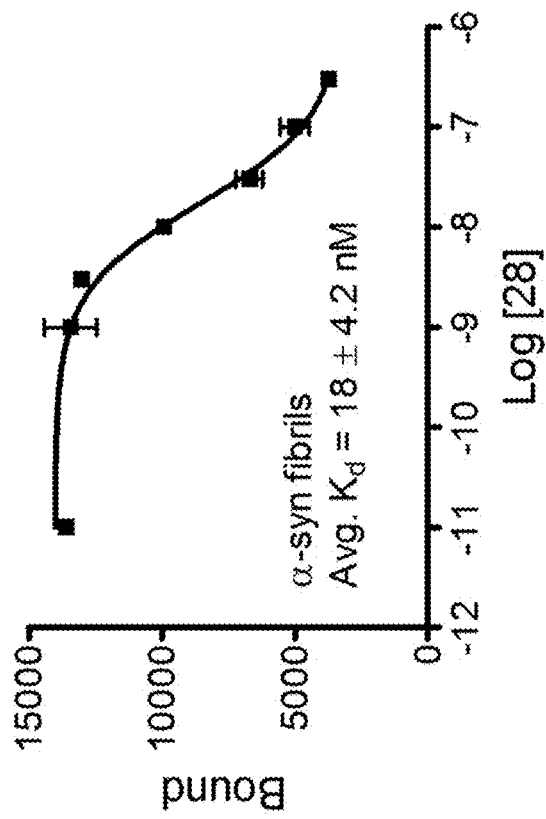
FIG. 16A is a plot of a homologous competition binding assay of [$^{18}$F]28 with α-synuclein fibrils.

| Compound | FIG. | Substrate | Kd (nM) |
|---|---|---|---|
| TZ61-44 | FIG. 1B | 25 nM Banner PD-seeded fibrils | 26 |
| | FIG. 1C | 75 nM Banner PD-seeded fibrils | 30 |
| | FIG. 2A | 400 μg Banner AD (wet wt./well) | ND |
| | FIG. 2B | 800 μg Banner PD (wet wt./well) | 3.6 |
| | FIG. 3A | 800 μg Banner AD (wet wt./well) | 54 |
| | FIG. 3B | 800 μg Banner PD (wet wt./well) | 26 |
| | FIG. 4A | 200 μg Banner AD (wet wt./well) | ND |
| | FIG. 4B | 200 μg Banner PD (wet wt./well) | ND |
| | FIG. 4D | 400 μg Banner AD (wet wt./well) | ND |
| | FIG. 4E | 400 μg Banner PD (wet wt./well) | 60 |
| | FIG. 6A | 25 nM Banner PD-seeded fibrils | 25 |
| | FIG. 14A | 25 nM Banner PD-seeded fibrils | 5.4 |
| | FIG. 14B | 25 nM Banner PD seeded fibrils | 9.7 |
| | FIG. 14C | 25 nM Banner PD seeded fibrils | 12 |
| | FIG. 14D | 800 μg Banner PD (wet wt./well) | 3.6 |
| | FIG. 14E | 800 μg Banner PD (wet wt./well) | 6.6 |
| TZ55-107 | FIG. 7B | 800 μg Banner PD (wet wt./well) | 28 |
| | FIG. 7C | 200 μg Banner AD (wet wt./well) | 35 |
| | FIG. 7E | 150 nM Banner PD seeded fibrils | 11 |
| | FIG. 7F | 150 nM Aβ fibrils | 26 |
| | FIG. 8A | 800 μg Banner PD (wet wt./well) | ND* |
| | FIG. 8B | 800 μg Banner AD (wet wt./well) | 12 |
| | FIG. 8D | 150 nM Banner PD seeded fibrils | 12 |
| | FIG. 8E | 150 nM Aβ fibrils | 17 |
| | FIG. 9A | 800 μg Banner PD (wet wt./well) | 382 |
| | FIG. 9B | 800 μg Banner AD (wet wt./well) | 141 |
| | FIG. 9D | 150 nM Banner PD seeded fibrils | 21 |
| | FIG. 9E | 150 nM Banner PD seeded fibrils | 18 |
| TZ55-81 | FIG. 10B | 800 μg Banner PD (wet wt./well) | ND* |
| | FIG. 10C | 200 μg Banner AD (wet wt./well) | ND* |
| | FIG. 10E | 150 nM Banner PD seeded fibrils | 29 |
| | FIG. 10F | 150 nM Aβ fibrils | 12 |
| | FIG. 15C | 100 nM Banner seeded fibrils | 0.34 |
| | FIG. 15D | 100 nM Banner seeded fibrils | 0.50 |
| TZ61-84 | FIG. 15C | 100 nM Banner seeded fibrils | 0.34 |
| | FIG. 15D | 100 nM Banner seeded fibrils | 0.50 |
| 28 | FIG. 16A | α-synuclein fibrils | 18 |
| | FIG. 16B | AD Tissue | 25 |

*ND: Not determined

Example 42. 3H Radioligand Competition

A series of compounds were synthesized and the $K_i$ (nM) in the presence of Fibrils 4174, PD-seeded fibrils (using Tg-1-90B as the radioligand), AD Tissue 6843 and/or AD Tissue 2846 was determined. In each experiment, the "hot" concentration was 2 nM. The structures of the new compounds and their $K_i$ are depicted in Table 5 below.

TABLE 5
| Compound | Structure | Substrate | $K_i$ (nM) |
|---|---|---|---|
| TZ46-101 | 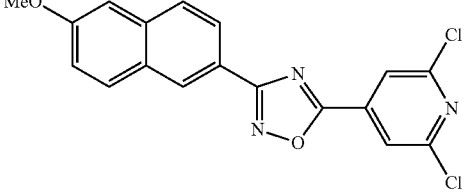 | Fibrils 4174 | ND |
| TZ46-102 | 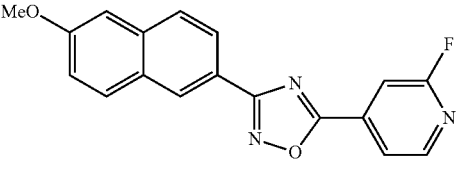 [SMILES: COc1ccc2cc(-c3noc(-c4ccnc(F)c4)n3)ccc2c1] | Fibrils 4174 | 203 |
| TZ46-117 | 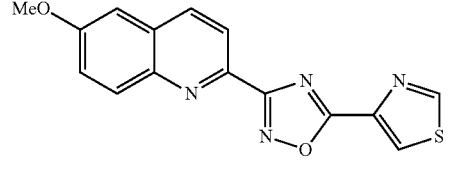 [SMILES: COc1ccc2nc(-c3noc(-c4cocn4)n3)ccc2c1] | Fibrils 4174 | 156 |
| TZ46-120 | 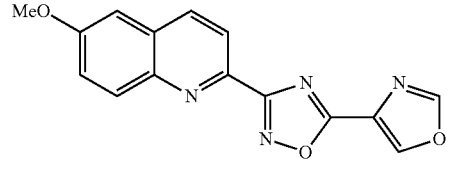 | Fibrils 4174 | 646 |
| TZ46-132 | 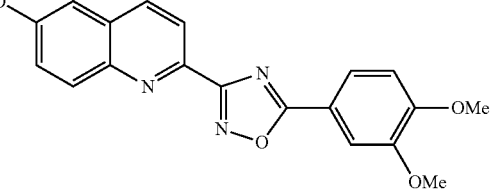 | Fibrils 4174 | ND |
| TZ46-133 | 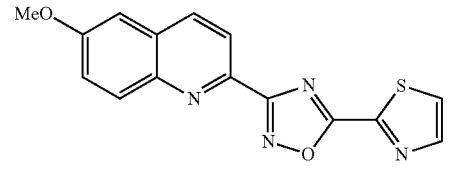 [SMILES: COc1ccc2nc(-c3noc(-c4nccs4)n3)ccc2c1] | Fibrils 4174 | ND |
| TZ46-136 | 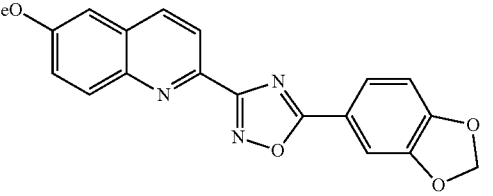 | Fibrils 4174 | 162 |
| TZ46-139 | 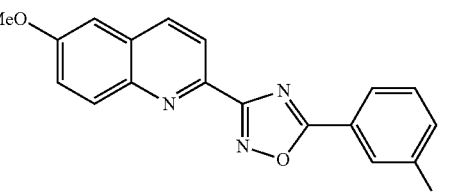 | Fibrils 4174 | 222 |

TABLE 5-continued

| Compound | Structure | Substrate | $K_i$ (nM) |
|---|---|---|---|
| TZ46-140 | 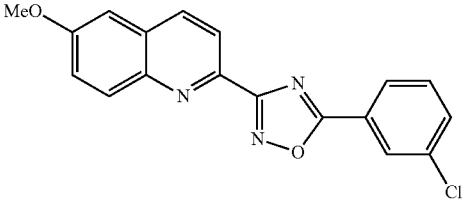 [SMILES: COc1ccc2nc(-c3noc(-c4cccc(Cl)c4)n3)ccc2c1] | Fibrils 4174 | ND |
| TZ46-147 | 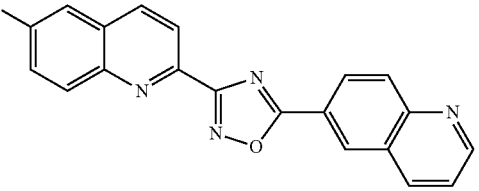 | Fibrils 4174<br>PD-seeded fibrils (Tg-1-90B)<br>AD Tissue 6843<br>AD Tissue 2846 | 96<br>39<br><br>21<br>30 |
| TZ46-148 | 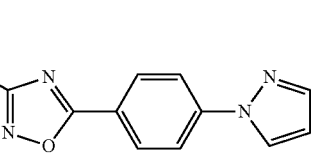 | Fibrils 4174<br>PD-seeded fibrils (Tg-1-90B)<br>AD Tissue 6843<br>AD Tissue 2846 | 82<br>17<br><br>13<br>7 |
| TZ46-155 | 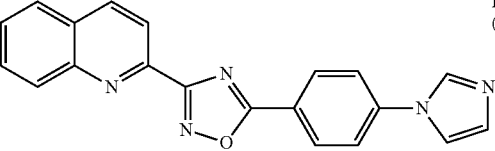 | PD-seeded fibrils (Tg-1-90B) | 230 |

Figure 11A:
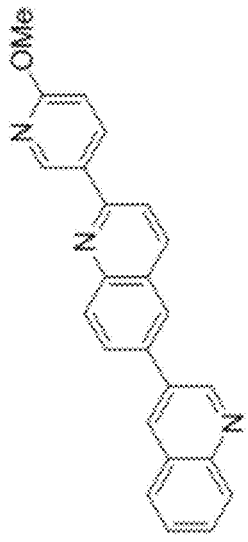
FIG. 11A depicts the structure and molecular weight of TZ55-101.
Figure 11B:
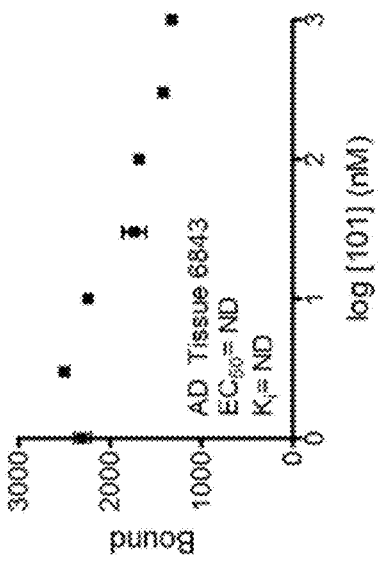
FIG. 11B is a plot of a heterologous competition binding assay of TZ55-101 in the presence of the radioligand [$^{11}$C] Tg-1-90-B and PD fibrils.
Figure 11C:
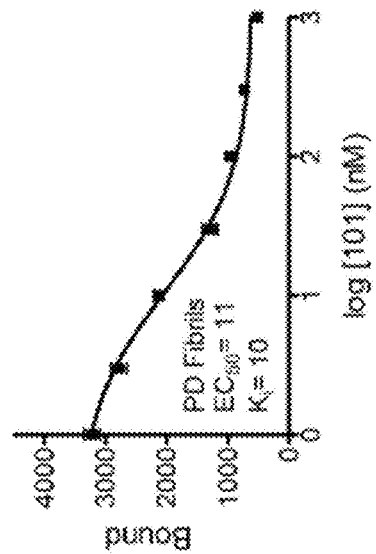
FIG. 11C is a plot of a heterologous competition binding assay of TZ55-101 in the presence of the radioligand [$^{11}$C] Tg-1-90-B and PD fibrils.

Example 43. Heterologous Binding Competition Assays of Compounds on PD-Seeded Fibrils The equilibrium inhibitor constant ($K_i$) of a series of compounds was measured using heterologous radioactive binding assays with [$^{18}$F]TZ61-44, [$^{11}$O]Tg-1-90B, or [$^{125}$I]TZ61-84 as the screening radioligands. $EC_{50}$ values for each compound were determined by fitting the data to the equation Y=Bottom+(Top−Bottom)/(1+(X−Log $EC_{50}$)$^{-Hillcoefficient}$) using nonlinear regression by Kaleidagraph software, where Top and Bottom are the Y values for the top and bottom plateaus of the binding curve. The $K_i$ values were derived from the $EC_{50}$ values using the Cheng-Prusoff equation: $K_i=EC_{50}/(1+[radioligand]/K_d)$. FIGS. 5A-5E show the inhibition curves for TG-1-90B, TZ55-101, TZ61-84, TZ55-107, and TZ55-81 using [$^{18}$F]TZ61-44 as the radioligand. FIG. 11B-C show the inhibition curves for two separate experiments on PD fibrils for TZ55-101 using [$^{11}$O]Tg-1-90B as the radioligand. FIGS. 12A-12F show the inhibition curves for TZ66-3, TZ64-015, TZ64-016, TZ64-018, TZ64-019, and TZ64-020 using [$^{18}$F]TZ61-44 as the radioligand. FIGS. 13A-13D show the inhibition curves for TZ66-9, TZ66-8, and TZ55-107 using [$^{18}$F]TZ61-44 as the radioligand.

Figure 11D:
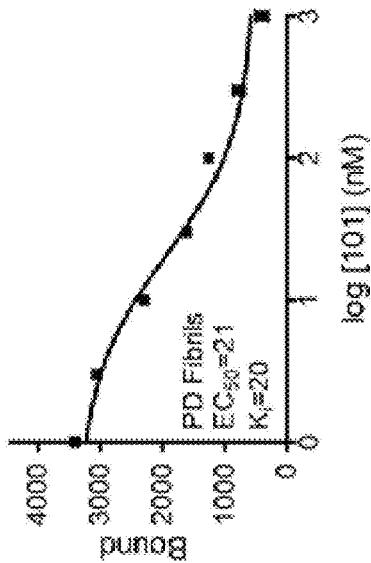
FIG. 11D is a plot of a heterologous competition binding assay of TZ55-101 in the presence of the radioligand [$^{11}$C] Tg-1-90-B and AD tissue 6843.

The binding to AD fibrils was also assessed for TZ55-101 in FIG. 11D. In this experiment, the compound did not show significant affinity for the AD fibrils.

The $EC_{50}$ and calculated $K_i$ for each compound in the presence of PD seeded fibrils is summarized in Table 6, below.

TABLE 6

| Compound | Structure | Radioligand | $EC_{50}$ (nM) | $K_i$ (nM) | FIG. |
|---|---|---|---|---|---|
| TG-1-90B | 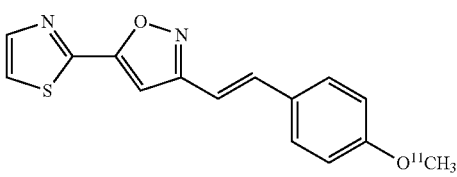 | [$^{18}$F]TZ61-44 | 31 | 29 | 10A |

TABLE 6-continued

| Compound | Structure | Radioligand | EC$_{50}$ (nM) | K$_i$ (nM) | FIG. |
|---|---|---|---|---|---|
| TZ55-101 | 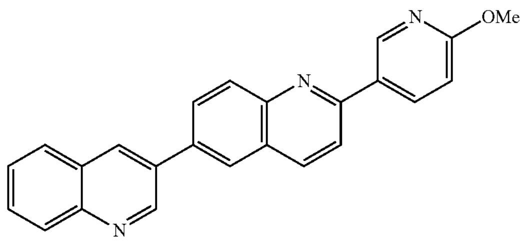 [SMILES: COc1ccc(-c2ccc3cc(-c4cnc5ccccc5c4)ccc3n2)cn1] | [$^{18}$F]TZ61-44<br>Tg-1-90-B (1)<br>Tg-1-90-B (2) | 15<br>21<br>11 | 14<br>20<br>10 | 10B<br>11B<br>11C |
| TZ-61-84 | 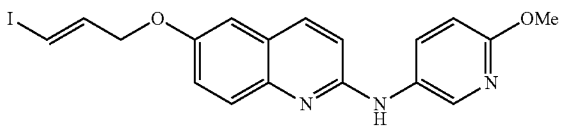 [SMILES: COc1ccc(Nc2ccc3cc(OC/C=C/I)ccc3n2)cn1] | [$^{18}$F]TZ61-44 | 17 | 16 | 5C |
| TZ-55-107 | 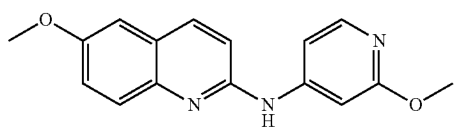 | [$^{18}$F]TZ61-44<br>[$^{18}$F]TZ61-44 | 24<br>36 | 22<br>34 | 5D<br>13D |
| TZ 55-81 | 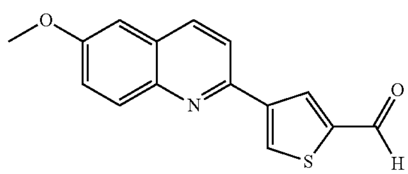 [SMILES: COc1ccc2nc(-c3csc(C=O)c3)ccc2c1] | [$^{18}$F]TZ61-44 | 46 | 43 | 5E |
| TZ64-013 | 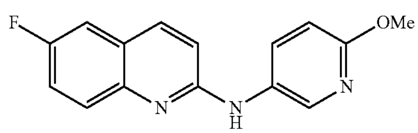 [SMILES: COc1ccc(Nc2ccc3cc(F)ccc3n2)cn1] | [$^{18}$F]TZ61-44 | 29 | 27 | 12A |
| TZ64-015 | 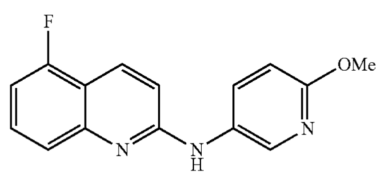 [SMILES: COc1ccc(Nc2ccc3c(F)cccc3n2)cn1] | [$^{18}$F]TZ61-44 | 46 | 43 | 12B |
| TZ64-016 | 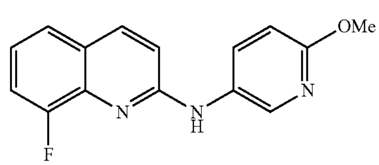 [SMILES: COc1ccc(Nc2ccc3cccc(F)c3n2)cn1] | [$^{18}$F]TZ61-44 | 45 | 42 | 18C |
| TZ64-018 | 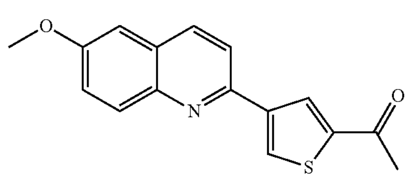 [SMILES: COc1ccc2nc(-c3csc(C(C)=O)c3)ccc2c1] | [$^{18}$F]TZ61-44 | 127 | 119 | 12D |
| TZ64-019 | 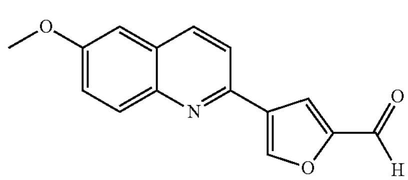 | [$^{18}$F]TZ61-44 | 28 | 27 | 12E |

TABLE 6-continued

| Compound | Structure | Radioligand | EC$_{50}$ (nM) | K$_i$ (nM) | FIG. |
|---|---|---|---|---|---|
| TZ 64-020 | 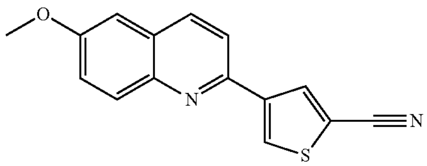 [SMILES: COc1ccc2nc(-c3csc(C#N)c3)ccc2c1] | [$^{18}$F]TZ61-44 | 37 | 34 | 12F |
| TZ66-3 | 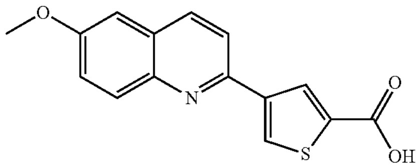 [SMILES: COc1ccc2nc(-c3csc(C(=O)O)c3)ccc2c1] | [$^{18}$F]TZ61-44 | 78 | 73 | 13A |
| TZ66-9 | 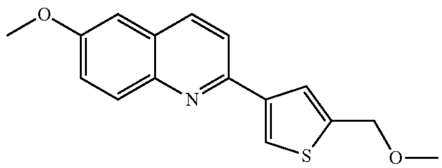 | [$^{18}$F]TZ61-44 | 84 | 78 | 13B |
| TZ66-8 | 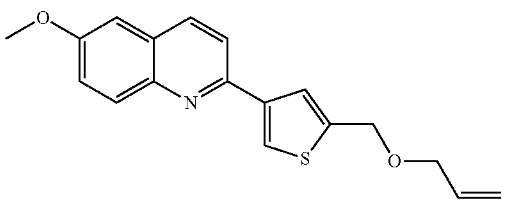 [SMILES: C=CCOCc1cc(-c2ccc3cc(OC)ccc3n2)cs1] | [$^{18}$F]TZ61-44 | 73 | 68 | 13C |

Example 44. Specific Binding of TZ61-84

Figure 17:
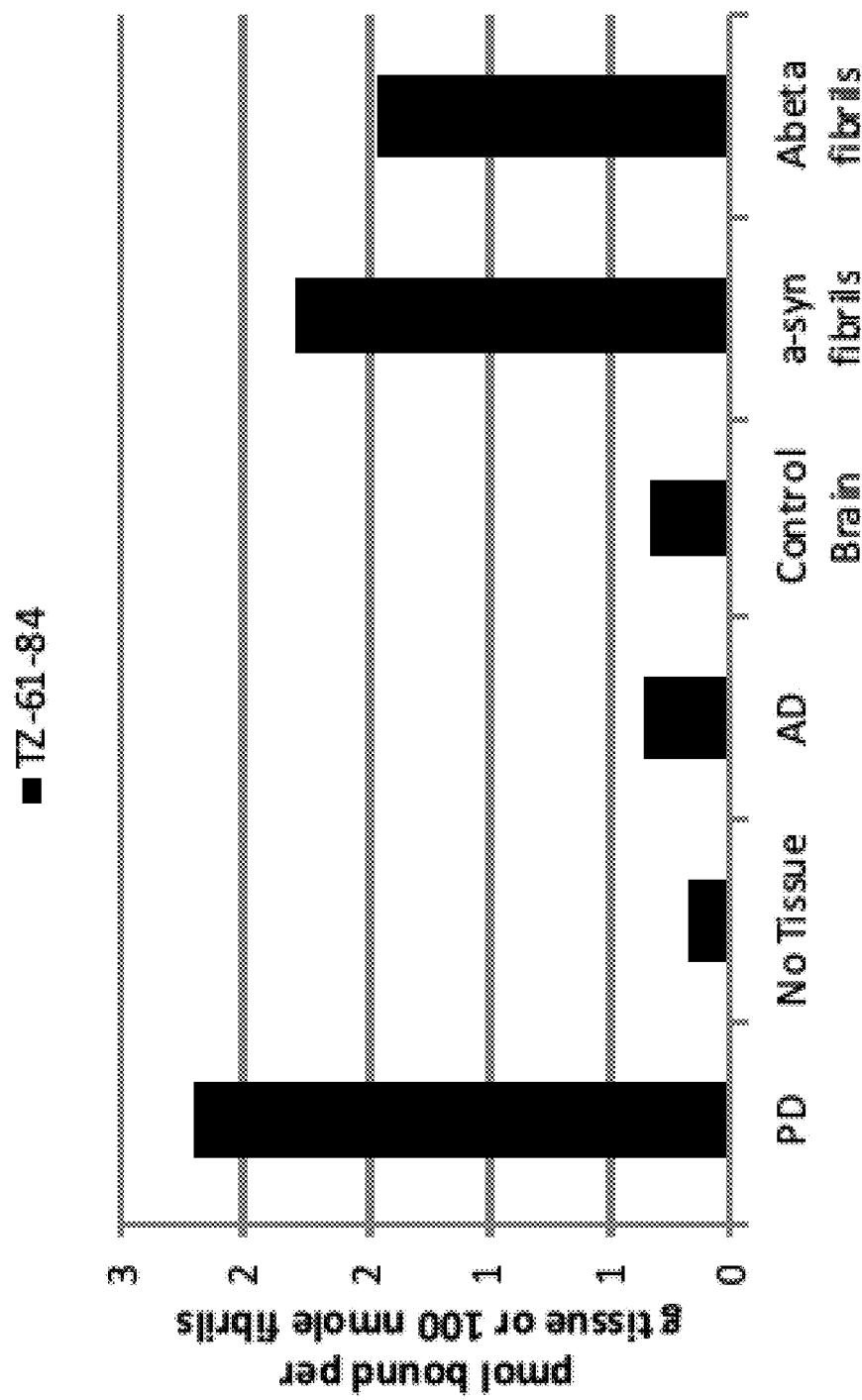
FIG. 17 is a bar graph depicting the amount of [$^{18}$F]TZ61-84 bound to each substrate in the presence of unlabeled TZ61-84

TZ61-84 was screened for binding to Banner PD tissue, AD tissue, α-synuclein fibrils, Aβ fibrils and in controls by measuring how well it displaced [$^{18}$F]TZ-61-84 (at 0.0195 nM) from each substrate. FIG. 17 summarizes the results and shows that TZ61-84 has a high affinity for PD Banner tissue compared to AD Banner tissue and slightly more affinity for α-synuclein fibrils over Aβ fibrils.

Figure 18B:
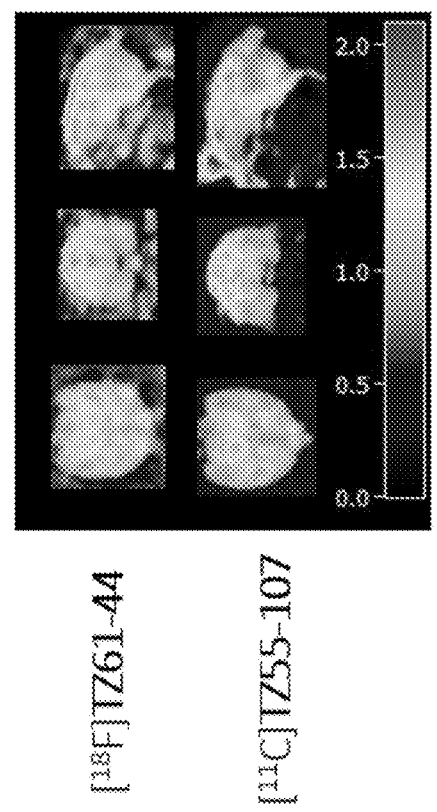
FIG. 18B depicts the distribution volume ratio (DVR) images from male adult cynomolgus macaca brains injected with 9.93 mCi of [$^{18}$F]TZ61-44 or 10.37 mCi of [$^{11}$C]TZ55-107.
Figure 18A:
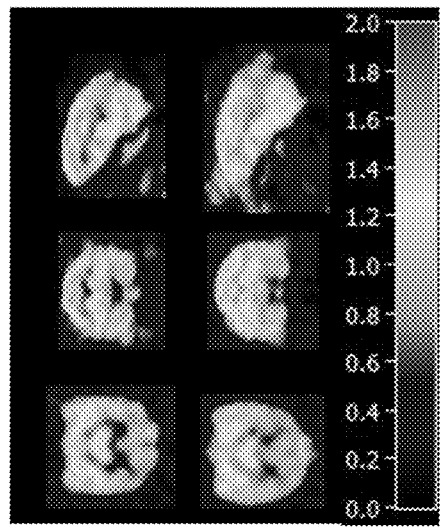
FIG. 18A depicts relative transport rate ($R_1$) images from male adult cynomolgus macaca brains injected with 9.93 mCi of [$^{18}$F]TZ61-44 or 10.37 mCi of [$^{11}$C]TZ55-107.

Example 45. MicroPET Studies of [$^{18}$F]TZ61-44 and [$^{11}$C]TZ55-107 in the Brain of Nonhuman Primate 9.93 mCi of [$^{18}$F]TZ61-44 was injected into a male adult cynomolgus macaca (9.25 Kg) 10.57 mCi of [$^{11}$C]TZ55-107 was injected into was injected into a male adult cynomolgus macaca (9.40 Kg) A simplified reference tissue model (SRTM) and spatially-constraint linear regression algorithm was used to generate R1 and DVR images (FIGS. 18A and 18B). The experimental Log P value is 1.97±0.40 for [$^{18}$F]TZ61-44.

Figure 19A:
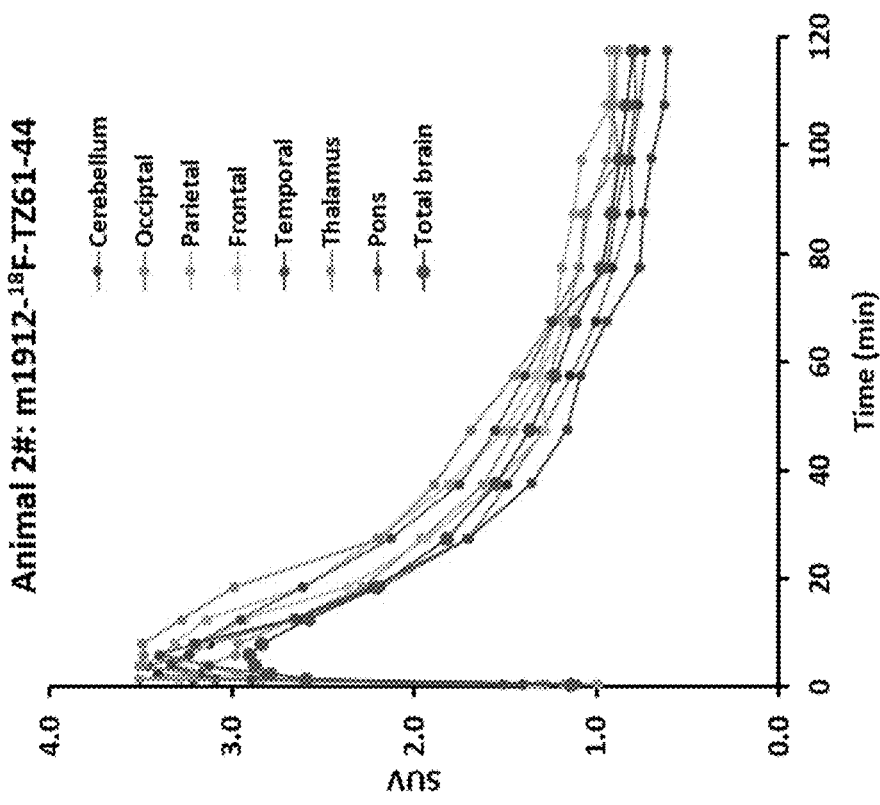
FIG. 19A is a plot of the uptake of [$^{11}$C]TZ55-107 in regions of the brains of male adult cynomolgus macaca over time.
Figure 19B:
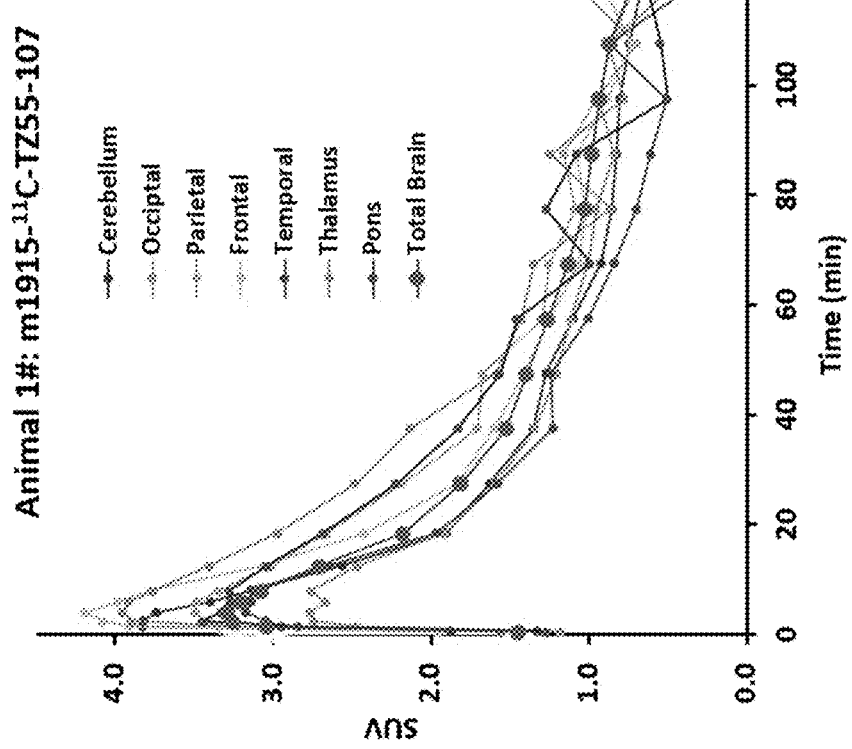
FIG. 19B is a plot of the uptake of [$^{18}$F]TZ61-44 in regions of the brains of male adult cynomolgus macaca over time.

FIGS. 19A and 19B graphically depict the uptake of labeled TZ55-107 and TZ61-44 in the animals. [$^{18}$F]TZ61-44 had highest cortical uptake (SUV) of ~3.48 at 4 min and the uptake ratio at 4 min versus 120 min reached ~4.2 (FIG. 19A); [$^{11}$C]TZ55-107 had highest cortical uptake of ~6.40 at 4 min, and the uptake ratio at 4 min versus 120 min reached ~6.30 (FIG. 19B). These results demonstrate that both [$^{18}$F]TZ61-44 and [$^{11}$C]TZ55-107 are able to penetrate the blood brain barrier and have high cortical uptake and favorable pharmacokinetics in the brain.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A compound having the structure of Formula (I-a) or (I-b), or a pharmaceutically acceptable salt thereof:

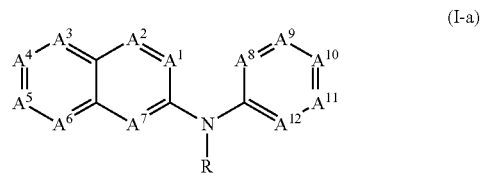

(I-a)

-continued

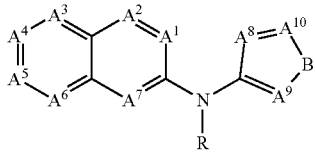
(I-b)

wherein:
each R is hydrogen or substituted or unsubstituted $C_1$-$C_{10}$ alkyl;
each $A^1$ is C—$R^1$;
each $A^2$ is C—$R^2$;
each $A^3$ is C—$R^3$;
each $A^4$ is C—$R^4$;
each $A^5$ is C—$R^5$;
each $A^6$ is C—$R^6$;
each $A^7$ is nitrogen;
each $A^8$ is C—$R^8$;
each $A^9$ is C—$R^9$;
each $A^{10}$ is C—$R^{10}$;
each $A^{11}$ is nitrogen;
each $A^{12}$ is C—$R^{12}$;
B is sulfur or oxygen;
each $R^1$, $R^2$, $R^5$, $R^6$, $R^8$, $R^9$, and $R^{12}$ is hydrogen;
each $R^3$, $R^4$, and $R^{10}$ is independently hydrogen, nitro, halo, cyano, hydroxy, carboxyl, substituted or unsubstituted $C_1$ to $C_6$ alkoxy, substituted or unsubstituted carboxylate, substituted or unsubstituted alkenyloxy, substituted or unsubstituted amino, substituted or unsubstituted thiourea, or substituted or unsubstituted amido,
wherein at least one of $R^3$, $R^4$, and $R^{10}$ is hydroxy or substituted or unsubstituted $C_1$ to $C_6$ alkoxy.

2. The compound of claim 1 wherein each $R^4$ is a halogen, a nitro, halo-substituted $C_1$ to $C_6$ alkoxy, or methoxy and each $R^{10}$ is methoxy.

3. The compound of claim 1 wherein each $R^3$, $R^4$, and $R^{10}$ is independently selected from the group consisting of hydrogen, a halo, a nitro, —CHO, —COCH$_3$, —COOH, —CO$_2$CH$_3$, —OCH$_3$, —OCH$_2$CH$_2$F, —OCH(CH$_3$)$_2$, —OCH$_2$OCH$_3$, —NO$_2$, —CN, —OH, and

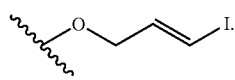

4. The compound of claim 1, selected from the group consisting of:

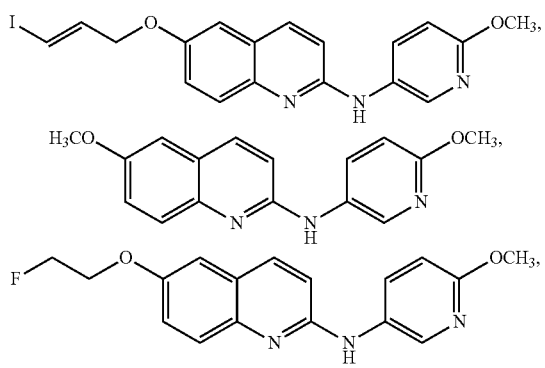

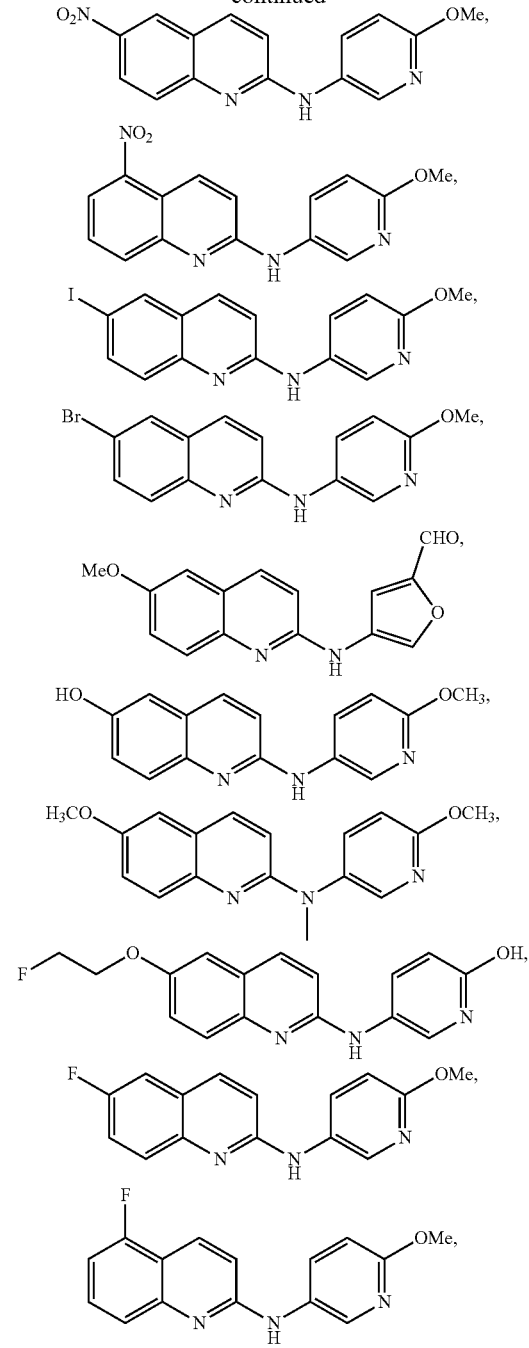

and pharmaceutically acceptable salts thereof.

5. The compound of claim 1 wherein the compound is radiolabeled with a synthetic radioactive isotope.

6. The compound of claim 5 wherein the synthetic radioactive isotope is selected from the group consisting of carbon-11, nitrogen-13, oxygen-15, fluorine-18, bromine-76, iodine-123, and iodine-125.

7. A pharmaceutical composition comprising a radiolabeled compound of claim 6 and at least one excipient.

8. A pharmaceutical composition comprising a compound of claim 1 wherein the composition comprises from about 0.001 mg to about 10 g of the compound and at least about 10 wt. % of the compound in the pharmaceutical composition is radiolabeled.

9. A method of diagnosing or monitoring a synucleinopathy in a subject comprising administering a pharmaceutical composition comprising the compound of claim 5 to a subject; and imaging the subject's brain by positron emission tomography.

10. The method of claim 9 wherein the subject is a mammal.

11. The method of claim 9 wherein the subject comprises a human suffering from Parkinson's disease.

12. The compound of claim 1, having the structure corresponding to:

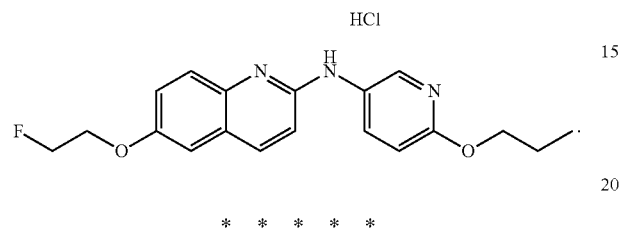

* * * * *